US006417326B1

(12) United States Patent
Cullis et al.

(10) Patent No.: US 6,417,326 B1
(45) Date of Patent: Jul. 9, 2002

(54) FUSOGENIC LIPOSOMES

(75) Inventors: Pieter R. Cullis, Vancouver; Lewis S. L. Choi, Burnaby; Myrna Monck, Vancouver, all of (CA); Austin L. Bailey, Washington, DC (US)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 08/835,281

(22) Filed: Apr. 10, 1997

Related U.S. Application Data

(60) Provisional application No. 60/015,292, filed on Apr. 11, 1996.

(51) Int. Cl.[7] .......................... C07K 7/00; C07K 14/00
(52) U.S. Cl. ................... 530/324; 530/326; 530/327; 514/12; 514/13; 514/14
(58) Field of Search ................ 530/324, 326, 530/327; 514/12, 13, 14

(56) References Cited

U.S. PATENT DOCUMENTS

| | | | | |
|---|---|---|---|---|
| 5,030,455 A | * | 7/1991 | Andoh et al. | 424/468 |
| 5,225,532 A | | 7/1993 | Quentin et al. | 530/331 |
| 5,229,366 A | | 7/1993 | Tsukada et al. | 514/12 |
| 5,372,807 A | | 12/1994 | Poiani et al. | 424/78.36 |
| 5,399,357 A | * | 3/1995 | Akiyama et al. | 424/457 |
| 5,652,274 A | * | 7/1997 | Martin | 514/724 |
| 5,693,609 A | * | 12/1997 | Baker et al. | 514/3 |

FOREIGN PATENT DOCUMENTS

| | | | |
|---|---|---|---|
| DE | 24 55 623 | | 5/1976 |
| EP | 0 451 763 | | 10/1991 |
| JP | 04208296 | * | 7/1992 |
| WO | WO 93/06202 | | 4/1993 |
| WO | WO 93/22343 | | 11/1993 |
| WO | WO 96/10392 | | 4/1996 |
| WO | WO 97/38010 | | 10/1997 |

OTHER PUBLICATIONS

Pierschbacher and Ruoslahti, "Cell attachment activity of fibronectin can be duplicated by small synthetic fragments of the molecule," *Nature* 309: 30–33 (1984).
Saiki et al., "Antimetastatic effects of synthetic polypeptides containing repeated structures of the cell adhesive Arg–Gly–Asp (RGD) and Tyr–Ile–Gly–Ser–Arg (YIGSR) sequences," *Br. J. Cancer* 60: 722–728 (1989).
Murata et al., "Inhibition of tumour cell adhesion by anti–metastatic polypeptide containing a repetitive Arg–Gly–Asp sequence," *Int. J. Biol. Macromol.* 11: 226–232 (1989).
Saiki et al., "Biological activities of synthetic polypeptides containing a repetitive core sequence (Arg–Gly–Asp) of cell adhesion molecules," *Int. J. Biol. Macromol.* 11: 23–25 (1989).
Carey, F.A., Organic Chemistry, McGraw–Hill, New York, pp. 1050–1051, 1987.*
Merck Index. Tenth Edition. pp. 1004–6860, 1983.*
Kato et al. Biochimica et Biophysica Acta, 1063:191–196, 1991.*
Bailey, et al., *Biochimica et Biophysica Acta*, 1324:232–244 (1997).
Brasseur, et al., *Biochimica et Biophysica Acta*, 1029:267–273 (1990).
Chu, et al., *Journal of Liposome Research*, 4(1): 361–395 (1994).
Glushakova, et al., *Chemical Abstracts*, 115 (7) :68322 (1991).
Glushakova, et al., *Biochimica et Biophysica Acta*, 1110:202–208 (1992).
Goormaghtigh, et al., *European Journal of Biochemistry*, 195:421–429 (1991).
Ishiguro, et al., *Biochemistry*, 32:9792–9797 (1993).
Kato, et al., *Biochimica et Biophysica Acta*, 1063:191–196 (1991).
Kono, et al., *Biochimica et Biophysica Acta*, 1164:81–90 (1993).
Lee, et al., *Biochimica et Biophysica Acta*, 1103:157–162 (1992).
Murata, et al., *Biochemistry*, 31:1981–1992 (1992).
Murata, et al., *Biophysical Journal*, 64:724–734 (1993).
Puyal, et al., *Biochimica et Biophysica Acta*, 1195:259–266 (1994).
Pramanick, et al., *Polymer Bulletin*, 18:311–315 (1987).
Rafalski, et al., *Biochemistry*, 30:10211–10220 (1991).
Takahashi, *Biochemistry*, 29:6257–6264 (1990).
Tosi et al., *Biochemical and Biophysical Research Communications*, 212(2): 494–500 (1995).
Yanes, et al., *Chemical Abstracts*, 75:6437 (1971).
Yoshihisa, *Patent Abstracts of Japan*, 016(548) : C–1005 (1992).

* cited by examiner

*Primary Examiner*—Christopher S. F. Low
*Assistant Examiner*—Anish Gupta
(74) *Attorney, Agent, or Firm*—Townsend and Townsend and Crew LLP

(57) ABSTRACT

The present invention relates to liposomes and virosomes and, more particularly, to liposomal and virosomal delivery systems for transporting materials such as drugs, nucleic acids and proteins.

3 Claims, 46 Drawing Sheets wt: GLFGAIAGFIENGWEGMIDG...

E4: GLFEAIAGFIENGWEGMID G

AcE4K: Ac-GLFEAIAGFIENGWEGMIDGK

NHS: N-HYDROXYSUCCINIMIDE
DCC: N, N'-DICYCLOHEXYLCARBODIIMIDE
TFA: TRIFLUOROACETIC ACID

FUSOGENIC LIPOSOMES

This application claim benefit to provisional application No. 60/015,292 filed Apr. 11, 1996.

BACKGROUND OF THE INVENTION

It is well recognized in the medical field that the most effective procedure for treating localized disease is to direct the pharmaceutical or drug agent (hereinafter "drugs") to the affected area, thereby avoiding undesirable toxic effects of systemic treatment. Techniques currently being used to deliver drugs to specific target sites within the body involve the utilization of time-release capsules or gel matrices from which drugs slowly "leak," or the use of implantable "syringes" that mechanically release drugs into muscles or into the blood stream. Another, and perhaps more effective delivery system, encompasses the use of liposomes containing the appropriate drug or chemical. The liposome with encapsulated drug is directed to the specific area of interest and, thereafter, the drug is released. The carrying out of this latter step is the most problematic and, in fact, the greatest barrier to the use of liposomes as drug carriers is making the liposomes release the drugs on demand at the target site of interest.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature, $T_c$. Current methods of drug delivery via liposomes require that the liposome carrier will ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Proc. Natl. Acad. Sci. USA 84:7851 (1987); Biochemistry 28:908 (1989)). When liposomes are endocytosed by a target cell, for example, they can be routed to acidic endosomes which will destabilize the liposome and result in drug release. Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

In addition to the foregoing methods, a liposome having a predetermined phase transition temperature, $T_c$, above body temperature can be used to achieve active drug delivery. In this method, the body temperature will maintain the liposome below the $T_c$ so that the liposome will not become leaky when placed in the body. This method of drug release is capable of "on demand" drug delivery since such liposomes experience a greatly increased membrane permeability at their $T_c$ which, in turn, enables drug or chemical release. To release drugs from such phase transition liposomes when in the body, heat must be applied until the $T_c$ is achieved. Unfortunately, the application of heat can, in itself, create problems within the body and, frequently, the adverse effects of the heat treatment outweigh the beneficial effects of using the liposome as a drug delivery vehicle. Moreover, such liposomes must be made of highly purified and expensive phase transition temperature phospholipid materials.

In view of the foregoing, there exists a need in the art for a method for targeted drug delivery that overcomes the disadvantages of the currently available methods. Specifically, a parenteral delivery system is required that would be stable in the circulation, following intravenous administration, allowing retention of encapsulated or associated drug or therapeutic agent(s). This delivery system would be capable of accumulating at a target organ, tissue or cell via either active targeting (e.g., by incorporating an antibody or hormone on the surface of the liposomal vehicle) or via passive targeting, as seen for long-circulating liposomes. Following accumulation at the target site, the liposomal carrier would become fusogenic, without the need for any external stimulus, and would subsequently release any encapsulated or associated drug or therapeutic agent in the vicinity of the target cell, or fuse with the target cell plasma membrane introducing the drug or therapeutic agent into the cell cytoplasm. In certain instances, fusion of the liposomal carrier with the plasma membrane would be preferred because this would provide more specific drug delivery and, hence, minimize any adverse effects on normal, healthy cells or tissues. In addition, in the case of therapeutic agents such as DNA, RNA, proteins, peptides, etc., which are generally not permeable to the cell membrane, such a fusogenic carrier would provide a mechanism whereby the therapeutic agent could be delivered to its required intracellular site of action. Further, by avoiding the endocytic pathway, the therapeutic agent would not be exposed to acidic conditions and/or degradative enzymes that could inactivate said therapeutic agent. Quite surprisingly, the present invention addresses this need by providing such a method.

SUMMARY OF THE INVENTION

In one embodiment, the present invention provides a fusogenic liposome comprising a lipid capable of adopting a non-lamellar phase, yet capable of assuming a bilayer structure in the presence of a bilayer stabilizing component; and a bilayer stabilizing component reversibly associated with the lipid to stabilize the lipid in a bilayer structure. Such fusogenic liposomes are extremely advantageous because the rate at which they become fusogenic can be not only predetermined, but varied as required over a time scale ranging from minutes to days. Control of liposome fusion can be achieved by modulating the chemical stability and/or exchangeability of the bilayer stabilizing component(s).

By controlling the composition and concentration of the bilayer stabilizing component, one can control the chemical stability of the bilayer stabilizing component and/or the rate at which the bilayer stabilizing component exchanges out of the liposome and, in turn, the rate at which the liposome becomes fusogenic. In addition, other variables including, for example, pH, temperature, ionic strength, etc. can be used to vary and/or control the rate at which the liposome becomes fusogenic.

In another embodiment, the present invention provides a method for delivering a therapeutic compound to a target cell at a predetermined rate, the method comprising: administering to a host containing the target cell a fusogenic liposome which comprises a bilayer stabilizing component, a lipid capable of adopting a non-lamellar phase, yet capable of assuming a bilayer structure in the presence of the bilayer stabilizing component, and a therapeutic compound or a pharmaceutically acceptable salt thereof. Administration may be by a variety of routes, but the therapeutic compounds are preferably given intravenously or parenterally. The fusogenic liposomes administered to the host may be unilamellar, having a mean diameter of 0.05 to 0.45 microns, more preferably from 0.05 to 0.2 microns.

In yet another embodiment, the present invention provides a lipopeptide, the lipopetide comprising (or consisting essentially of) a lipid covalently attached to a peptide by means of an amide bond. Typically, the amide bond is formed between a carboxyl group of the lipid and an amino group of the peptide. In addition, the present invention provides a pharmaceutical composition for introducing a therapeutic compound into a cell of a host, the pharmaceutical composition comprising: a liposome containing a lipopeptide, the lipopeptide comprising a lipid covalently attached to a peptide by means of an amide bond; a therapeutic compound contained in the liposome; and a pharmaceutically acceptable carrier. Such liposomes are stable at physiological pH, but after being internalized by cells through an endocytic pathway, the liposomes exposed to the acidic pH of the endosome are destabilized and fuse with the endosome membrane, resulting in release of their contents into the cytoplasm.

In another embodiment, the present invention provides fusogenic pH-sensitive oligomers, the oligomers having the general structures

and

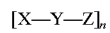

in which: X is a trifunctional substrate, wherein at least one of the functional groups is a carboxyl group or a protected carboxyl group; Z is a trifunctional substrate, wherein at least one of the functional groups is a carboxyl group or a protected carboxyl group; Y is ethylene glycol; and n is an integer having a value ranging from 1 to 20. In addition, the present invention provides a pharmaceutical composition for introducing a therapeutic compound into a cell of a host, the pharmaceutical composition comprising: a liposome containing a pH-sensitive fusogenic polymer, the pH-sensitive fusogenic polymer as described above; a therapeutic compound contained in the liposome; and a pharmaceutically acceptable carrier.

The present invention further provides pharmaceutical compositions for treatment of hosts. The compositions generally comprise a virosome having a membrane and an aqueous interior, wherein a viral membrane fusion protein, e.g., influenza hemagglutinin protein, is contained in the membrane, and further comprising a therapeutic compound contained in the virosome and a pharmaceutically acceptable carrier. The therapeutic compound may be carried in the aqueous interior or in the membrane of the virosome. Nucleic acids, proteins, peptides, and other compounds may be carried in the compositions of the present invention. Generally, the hemagglutinin is derived from influenza A.

Also provided are methods for introducing therapeutic compounds into cells of a host. The methods typically include contacting the cell with a virosome containing the therapeutic compound. A wide variety of compounds may be introduced into host cells by the present methods. The virosomes may be administered to the host by a variety of routes, including by parenteral, topical or inhalation administration.

Other features, objects and advantages of the invention and its preferred embodiments will become apparent from the detailed description which follows.

BRIEF DESCRIPTION OF THE DRAWINGS

FIG. 12 illustrates programmable fusion. Fusion between fluorescently labelled and unlabelled liposomes containing 2 mol % of the indicated PE-PEG$_{2000}$ was assayed as described under FIG. 10. The % fusion was calculated as described in the examples.

FIG. 13 illustrates the effect of PEG molecular weight on fusion.

FIG. 41 illustrates the effects of pH and the presence of lipid vesicles on the secondary structure of AcE4K and Lipo-AcE4K.

FIG. 42 sets forth the tryptophan fluorescence emission spectra of AcE4K and Lipo-AcE4K showing the effects of pH and the presence of lipid vesicles.

FIG. 44 illustrates the effects of Lipo-AcE4K concentration on lipid mixing and leakage in POPC LUVs.

FIG. 45 illustrates the exchange of Lipo-AcE4K between vesicle populations and lipid mixing with membranes lacking lipopeptide.

FIG. 46 illustrates the lipid mixing and leakage in EPC:Chol (55:45) LUVs.

FIG. 49A: 10 mol % Lipo-AcE4K was added from DMSO stock solution to fluorescently labeled liposomes and pre-incubated at 25° C. for 5 minutes prior to addition of erythrocyte membranes. The lipopeptide is present only in the outer monolayer of vesicles. FIG. 49B: Lipid-mixing assays of co-lyophilized 10 mol % Lipo-AcE4K in EPC/Chol (55:45) with erythrocyte ghosts. The lipopeptide is present in inner and outer monolayers of the fluorescently labeled vesicles.

DETAILED DESCRIPTION OF THE INVENTION AND PREFERRED EMBODIMENTS

CONTENTS

Figure 1:
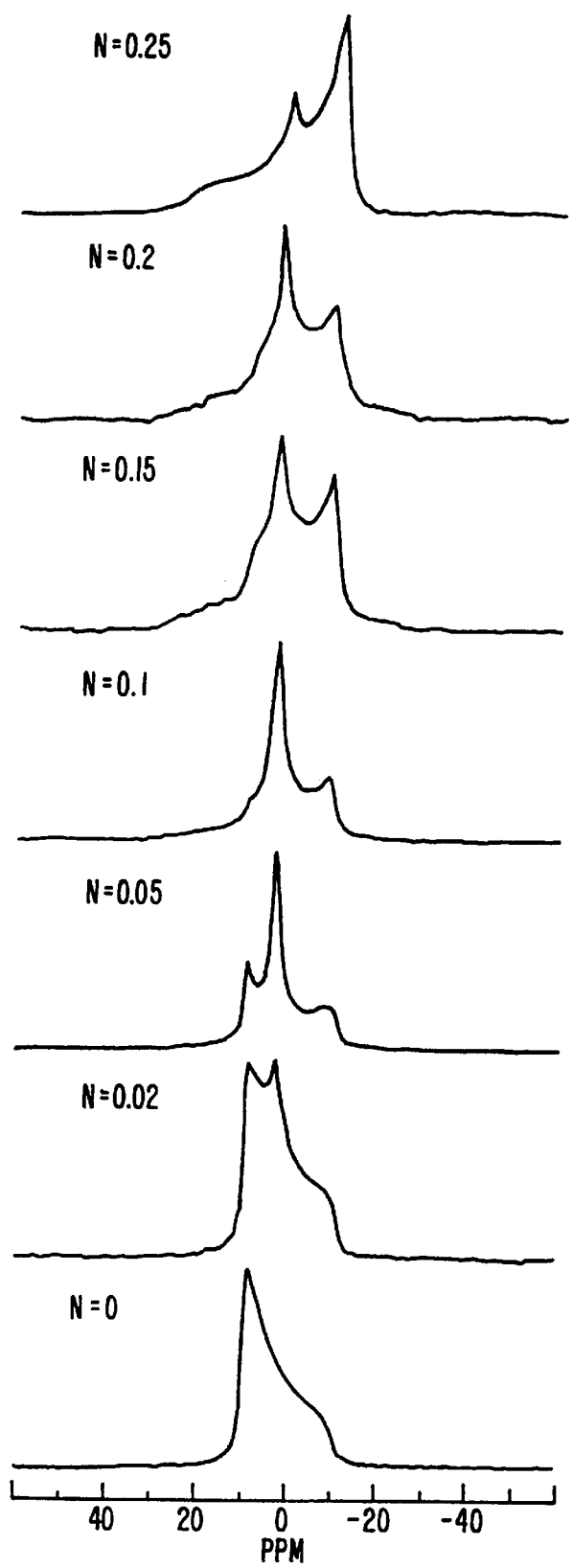
FIG. 1 illustrates the concentration dependence of bilayer stabilization by a bilayer stabilizing component (BSC). Multilamellar vesicles were prepared, as described in the examples, from mixtures of DOPE:cholesterol:DOPE-PEG$_{2000}$, 1:1:N, where N is the proportion of DOPE-PEG$_{2000}$ as indicated in the FIG. 1. $^{31}$P-NMR spectra were determined at 20° C. after the sample had been allowed to equilibrate for 30 minutes.

I. Glossary
II. Fusogenic Liposomes Containing Bilayer Stabilizing Components
III. Fusogenic Liposomes Containing Fusogenic Peptides
IV. Fusogenic Liposomes Containing Fusogenic Polymers
V. Methods of Preparing Liposomes
VI. Virosome-Mediated Intracellular Delivery of Therapeutic Agents
VII. Examples

I. Glossary

The term "acyl" refers to a radical produced from an organic acid by removal of the hydroxyl group. Examples of acyl radicals include acetyl, pentanoyl, palmitoyl, stearoyl, myristoyl, caproyl and oleoyl.

The term "lipid" refers to any suitable material resulting in a bilayer such that a hydrophobic portion of the lipid material orients toward the bilayer while a hydrophilic portion orients toward the aqueous phase. Amphipathic lipids are necessary as the primary lipid vesicle structural element. Hydrophilic characteristics derive from the presence of phosphate, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). The preferred amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidyicholine, lysophosphatidylcholine, lysophosphatidylethanolamine, dipalmitoylphosphatidylcholine, dioleoylphosphatidylcholine, distearoylphosphatidylcholine or dioleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "neutral lipid" refers to any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include cardiolipin, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

The term "transfection" as used herein, refers to the introduction of polyanionic materials, particularly nucleic acids, into cells. The term "lipofection" refers to the introduction of such materials using liposome complexes. The polyanionic materials can be in the form of DNA or RNA which is linked to expression vectors to facilitate gene expression after entry into the cell. Thus, the polyanionic material used in the present invention is meant to include DNA having coding sequences for structural proteins, receptors and hormones, as well as transcriptional and translational regulatory elements (i.e., promoters, enhancers, terminators and signal sequences) and vector sequences. Methods of incorporating particular nucleic acids into expression vectors are well known to those of skill in the art, but are described in detail in, for example, Sambrook, et al., *Molecular Cloning: A Laboratory Manual* (2nd ed.), Vols. 1–3, Cold Spring Harbor Laboratory, (1989) or *Current Protocols in Molecular Biology*, F. Ausubel, et al., ed. Greene Publishing and Wiley-Interscience, New York (1987), both of which are incorporated herein by reference.

"Peptides," "polypeptides" and "oligopeptides" are chains of amino acids (typically L-amino acids) whose a carbons are linked through peptide bonds formed by a condensation reaction between the carboxyl group of the α carbon of one amino acid and the amino group of the α carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free α-amino group on the amino acid at the amino terminal of the peptide, or to the α-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a polypeptide are numbered in order, starting at the amino terminal and increasing in the direction of the carboxy terminal of the polypeptide. Thus, when one amino acid is said to "follow" another, that amino acid is positioned closer to the carboxy terminal of the polypeptide than the "preceding" amino acid.

The term "residue" is used herein to refer to an amino acid or an amino acid mimetic that is incorporated into a polypeptide by an amide bond or an amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the fusogenic peptides to which the phrase refers. Thus, the description of a polypeptide "consisting essentially of . . . " excludes any amino acid substitutions, additions, or deletions that would substantially alter the biological activity of that peptide.

The amino acids referred to herein are described by shorthand designations as follows:

TABLE I

Amino Acid Nomenclature

| Name | 3-letter | 1 letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

II. Fusogenic Liposomes Containing Bilayer Stabilizing Components

In one embodiment of the present invention, a fusogenic liposome is provided, the fusogenic liposome comprising: a lipid capable of adopting a non-lamellar phase, yet capable of assuming a bilayer structure in the presence of a bilayer stabilizing component; and a bilayer stabilizing component reversibly associated with the lipid to stabilize the lipid in a bilayer structure. Such fusogenic liposomes are advantageous because the rate at which they become fusogenic can be not only predetermined, but varied as required over a time scale of a few minutes to several tens of hours. It has been found, for example, that by controlling the composition and concentration of the bilayer stabilizing component, one can control the rate at which the bilayer stabilizing component exchanges out of the liposome and, in turn, the rate at which the liposome becomes fusogenic.

The polymorphic behavior of lipids in organized assemblies can be explained qualitatively in terms of the dynamic molecular shape concept (see, Cullis, et al., in "Membrane Fusion" (Wilschut, J. and D. Hoekstra (eds.), Marcel Dekker, Inc., New York, (1991)). When the effective cross-sectional areas of the polar head group and the hydrophobic region buried within the membrane are similar then the lipids have a cylindrical shape and tend to adopt a bilayer conformation. Cone-shaped lipids which have polar head groups that are small relative to the hydrophobic component, such as unsaturated phosphatidylethanolamines, prefer non-bilayer phases such as inverted micelles or inverse hexagonal phase ($H_{II}$). Lipids with head groups that are large relative to their hydrophobic domain, such as lysophospholipids, have an inverted cone shape and tend to form micelles in aqueous solution. The phase preference of a mixed lipid system depends, therefore, on the contributions of all the components to the net dynamic molecular shape. As such, a combination of cone-shaped and inverted cone-shaped lipids can adopt a bilayer conformation under conditions where either lipid in isolation cannot (see, Madden and Cullis, *Biochim. Biophys. Acta,* 684:149–153 (1982)).

A more formalized model is based on the intrinsic curvature hypothesis (see, e.g., Kirk, et al., *Biochemistry,*

23:1093–1102 (1984)). This model explains phospholipid polymorphism in terms of two opposing forces. The natural tendency of a lipid monolayer to curl and adopt its intrinsic or equilibrium radius of curvature ($R_o$) which results in an elastically relaxed monolayer is opposed by the hydrocarbon packing constraints that result. Factors that decrease the intrinsic radius of curvature, such as increased volume occupied by the hydrocarbon chains when double bonds are introduced, tend to promote $H_{II}$ phase formation. Conversely, an increase in the size of the headgroup increases $R_o$ and promotes bilayer formation or stabilization. Introduction of apolar lipids that can fill the voids between inverted lipid cylinders also promotes $H_{II}$ phase formation (see, Gruner, et al., *Proc. Natl. Acad. Sci. USA*, 82:3665–3669 (1989); Sjoland, et al., *Biochemistry*, 28:1323–1329 (1989)).

Lipids which can be used to form the fusogenic liposomes of the present invention are those which adopt a non-lamellar phase under physiological conditions or under specific physiological conditions, e.g., in the presence of calcium ions, but which are capable of assuming a bilayer structure in the presence of a bilayer stabilizing component. Such lipids include, but are not limited to, phosphatidylenthanolamines, ceramides, glycolipids, or mixtures thereof. Other lipids known to those of skill in the art to adopt a non-lamellar phase under physiological conditions can also be used. Moreover, it will be readily apparent to those of skill in the art that other lipids can be induced to adopt a non-lamellar phase by various non-physiological changes including, for example, changes in pH or ion concentration (e.g., in the presence of calcium ions) and, thus, they can also be used to form the fusogenic liposomes of the present invention. In a presently preferred embodiment, the fusogenic liposome is prepared from a phosphatidylethanolamine. The phosphatidylethanolamine can be saturated or unsaturated. In a presently preferred embodiment, the phosphatidylyethanolamine is unsaturated. In an equally preferred embodiment, the fusogenic liposome is prepared from a mixture of a phosphatidylethanolamine (saturated or unsaturated) and a phosphatidylserine. In another equally preferred embodiment, the fusogenic liposome is prepared from a mixture of a phosphatidylethanolamine (saturated or unsaturated) and a cationic lipid.

Examples of suitable cationic lipids include, but are not limited to, the following: DC-Chol, 3β-(N-(N',N'-dimethylaminoethane)carbamoyl)cholesterol (see, Gao, et al., *Biochem. Biophys. Res. Comm.* 179:280–285 (1991); DDAB, N,N-distearyl-N,N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see, commonly owned U.S. patent application Ser. No. 08/316,399, filed Sep. 30, 1994, which is incorporated herein by reference); DOGS, diheptadecylamidoglycyl spermidine; DOSPA, N-(1-(2,3-dioleyloxy)propyl)-N-(2-(sperminecarboxamido)ethyl)-N,N-dimethylammonium trifluoroacetate; DOTAP, N-(1-(2,3-dioleoyloxy)propyl)-N,N,N-trimethylammonium chloride; and DOTMA, N-(1-(2,3-dioleyloxy)propyl)-N,N,N-trimethylammonium chloride. In a presently preferred embodiment, N,N-dioleoyl-N,N-dimethylammonium chloride is used in combination with a phosphatidylethanolamine.

In accordance with the present invention, lipids adopting a non-lamellar phase under physiological conditions can be stabilized in a bilayer structure by bilayer stabilizing components which are either bilayer forming themselves, or which are of a complementary dynamic shape. The non-bilayer forming lipid is stabilized in the bilayer structure only when it is associated with, i.e., in the presence of, the bilayer stabilizing component. In selecting an appropriate bilayer stabilizing component, it is imperative that the bilayer stabilizing component be capable of transferring out of the liposome, or of being chemically modified by endogenous systems such that, with time, it loses its ability to stabilize the lipid in a bilayer structure. Only when liposomal stability is lost or decreased can fusion of the liposome with the plasma membrane of the target cell occur. The bilayer stabilizing component is, therefore, "reversibly associated" with the lipid and only when it is associated with the lipid is the lipid constrained to adopt the bilayer structure under conditions where it would otherwise adopt a non-lamellar phase. As such, the bilayer stabilizing components of the present invention must be capable of stabilizing the lipid in a bilayer structure, yet they must be capable of exchanging out of the liposome, or of being chemically modified by endogenous systems so that, with time, they lose their ability to stabilize the lipid in a bilayer structure, thereby allowing the liposome to become fusogenic.

Examples of suitable bilayer stabilizing components include, but are not limited to, lipid, lipid-derivatives, detergents, proteins and peptides. In a presently preferred embodiment, the bilayer stabilizing component is polyethyleneglycol conjugated to, i.e., coupled to, a phosphatidylethanolamine. In an equally preferred embodiment, the bilayer stabilizing component is polyethyleneglycol conjugated to a ceramide. Polyethyleneglycol can be conjugated to a phosphatidylethanolamine or, alternatively, to a ceramide using standard coupling reactions known to and used by those of skill in the art. In addition, preformed polyethyleneglycol-phosphatidylethanolamine conjugates are commercially available from Avanti Polar Lipids (Alabaster, Ala.).

Polyethyleneglycols of varying molecular weights can be used to form the bilayer stabilizing components of the present invention. Polyethyleneglycols of varying molecular weights are commercially available from a number of different sources or, alternatively, they can be synthesized using standard polymerization techniques well-known to those of skill in the art. In a presently preferred embodiment, the polyethylene glycol has a molecular weight ranging from about 200 to about 10,000, more preferably from about 1,000 to about 8,000, and even more preferably from about 2,000 to about 6,000. Generally, it has been found that increasing the molecular weight of the polyethyleneglycol reduces the concentration of the bilayer stabilizing component required to achieve stabilization.

Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE).

As with the phosphatidylethanolamines, ceramides having a variety of acyl chain groups of varying chain lengths and degrees of saturation can be coupled to polyethyleneglycol to form the bilayer stabilizing component. It will be apparent to those of skill in the art that in contrast to the phosphatidylethanolamines, ceramides have only one acyl group which can be readily varied in terms of its chain length and degree of saturation. Ceramides suitable for use in accordance with the present invention are commercially available. In addition, ceramides can be isolated, for example, from egg or brain using well-known isolation techniques or, alternatively, they can be synthesized using the methods and techniques disclosed in U.S. patent application Ser. No. 08/316,429, filed Sep. 30, 1994, and U.S. patent application Ser. No. 08/486,214, filed Jun. 7, 1995, the teachings of which are incorporated herein by reference. Using the synthetic routes set forth in the foregoing application, ceramides having saturated or unsaturated fatty acids with carbon chain lengths in the range of $C_2$ to $C_{31}$ can be prepared.

In addition to the foregoing, detergents, proteins and peptides can be used as bilayer stabilizing components. Detergents which can be used as bilayer stabilizing components include, but are not limited to, Triton X-100, deoxycholate, octylglucoside and lyso-phosphatidylcholine. Proteins which can be used as bilayer stabilizing components include, but are not limited to, glycophorin and cytochrome oxidase. Cleavage of the protein, by endogenous proteases, resulting in the loss of the bulky domain external to the bilayer would be expected to reduce the bilayer stabilizing ability of the protein. In addition, peptides which can be used as bilayer stabilizing components include, for example, the pentadecapeptide, alanine-(aminobutyric acid-alanine)$_{14}$. This peptide can be coupled, for example, to polyethyleneglycol which would promote its transfer out of the bilayer. Alternatively, peptides such as cardiotoxin and melittin, both of which are known to induce non-lamellar phases in bilayers, can be coupled to PEG and might thereby be converted to bilayer stabilizers in much the same way that PE is converted from a non-lamellar phase preferring lipid to a bilayer stabilizer when it is coupled to PEG. If the bond between the peptide and the PEG is labile, then cleavage of the bond would result in the loss of the bilayer stabilizing ability and in the restoration of a non-lamellar phase, thereby causing the liposome to become fusogenic.

Typically, the bilayer stabilizing component is present at a concentration ranging from about 0.05 mole percent to about 50 mole percent. In a presently preferred embodiment, the bilayer stabilizing component is present at a concentration ranging from 0.05 mole percent to about 25 mole percent. In an even more preferred embodiment, the bilayer stabilizing component is present at a concentration ranging from 0.05 mole percent to about 15 mole percent. One of ordinary skill in the art will appreciate that the concentration of the bilayer stabilizing component can be varied depending on the bilayer stabilizing component employed and the rate at which the liposome is to become fusogenic.

By controlling the composition and concentration of the bilayer stabilizing component, one can control the rate at which the bilayer stabilizing component exchanges out of the liposome and, in turn, the rate at which the liposome becomes fusogenic. For instance, when a polyethyleneglycol-phosphatidylethanolamine conjugate or a polyethyleneglycol-ceramide conjugate is used as the bilayer stabilizing component, the rate at which the liposome becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the liposome becomes fusogenic. Other methods which can be used to control the rate at which the liposome becomes fusogenic will become apparent to those of skill in the art upon reading this disclosure.

In a presently preferred embodiment, the fusogenic liposomes contain cholesterol. It has been determined that when cholesterol-free liposomes are used in vivo, they have a tendency to absorb cholesterol from plasma lipoproteins and cell membranes. Since this absorption of cholesterol could, in theory, change the fusogenic behavior of the liposomes, cholesterol can be included in the fusogenic liposomes of the present invention so that little or no net transfer of cholesterol occurs in vivo. Cholesterol, if included, is generally present at a concentration ranging from 0.02 mole percent to about 50 mole percent and, more preferably, at a concentration ranging from about 35 mole percent to about 45 mole percent.

III. Fusogenic Liposomes Containing Fusogenic Lipopeptides

In another embodiment, the present invention provides fusogenic liposome containing a fusogenic lipopeptide. More particularly, the present invention provides a lipopetide, the lipopeptide comprising a lipid covalently attached to a peptide by means of an amide bond. Once formed, the lipopeptide can be incorporated into the outer monolayer of a liposome or, alternatively, into both the inner and outer monolayers of a liposome. It has been discovered that the lipopeptide of the present invention form stable bilayers with numerous lipids at a higher pH (e.g., at a pH of about 7.5), but destabilization of these lipid vesicles can be induced by decreasing the pH (e.g., to a pH below about 6.0). This membrane destabilization not only results in extensive leakage of liposomal contents, but also in lipid mixing. Thus, when the lipopeptides of the present invention are incorporated into a liposome, the fusogenic properties of the liposome are enhanced.

As noted above, the lipopeptide of the present invention is formed by covalently attaching a lipid to a peptide by means of an amide bond. A variety of lipids can be used to form the lipopeptides of the present invention. In a presently preferred embodiment, a diacylglycerol is the lipid used to form the lipopeptide. Diacylglycerols suitable for use in accordance with the present invention can have a variety of acyl chain groups of varying chain lengths and degrees of saturation. Such diacylglycerols are commercially available, or can be isolated or synthesized using conventional techniques known to those of skill in the art. Diacylglycerols containing saturated or unsaturated fatty acids with carbon chain lengths in the range of $C_{10}$ to $C_{20}$ are preferred. Examples of such diacylglycerols include, but are not limited to, 1,2-distearoyl-sn-glycerol, 1,2-dioleoyl-sn-glycerol, 1,2-dipalmitoyl-sn-glycerol.

In addition, the peptide used to form the lipopeptide can be any peptide know to promote membrane fusion, i.e., any fusogenic pH-sensitive peptides. Generally, such fusogenic peptides are short in length, capable of insertion in a monolayer in order to destabilize the bilayer membrane and, in addition, such fusogenic peptides generally have a pH-induced conformational change creating well separated hydrophilic and hydrophobic faces. Such fusogenic peptides can be derived from known viral fusion proteins, e.g., the viral fusion protein of influenza hemagglutinin (HA). These peptides adopt amphipathic α-helical structures and penetrate lipid membranes at the pH corresponding to the fusion of the native virus. Examples of fusogenic peptides suitable for use in the lipopeptides of the present invention include, but are not limited to, those described by S. Takahashi ("Conformation of Membrane Fusion-Active 20-Residue Peptides With or Without Lipid Bilayers. Implication of α-Helix Formation for Membrane Fusion," *Biochemistry*, 29:6257–6264 (1990)); R. Ishiguro, et al. ("Orientation of Fusion-Active Synthetic Peptides in Phospholipid Bilayers: Determination by Fourier Transform Infrared Spectroscopy," *Biochemistry*, 32:9792–9797 (1993)); R. Brasseur, et al. ("Orientation into the lipid bilayer of an asymmetric amphipathic helical peptide located at the N-terminus of viral fusion proteins," *Biochimica et Biophysica Acta*, 1029:267–273 (1990)); S. Lee, et al., ("Effect of Amphipathic peptides with different α-helical contents on liposome fusion," *Biochimica et Biophysica Acta*, 1103:157–162 (1992)); K. Kono, et al., ("Fusion activity of an amphophilic polypeptide having acidic amino acid residues: generation of fusion activity by α-Helix formation and charge neutralization," *Biochimica et Biophysica Acta*, 1164:81–90 (1993)); S. E. Glushakova, et al. ("The fusion of artificial lipid membranes induced by the synthetic arenavirus 'fusion peptide'," *Biochimica et Biophysica Acta*, 1110:202–208 (1992)); M. Murata, et al., "Specificity of Amphilic anionic peptides for fusion of phospholipid vesicles," *Biophysical Journal*, 64:724–734 (1993); C. Puyal, et al., "Design of a short membrane-destabilizing peptide covalently bound to liposomes," *Biochimica et Biophysica Acta*, 1195:259–266 (1994); and Goormaghtigh, et al. ("Secondary structure and orientation of the amphipathic peptide GALA in lipid structures (An infrared-spectroscopic approach)," *European Journal of Biochemistry*, 195:421–429 (1991)), the teachings of which are incorporated herein by reference for all purposes.

More particularly, examples of fusogenic peptides suitable for use in accordance with the present invention include, but are not limited to, the following:

Ac-GLFEAIAGFIENGWEGMIDGK (AcE4K) (SEQ ID NO:3);

WEAALAEALAEALAEHLAEALAEALEALAA (GALA) (SEQ ID NO:4);

GGYCLTRWMLIEAELKCFGNTAV (Lassa) (SEQ ID NO:5);

GGYCLTKWMILAAELKCFGNTAV (LCM) (SEQ ID NO:6);

GGYCLEKWMIVASELKCFGNTAI (Takaribe) (SEQ ID NO:7);

GGYCLEQWAIIWAGIKCFDNTVM (Picinde) (SEQ ID NO:8);

GLFEALAEFIEGGWEGLIEG (E5) (SEQ ID NO:9);
GLFEAIAEFIEAIAEFIEG (E5NN) (SEQ ID NO:10);
GWEGLIEGIEGGWEGLIEG (E5CC) (SEQ ID NO:11);
GLFEAIAEFIPGGWEGLIEG (E5P) (SEQ ID NO:12);
GLLEELLELLEELWEELLEG (E8) (SEQ ID NO:13);
Ac-LARLLARLLARL-NHCH$_3$;
Ac-LARLLPRLLARL-NHCH$_3$;
Ac-LPRLLPRLLARL-NHCH$_3$;
Ac-LPRLLPRLLPRL-NHCH$_3$;
FEAALAEALAEALA (SFP-1);
Myr-FEAALAEALAEALA (SFP-2);
WEAALAEALAEALAC (SFP-3); and
poly(Glu-Aib-Leu-Aib)

wherein "Myr" is used to represent myristic acid and "Aib" is used to represent 2-aminoisobutyric acid. Other fusogenic peptides which can be used to form the lipopeptides of the present invention will be known to those of skill in the art.

In addition, it will be readily apparent to those of ordinary skill in the art that the fusogenic peptides set forth above can be subject to various changes, such as insertions, deletions, and substitutions, either conservative or nonconservative, where such changes might provide for certain advantages in their use, i.e., to increase their fusogenic activity. By "conservative substitutions" is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the fusogenic peptides can be identified by single amino acid substitutions, deletions, or insertions using conventional techniques known to those of ordinary skill in the art, this is especially true of the peptides of the present invention being that they are relatively short in length. In addition, the contributions made by the side chains of the residues can be probed via a systematic scan with a specified amino acid (e.g., Ala). As such, examples of fusogenic peptides which can be used to form the lipopeptides of the present invention include those set forth above and conservative modifications thereof.

The lipopeptide of the present invention is formed by covalently attaching a lipid to a peptide by means of an amide bond. The amide bond is generally formed between a carboxyl group of the lipid and an amino group, preferably a primary amino group, of the peptide. The amino group can be present at the N-terminus of the peptide or, alternatively, it can be present in the side chain of the amino acid present at the C-terminus. It will understood by those of skill in the art that the amino groups which are not used to form the amide bond will be protected using standard techniques to prevent reactivity (see, below for illustrative examples of protecting groups for amino groups). In a preferred embodiment, the amino group used in the formation of the amide bond is present in a lysine residue at the C-terminus of the peptide. If a lysine residue is not naturally present at the C-terminus of the peptide, one can readily be added using standard techniques known to those of skill in the art. It has been determined that a lysine residue can be added to the peptide and, in turn, used to form an amide bond with the lipid without adversely affecting the biological properties of the peptide.

Figure 40:
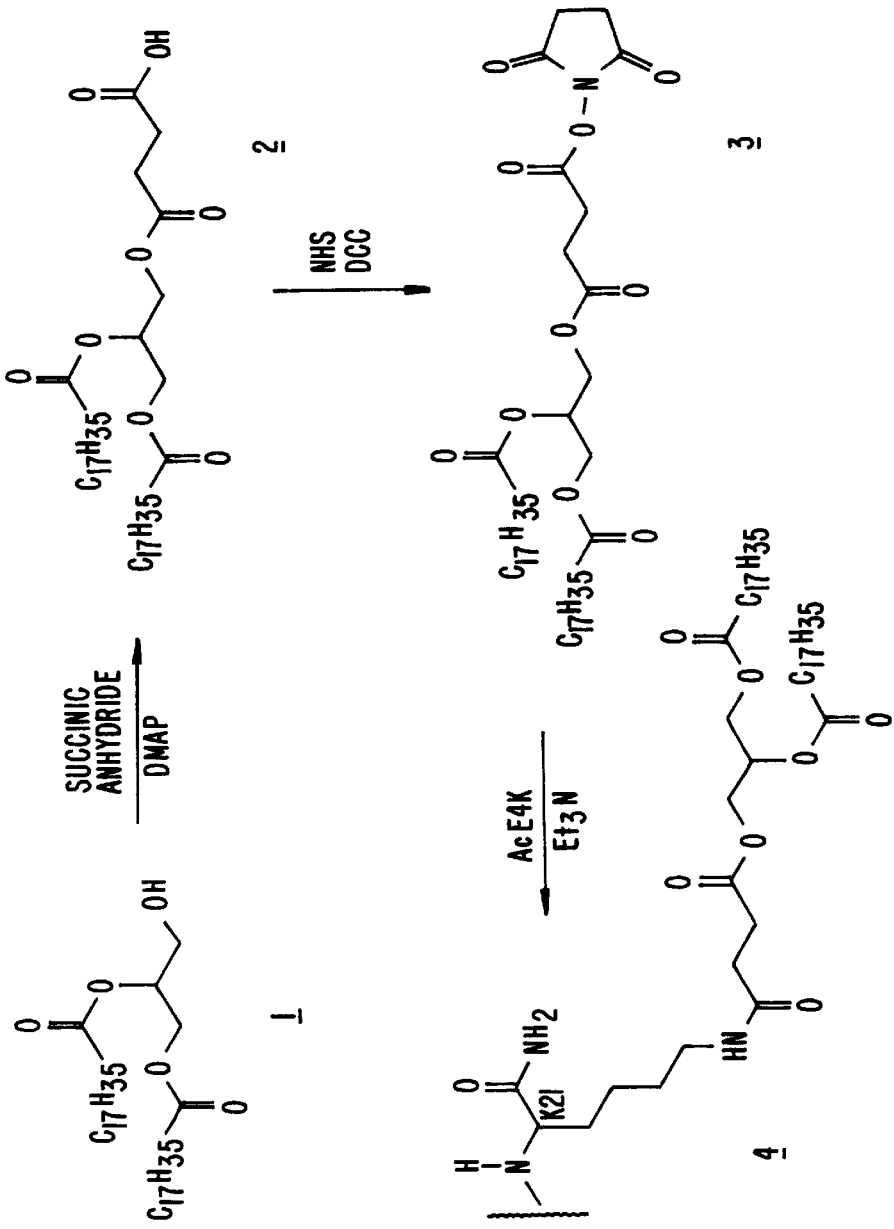
FIG. 40 sets forth the structure and synthesis of the Lipo-AcE4K lipopeptide (4). The activated lipid (3) reacts exclusively with the primary amine on the C-terminal lysine of the peptide.

FIG. 40 illustrates a synthetic scheme which can be used to form the lipopeptides of the present invention. This scheme illustrates the formation of a lipopeptide from the lipid 1,2-distearoyl-sn-glycerol and the fusogenic peptide AcE4K, supra, using an amidation reaction. Those of skill in the art will readily appreciate that this synthetic scheme is illustrative and, thus, that it can be modified in numerous ways. In this reaction, one gram of 1,2-distearoyl-sn-glycerol (1.6 mmol) (1), 0.2 g succinic anhydride (2 mmol), and 0.24 g 4-dimethylaminopyridine (2 mmol) are dissolved in 10 ml of CH$_2$Cl$_2$ and stirred at room temperature for one hour. The resulting acid (2) is isolated by removing solvent by rotary evaporation followed by purification by silica gel chromatography using 10% ethyl acetate in hexane as eluant. About two hundred milligrams of this material (0.28 mmol) and 32 mg of N-hydroxysuccinimide (0.29 mmol) are dissolved in 5 ml of CH$_2$Cl$_2$ and 57 mg of 1,3-dicyclohexylcarbodimide (0.28 mmol) is added with stirring. The reaction is allowed to proceed for about one hour at room temperature after which the mixture is filtered to remove precipitate, and the solvent is removed by rotary evaporation yielding the activated lipid (3). A mixture of 5.6 mg of the peptide AcE4K (2.5 μmol), 4.1 mg of 3 (5.0 μmol) and 15 mg of triethylamine in 1 ml of dimethylsulfoxide (DMSO) are heated to 65° C. to achieve co-dissolution of the lipid and peptide and incubated for one hour. After cooling, the lipopeptide (4) is precipitated by the addition of 5 ml of diethyl ether and centrifuged at 2000 rpm for 5 minutes. The pellet is washed three times with 2 ml of diethyl ether repeating the centrifugation with each wash. The lipopeptide is dried under vacuum and its identity is confirmed by mass spectrometry.

Once formed, the lipopeptide can be incorporated into the outer monolayer of a liposome or, alternatively, into both the inner and outer monolayers of a liposome. This is in contrast to the lipopeptide conjugates of the prior art which, as a result of the chemistry used to synthesize them, can only be present on the outer monolayer of the liposome. If the lipopeptide of the present invention is to be incorporated only into the outer monolayer of the liposome, it is added to a pre-formed liposome. Alternatively, if the lipopeptide of the present invention is to be incorporated into both the inner and outer monolayers of the liposome, then the lipopeptide is used as a component in the formation of the liposome. The lipopeptides of the present invention can be used with liposomes prepared from a variety of lipids. In a preferred embodiment, the lipids used to prepare the liposomes containing the lipopeptides are phosphoglycerides and, in particular, phosphatidylcholine. Examples of such phosphoglycerides are set forth above. In a presently preferred embodiment, the lipids used to form the liposomes are 1-palmitoyl-2-oleoyl-sn-phosphatidylcholine (POPC) and egg phosphatidylcholine (EPC). In a presently preferred embodiment, the liposomes also contain cholesterol.

Typically, the lipopeptide is present at a concentration ranging from about 0.05 mole percent to about 50 mole percent. In a presently preferred embodiment, the lipopeptide is present at a concentration ranging from 0.05 mole percent to about 25 mole percent. In an even more preferred embodiment, the lipopeptide is present at a concentration ranging from 0.05 mole percent to about 10 mole percent. One of ordinary skill in the art will appreciate that the concentration of the lipopeptide can be varied depending on the particular lipopeptide employed and the rate at which the liposome is to become fusogenic. Cholesterol, if included, is generally present at a concentration ranging from 0.2 mole percent to about 50 mole percent and, more preferably, at a concentration ranging from about 20 mole percent to about 45 mole percent.

The lipopeptides of the present invention have significant advantages over those in the prior art. As mentioned, in previously used methods, the fusion peptides are synthesized and anchored to lipid bilayers by a C-terminal cysteine linked to a bifunctional phosphatidylethanolamine derivative (Puyal, et al., *Biochimica et Biophysica Acta*, 1195:259–266 (1994)). Unfortunately, there are a number of drawbacks associated with the cysteine-thioether chemistry used by Puyal, et al. First, it is often difficult to prepare enough peptide containing a cystine residue at the C-terminus. Because they readily dimerize at a pH above 2, such proteins are difficult to synthesize and purify. Second, it is difficult to control the composition of the endproduct. Again, the lipopeptide is prepared in situ and, thus, there is a strong tendency for the peptide to dimerize. As a result of the dimerization of the peptide, it is difficult to achieve 100% reaction and, thus, to know what is truly present. Third, as a result of the chemistry used, leakage of the liposomal content often results. Fourth, the peptide can only be attached to the outer monolayer of a pre-formed liposome.

In contrast, the lipopeptides of the present invention can be readily synthesized and purified. Because the chemistry used to prepare the lipopeptides of the present invention does not require a cysteine residue to be present at the C-terminus, the peptides do not dimerize. Moreover, with the lipopeptides of the present invention, one starts off with a defined and purified product and, thus, one can control the system better, i.e., what one puts into the system, one gets back out. In addition, in contrast to the system of Puyal, et al., one can manipulate the placement of the lipopeptides of the present invention. As previously mentioned, the lipopeptides of the present invention can be incorporated into the outer monolayer of a liposome or, alternatively, into both the inner and outer monolayers of a liposome. In terms of increasing the fusogenic properties of a liposome, there are significant advantages to having the lipopeptide present in both monolayers of the liposome.

It should be noted that since the fusogenic peptides used in the lipopeptides of the present invention are relatively short in length, they can be prepared using any of a number of chemical peptide synthesis techniques well known to those of ordinary skill in the art, including both solution methods and solid phase methods, with solid phase synthesis being presently preferred.

In particular, solid phase synthesis in which the C-terminal amino acid of the peptide sequence is attached to an insoluble support followed by sequential addition of the remaining amino acids in the sequence is the preferred method for preparing the fusogenic peptides of the present invention. Techniques for solid phase synthesis are described by Barany and Merrifield, *Solid-Phase Peptide Synthesis*, in *The Peptides: Analysis, Synthesis, Biology* (Gross and Meienhofer (eds.), Academic Press, N.Y., vol. 2, pp. 3–284 (1980)); Merrifield, et al., *J. Am. Chem. Soc.*, 85:2149–2156 (1963); and Stewart, et al., *Solid Phase Peptide Synthesis* (2nd ed., Pierce Chem. Co., Rockford, Ill. (1984)), the teachings of which are hereby incorporated by reference.

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for us as solid supports are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

The acid form of the peptides of the present invention may be prepared by the solid phase peptide synthesis procedure using a benzyl ester resin as a solid support. The corresponding amides may be produced by using benzhydrylamine or methylbenz-hydrylamine resin as the solid support. Those skilled in the art will recognize that when the BHA or MBHA resin is used, treatment with anhydrous hydrofluoric acid to cleave the polypeptide from the solid support produces a polypeptide having a terminal amide group.

The α-amino group of each amino acid used in the synthesis should be protected during the coupling reaction to prevent side reactions involving the reactive α-amino function. Certain amino acids also contain reactive side-chain functional groups (e.g., sulfhydryl, amino, carboxyl, hydroxyl, etc.) which must also be protected with appropriate protecting groups to prevent chemical reactions from occurring at those sites during the polypeptide synthesis. Protecting groups are well known to those of skill in the art. See, for example, *The Peptides: Analysis, Synthesis, Biology, Vol. 3: Protection of Functional Groups in Peptide Synthesis* (Gross and Meienhofer (eds.), Academic Press, N.Y. (1981)), the teachings of which are incorporated herein by reference.

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the α-amino protecting group, and must be removable after completion of the polypeptide synthesis under conditions that will not alter the structure of the polypeptide.

Illustrative examples of protecting groups for an α-amino group include, but are not limited to, the following: aromatic urethane-type groups such as, for example, fluorenylmethyloxycarbonyl (Fmoc), carbobenzoxy (Cbz), and substituted benzyloxycarbonyls including p-chlorobenzyloxycarbonyl, o-chlorobenzyloxycarbonyl, 2,4-dichlorobenzyloxycarbonyl, 2,6-dichlorobenzyloxycarbonyl, etc.; aliphatic urethane-type groups such as, for example, butyloxycarbonyl (Boc), t-amyloxycarbonyl, isopropyloxycarbonyl, 2-(p-biphenylyl)-isopropyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the α-amino protecting group used.

For the side chain amino group present in lysine (Lys), any of the protecting groups described above for the protection of the α-amino group are suitable. Moreover, other suitable protecting groups include, but are not limited to, the following: butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyl-oxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethylbenzenesulfonyl and 2,2,5,7,8-pentamethylchloroman-6-sulfonyl are the protecting group used for Arg.

The hydroxyl group on the side chains of serine (Ser), threonine (Thr) or tyrosine (Tyr) can be protected by a $C_1$–$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxyl protecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group.

The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the polypeptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology, Vol. 1: Methods of Peptide Bond Formation* (Gross and Meienhofer (eds.), Academic Press, N.Y. (1979)); and Izumiya, et al., *Synthesis of Peptides* (Maruzen Publishing Co., Ltd., (1975)), both of which are incorporated herein by reference.

Generally, synthesis of the polypeptide is commenced by first coupling the C-terminal amino acid, which is protected at the Nα-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(α-[2,4-dimethoxyphenyl]-Fmoc-aminomethyl)phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Nova (Switzerland) or Bachem (California)). As an alternative to the stepwise addition of individual amino acids, appropriately protected peptide fragments consisting of more than one amino acid may also be coupled to the "growing" polypeptide. Selection of an appropriate coupling reagent, as explained above, is well known to those of skill in the art. It should be noted that since the fusogenic peptides of the present invention are relative short in length, this latter approach (i.e., the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride (CH$_2$Cl$_2$) or, mixtures thereof. If coupling is incomplete, the coupling reaction may be repeated before deprotection of the Nα-amino group and addition of the next amino acid. Coupling efficiency may be monitored by a number of means well known to those of skill in the art. A preferred method of monitoring coupling efficiency is by the ninhydrin reaction. Polypeptide synthesis reactions may be performed automatically using a number of commercially available peptide synthesizers (e.g., Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or, by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The fusogenic peptides can be isolated and purified from the reaction mixture by means of peptide purification well known to those of skill in the art. For example, the polypeptides may be purified using known chromatographic procedures such as reverse phase HPLC, gel permeation, ion exchange, size exclusion, affinity, partition, or countercurrent distribution.

Although the fusogenic peptides are preferably synthesized or prepared using chemical peptide synthesis techniques such as described above, it will be understood by those of ordinary skill in the art that they can also be prepared by other means including, for example, recombinant techniques. Two text books which describe suitable recombinant techniques in great detail are Sambrook, et al., *Molecular Cloning, A Laboratory Manual* (Cold Spring Harbor Publish., Cold Spring Harbor, N.Y. 2nd ed. (1989)), *Methods in Enzymology*, Vol. 152: *Guide to Molecular Cloning Techniques* (Berger and Kimmel (eds.), San Diego: Academic Press, Inc. (1987)) and Kriegler, *Gene Transfer and Expression: A Laboratory Manual* (W. H. Freeman, N.Y. (1990)), the teachings of which are incorporated herein by reference.

IV. Fusogenic Liposomes Containing Fusogenic Polymers

In another embodiment, the present invention provides a pH-sensitive fusogenic oligomer or, alternatively, a pH-sensitive fusogenic polymer. More particularly, the present invention provides a polymer having the general structure:

in which: X is a trifunctional substrate wherein at least one of the functional groups is a carboxyl group or a protected carboxyl group; Y is ethylene glycol; and "n" is an integer having a value ranging from 1 to about 30, more preferably, from 1 to about 20 and, even more preferably, from 2 to about 10.

A "trifunctional substrate," as used herein, refers to a compound that contains three functional groups, at least one of which is a carboxy group or a protected carboxyl group as it is the carboxyl group(s) which imparts pH-sensitivity to the polymer. Examples of trifunctional substrates suitable for use in accordance with the present invention include, but are not limited to, compounds containing at least one carboxyl group and, in addition, one or more of the following: an amino group, a hydroxy group, a ketone, an aldehyde, a thiol, a functional group which allows for further chain extension or derivatization, or a combination of these various functional groups. In a presently preferred embodiment, L-glutamic acid is the trifunctional substrate used.

"Ethylene glycol," as used herein, generally refers to a compounds having the formula: (CH$_2$OH.CH$_2$OH)$_n$, wherein n has a value ranging from 1 to about 8. Examples of ethylene glycols which are suitable for use in accordance with the present invention include, but are not limited to, di(ethylene glycol), tri(ethylene glycol), tetra(ethylene glycol), penta(ethylene glycol), hexa(ethylene glycol), octa(ethylene glycol) etc. Such ethylene glycols are commercially available from a number of different sources including, for example, Aldrich Chemical Co. (Milwaukee, Wis.). In a presently preferred embodiment, tetraethylene glycol (TEG) is the ethylene glycol used.

In another embodiment, the present invention provides a polymer having the general structure:

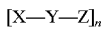

in which: X and Z are independently selected and are trifunctional substrates wherein at least one of the functional groups is a carboxyl group or a protected carboxyl group; Y is an ethylene glycol; and "n" is an integer having a value ranging from 1 to about 30, more preferably, from 1 to about 20 and, even more preferably, from 2 to about 10. The term "independently selected" is used herein to indicate that the trifunctional substrates, i.e., X and Z, may be identical or different (e.g., X and Y may both be L-glutamic acid, etc.) The trifunctional substrate and the ethylene glycol used to form the above pH-sensitive fusogenic oligomer are as defined above.

Figure 51:
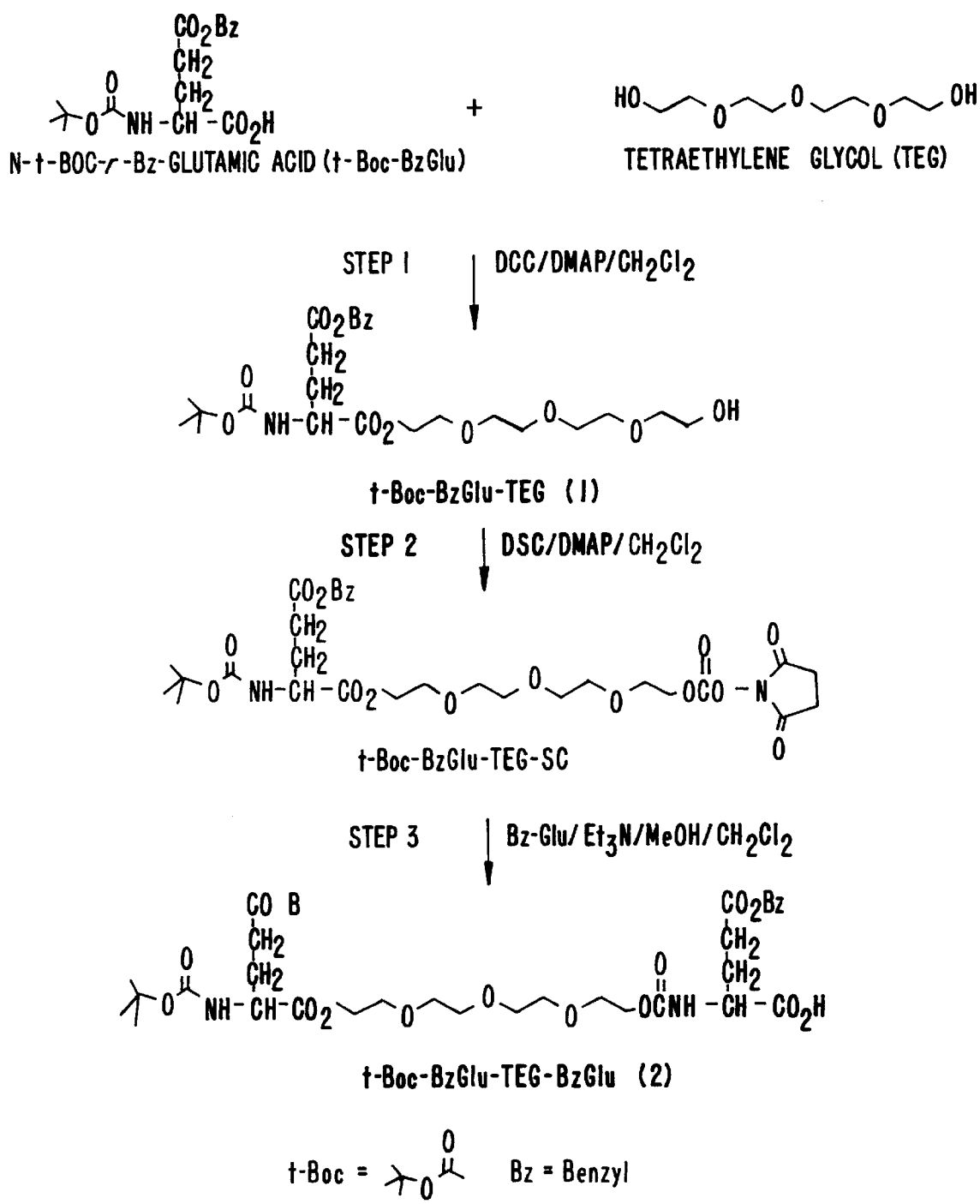
FIG. 51 illustrates a reaction scheme which can be used to synthesize the basic units for preparing glutamic acid-tetraethylene glycol oligomers.
Figure 52:
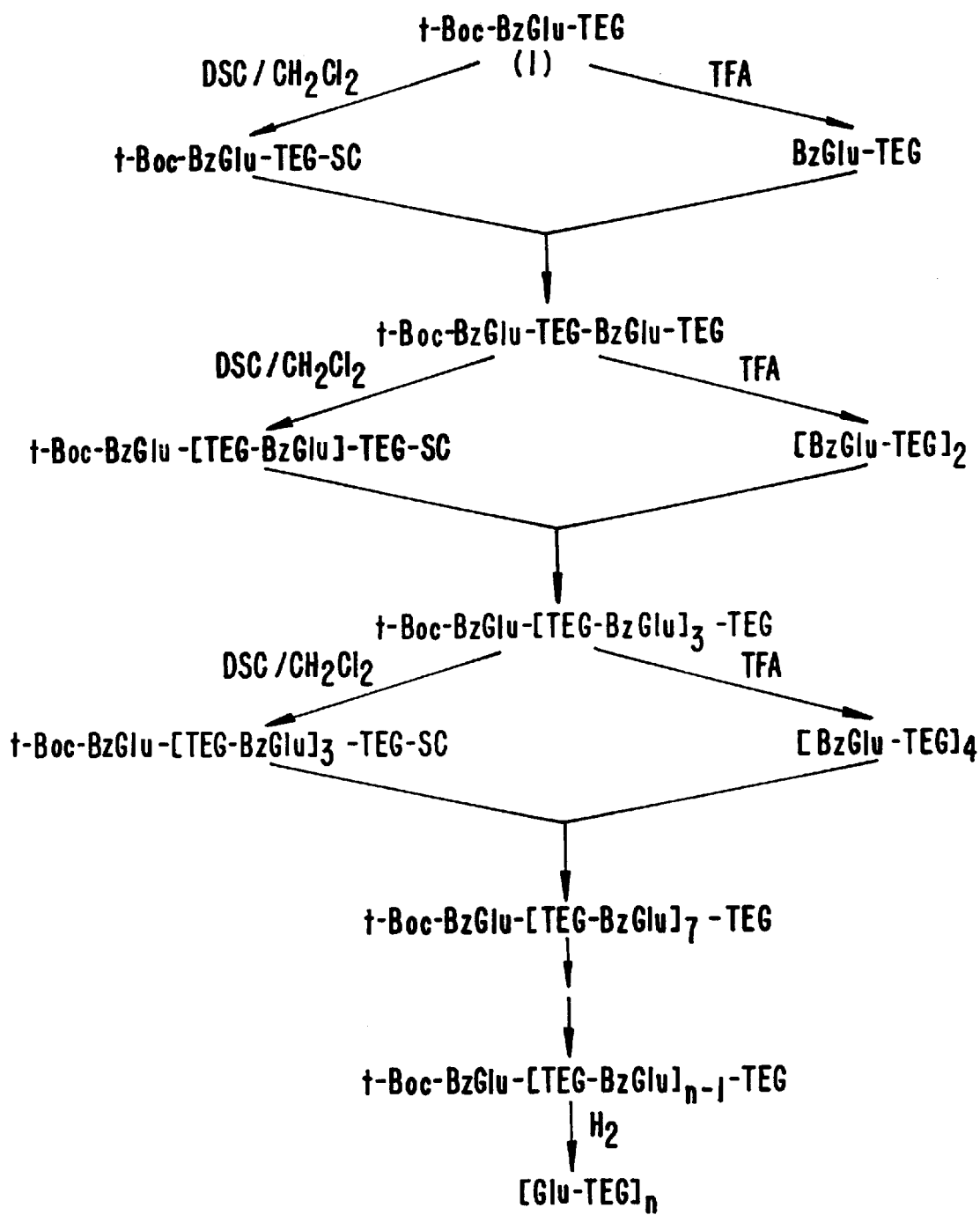
FIG. 52 illustrates the synthetic sequence for the chain extension to prepare the oligomer $[\text{Glu-TEG}]_n$.
Figure 53:
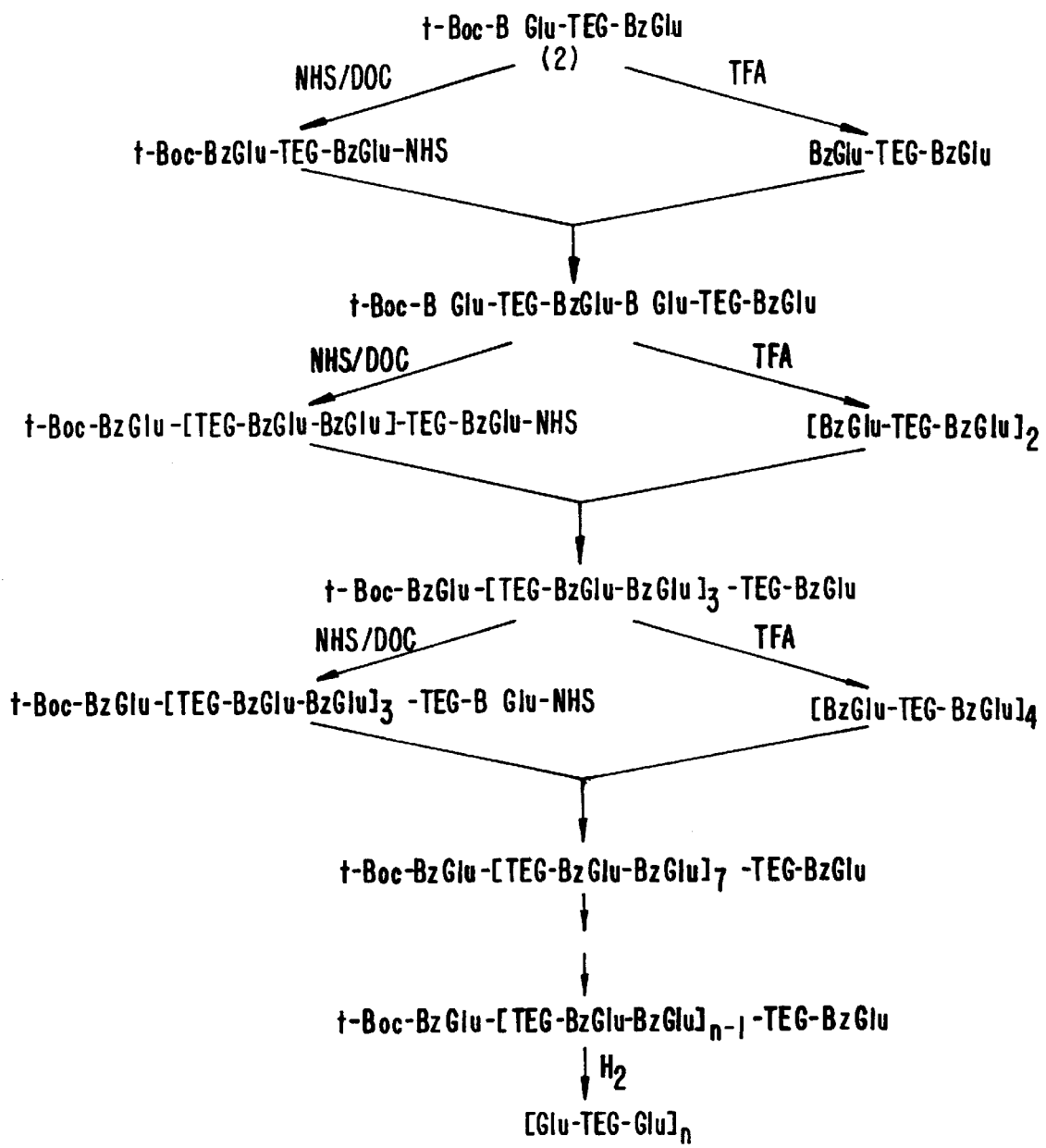
FIG. 53 illustrates the synthetic sequence for the chain extension to prepare the oligomer $[\text{Glu-TEG-Glu}]_n$.

FIGS. 51 through 53 illustrate the synthetic schemes which can be used to form the linkage of different combinations of a trifunctional substrate (e.g., L-glutamic acid (Glu)) and a short chain polyoxyethylene of uniform size (e.g., tetraethylene glycol (TEG)) to form a linear chain of defined length. FIG. 51 illustrates the reaction steps used to prepare the basic units for synthesizing glutamic acid-tetraethylene glycol oligomers. Tetraethylene glycol (TEG) is condensed with N-t-Boc-τ-Bz-L-glutamic acid by dicyclohexylcarbodiimide (DCC)/4-dimethylaminopyridine (DMAP) to form the first basic building unit: t-Boc-BzGlu-TEG (1). Activation of the latter with excess di(N-succinimidyl) carbonate (DSC) in the presence of DMAP (Step 2) enables the subsequent conjugation with BzGlu (Step 3) to form the second basic unit: t-Boc-Bz-Glu-TEG-BzGlu (2).

As shown in FIG. 52, the first basic monomeric unit (1) can be used to generate the oligomer with the structure [Glu-TEG]$_n$ (n=any number), whereas the second basic unit (2) can be used to generate the oligomer with the structure [Glu-TEG-Glu]$_n$ (n=any number) shown in FIG. 53. It should be noted that in both sequences, doubling of the chain length can be performed in one reaction and this can be repeated according to the fmal size of the oligomer required in order to provide the desired properties and characteristic when applied to the transmembrane carrier system. Therefore, the number of steps to obtain a long chain is reduced significantly. Furthermore, the fusogenic oligomers of the present invention are designed such that they can be readily conjugated to a lipid anchor at one terminal end and/or to a targeting ligand or other factor at the other terminal.

Once formed, the pH-sensitive fusogenic polymers of the present invention can be incorporated into or covalently attached to liposome vesicles, lipid particles or other lipid carrier systems using methods known to and used by those of skill in the art. Lipids which can be used to form the lipid carrier systems containing the pH-sensitive fusogenic oligomers of the present invention include phosglycerides and sphingolipids. Representative examples of suitable phosglycerides and sphingolipids are set forth in the Glossary Section, supra.

The pH-sensitive fusogenic polymers of the present invention trigger fusion or release of the contents of the carrier system on protonation of the carboxyl groups when the carrier system encounters an acidic environment. One of the advantages of the fusogenic polymers of the present invention is that they are of defined chain-lengths and, thus, one can readily control their pH-sensitivity. This is in contrast to previously used polymers which usually contain a mixture of different chain-lengths. As a result of the varying chain-lengths, the number of carboxyl groups introduced often varies between different preparations and, unfortunately, such variance causes fluctuation in the properties of the resulting systems and inconsistency in the product. Again, in contrast to such polymers, the pH-sensitive fusogenic polymers of the present invention are of a defined size, i.e., a defined chain-length.

V. Methods of Preparing Liposomes

A variety of methods are available for preparing liposomes as described in, e.g., Szoka, et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta,* 443:629–634 (1976); Fraley, et al., *Proc. Natl. Acad. Sci. USA,* 76:3348–3352 (1979); Hope, et al., *Biochim. Biophys. Acta,* 812:55–65 (1985); Mayer, et al., *Biochim. Biophys. Acta,* 858:161–168 (1986); Williams, et al., *Proc. Natl. Acad. Sci. USA,* 85:242–246 (1988); the text *Liposomes*, (Marc J. Ostro (ed.), Marcel Dekker, Inc., New York, 1983, Chapter 1); and Hope, et al., *Chem. Phys. Lip.,* 40:89 (1986), all of which are incorporated herein by reference. Suitable methods include, for example, sonication, extrusion, high pressure/homogenization, microfluidization, detergent dialysis, calcium-induced fusion of small liposome vesicles and ether-fusion methods, all of which are well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

Unilamellar vesicles are generally prepared by sonication or extrusion. Sonication is generally preformed with a tip sonifier, such as a Branson tip sonifier, in an ice bath. Typically, the suspension is subjected to several sonication cycles. Extrusion can be carried out by biomembrane extruders, such as the Lipex Biomembrane Extruder. Defined pore size in the extrusion filters can generate unilamellar liposomal vesicles of specific sizes. The liposomes can also be formed by extrusion through an asymmetric ceramic filter, such as a Ceraflow Microfilter, commercially available from the Norton Company, Worcester Mass.

Following liposome preparation, the liposomes may be sized to achieve a desired size range and relatively narrow distribution of liposome sizes. A size range of about 0.05 microns to about 0.20 microns allows the liposome suspension to be sterilized by filtration through a conventional filter, typically a 0.22 micron filter. The filter sterilization method can be carried out on a high through-put basis if the liposomes have been sized down to about 0.05 microns to about 0.20 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both of these methods, the particle size distribution can be monitored by conventional laser-beam particle size discrimination. In addition, the size of the liposomal vesicle can be determined by quasi-electric light scattering (QELS) as described in Bloomfield, *Ann. Rev. Biophys. Bioeng.* 10:421–450 (1981), incorporated herein by reference. Average liposome diameter can be reduced by sonication of formed liposomes. Intermittent sonication cycles can be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.45 microns are preferred.

For the delivery of therapeutic agents, the fusogenic liposomes of the present invention can be loaded with a therapeutic agent and administered to the subject requiring treatment. The therapeutic agents which can be administered using the fusogenic liposomes of the present invention can be any of a variety of drugs, peptides, proteins, DNA, RNA or other bioactive molecules. Moreover, cationic lipids may be used in the delivery of therapeutic genes or oligonucleotides intended to induce or to block production of some protein within the cell. Nucleic acid is negatively charged and must be combined with a positively charged entity to form a complex suitable for formulation and cellular delivery.

Cationic lipids have been used in the transfection of cells in vitro and in vivo (Wang, C-Y, Huang L., "pH sensitive immunoliposomes mediate target cell-specific delivery and controlled expression of a foreign gene in mouse," *Proc. Natl. Acad. Sci. USA,* 1987; 84:7851–7855 and Hyde, S. C., Gill, D. R., Higgins, C. F., et al., "Correction of the ion transport defect in cystic fibrosis transgenic mice by gene therapy," *Nature,* 362:250–255 (1993)). The efficiency of this transfection has often been less than desired, for various reasons. One is the tendency for cationic lipids complexed to nucleic acid to form unsatisfactory carriers. These carriers are improved by the addition of PEG-modified lipids and, in particular, PEG-modified ceramide lipids. The addition of PEG-modified lipids prevents particle aggregation and provides a means for increasing circulation lifetime and increasing the delivery of the lipid-nucleic acid particles to the target cells. Moreover, it has been found that cationic lipids fuse more readily with the target cells and, thus, the addition of neutrally charged PEG-modified ceramide lipids does not mask or diminish the positive charge of the carrier liposomes.

Cationic lipids useful in producing lipid based carriers for gene and oligonucleotide delivery include, but are not limited to, 3β-(N-(N',N'-dimethylaminoethane)carbamoyl) cholesterol (DC-Chol); N,N-distearyl-N,N-dimethylammonium bromide (DDAB); N-(1,2-dimyristyloxyprop-3-yl)-N,N-dimethyl-N-hydroxyethyl ammonium bromide (DMRIE); diheptadecylamidoglycyl spermidine (DOGS); N-(1-(2,3-dioleyloxy)propyl)-N-(2-(sperminecarboxamido)ethyl)-N,N-dimethylammonium trifluoroacetate (DOSPA); N-(1-(2,3-dioleoyloxy)propyl)-N,N,N-trimethylammonium chloride (DOTAP); N-(1-(2,3-dioleyloxy)propyl)-N,N,N-trimethylammonium chloride (DOTMA); N,N-dioleyl-N,N-dimethylammonium chloride (DODAC); LIPOFECTIN, a commercially available cationic lipid comprising DOTMA and DOPE (GIBCO/BRL, Grand Island, N.Y.) (U.S. Pat. Nos. 4,897,355; 4,946,787; and 5,208,036 issued to Epstein, et al.); LIPOFECTACE or DDAB (dimethyldioctadecyl ammonium bromide) (U.S. Pat. No. 5,279,883 issued to Rose); LIPOFECTAMINE, a commercially available cationic lipid composed of DOSPA and DOPE (GIBCO/BRL, Grand Island, N.Y.); TRANSFECTAM, a commercially available cationic lipid comprising DOGS (Promega Corp., Madison, Wis.).

Any variety of drugs which are selected to be an appropriate treatment for the disease to be treated can be administered using the fusogenic liposomes of the present invention. Often the drug will be an antineoplastic agent, such as vincristine, doxorubicin, cisplatin, bleomycin, cyclophosphamide, methotrexate, streptozotocin, and the like. It may also be desirable to deliver anti-infective agents to specific tissues by the present methods. The compositions of the present invention can also be used for the selective delivery of other drugs including, but not limited to local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-convulsants, e.g., phenytoin; antihistamines, e.g., diphenhydramine, chlorphenirimine and promethazine; antibacterial agents, e.g., gentamycin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Other particular drugs which can be selectively administered by the compositions of the present invention will be well known to those of skill in the art. Additionally, two or more therapeutic agents may be administered simultaneously if desired, where such agents produce complementary or synergistic effects.

Methods of loading conventional drugs into liposomes include an encapsulation technique and the transmembrane potential loading method. In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. Nos. 4,885,172, 5,059,421, and 5,171,578, the contents of which are incorporated herein by reference. Briefly, the transmembrane potential loading method can be used with essentially any conventional drug which exhibits weak acid or weak base characteristics. Preferably, the drug will be relatively lipophilic so that it will partition into the liposome membrane. A pH gradient is created across the bilayers of the liposomes or protein-liposome complexes, and the drug is loaded into the liposome in response to the pH gradient. The pH gradient is generated by creating a proton gradient across the membrane either by making the interior more acidic or basic than the exterior (Harrigan, et al., *Biochem. Biophys. Acta.*, 1149:329–339 (1993), the teachings of which are incorporated herein by reference), or by establishing an ion gradient employing ionizable agents, such as ammonium salts, which leads to the generation of a pH gradient (See, U.S. Pat. No. 5,316,771 (Barenholz), the teachings of which are incorporated herein by reference).

In certain embodiments of the present invention, it is desirable to target the liposomes of the invention using targeting moieties that are specific to a particular cell type, tissue, and the like. Targeting of liposomes using a variety of targeting moieties (e.g., ligands, receptors and monoclonal antibodies) has been previously described (see, e.g., U.S. Pat. Nos. 4,957,773 and 4,603,044, both of which are incorporated herein by reference).

Examples of targeting moieties include monoclonal antibodies specific to antigens associated with neoplasms, such as prostate cancer specific antigen. Tumors can also be diagnosed by detecting gene products resulting from the activation or overexpression of oncogenes, such as ras or c-erB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., *J. Biol. Chem.*, 265:16337–16342 (1990) and Leonetti, et al., *Proc. Natl. Acad. Sci. (USA)*, 87:2448–2451 (1990), both of which are incorporated herein by reference).

Targeting mechanisms generally require that the targeting agents be positioned on the surface of the liposome in such a manner that the target moieties are available for interaction with the target, for example, a cell surface receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

Following a separation step as may be necessary to remove free drug from the medium containing the liposome, the liposome suspension is brought to a desired concentration in a pharmaceutically acceptable carrier for administration to the patient or host cells. Many pharmaceutically acceptable carriers may be employed in the compositions and methods of the present invention. Suitable formulations for use in the present invention are found in *Remington's Pharmaceutical Sciences*, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135–150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

The concentration of liposomes in the carrier may vary. Generally, the concentration will be about 20–200 mg/ml, usually about 50–150 mg/ml, and most usually about 75–125 mg/ml, e.g., about 100 mg/ml. Persons of skill may vary these concentrations to optimize treatment with different liposome components or for particular patients. For example, the concentration may be increased to lower the fluid load associated with treatment.

The present invention also provides methods for introducing therapeutic compounds into cells of a host. The methods generally comprise administering to the host a fusogenic liposome containing the therapeutic compound. The host may be a variety of animals, including humans, non-human primates, avian species, equine species, bovine species, swine, lagomorpha, rodents, and the like.

The cells of the host are usually exposed to the liposomal preparations of the invention by in vivo administration of the formulations, but ex vivo exposure of the cells to the liposomes is also feasible. In vivo exposure is obtained by administration of the liposomes to host. The liposomes may be administered in many ways. These include parenteral routes of administration, such as intravenous, intramuscular, subcutaneous, and intraarterial. Generally, the liposomes will be administered intravenously or in some cases via inhalation. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel. In some instances, the liposomes may be administered orally or transdermally, although the advantages of the present invention are best realized by parenteral administration. The liposomes may also be incorporated into implantable devices for long duration release following placement.

As described above, the liposomes will generally be administered intravenously or via inhalation in the methods of the present invention. Often multiple treatments will be given to the patient. The dosage schedule of the treatments will be determined by the disease and the patient's condition. Standard treatments with therapeutic compounds that are well known in the art may serve as a guide to treatment with liposomes containing the therapeutic compounds. The duration and schedule of treatments may be varied by methods well known to those of skill, but the increased circulation time and decreased in liposome leakage will generally allow the dosages to be adjusted downward from those previously employed. The dose of liposomes of the present invention may vary depending on the clinical condition and size of the animal or patient receiving treatment. The standard dose of the therapeutic compound when not encapsulated may serve as a guide to the dose of the liposome-encapsulated compound. The dose will typically be constant over the course of treatment, although in some cases the dose may vary. Standard physiological parameters may be assessed during treatment that may be used to alter the dose of the liposomes of the invention.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and, thus, having shorter half-lives in the bloodstream. Liposomes with prolonged circulation half-lives are typically desirable for therapeutic and diagnostic uses. To maximize circulation half-lives, the bilayer stabilizing component should be a hydrophilic polymer, e.g., PEG, conjugated to lipid anchors, e.g., PEs, having long, saturated hydrocarbon chains (C18>C16>C14) as these conjugates provide a longer lasting steric barrier. As such, by varying the charge in addition to the foregoing factors, one of skill in the art can regulate the rate at which the liposomes of the present invention become fusogenic.

Additionally, the liposome suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

It will be readily apparent to those of skill in the art that various light sensitive, heat sensitive or pH-sensitive liposomes can be incorporated into the liposomes of the present invention to further enhance delivery of the therapeutic agent at the site of interest. Such liposomes and methods for triggering the release of the contents of such liposomes are described in U.S. Pat. No. 4,873,089, issued Oct. 10, 1989 to Scotto, et al., entitled PROTEOLIPOSOMES AS DRUG CARRIERS; U.S. Pat. No. 4,882,165, issued Nov. 21, 1989 to Hunt, et al, entitled LIGHT SENSITIVE LIPOSOMES; and U.S. Pat. No. 4,801,459, issued Jan. 31, 1989 to Liburdy, entitled TECHNIQUE FOR DRUG AND CHEMICAL DELIVERY, the teachings of which are incorporated herein by reference for all purposes.

For instance, U.S. Pat. No. 5,277,913 discloses a triggered release liposomal delivery system that selectively releases its contents in response to illumination or reduction in pH. The liposomes contain an amphipathic lipid, such as a phospholipid, having two chains derived from fatty acid that allow the lipid to pack into a bilayer structure. One or both of the alkyl chains contains a vinyl ether functionality that is cleaved by reactive oxygen species (ROS) or acid. A photosensitizer is incorporated into the liposomal cavity or membrane, and produces ROS or acid when illuminated to cleave the vinyl ether functionality and disrupt the liposomal membrane to release the vesicle contents. The lipid is preferably a plasmalogen, for example

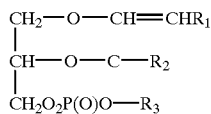

wherein $R_1$ and $R_2$ are each long chain hydrocarbons containing 12–24 carbons; and $R^3$ is a bilayer forming phosphoryl ester, such as choline, ethanolamine, serine or inositol.

Another approach involves promoting leakage of liposome contents by heating a liposomal saturated target site above a critical temperature range, for example, by radio frequency heating of target tissues. Yatvin, et al., *Science*, 202:1290 (1978). Another approach has used liposomes prepared from pH-sensitive lipids, which leak their pharmaceutical contents into low pH target regions. Such areas of localized acidity are sometimes found in tumors; hence, it has been proposed that intravenous administration of such liposomes would preferably selectively release anti-cancer chemotherapeutic agents at target tumors (see, e.g., Yatvin, et al., *Science*, 210:1253 (1980)). A pH sensitive lipid is defined herein as a lipid that undergoes a chemical or conformational change upon exposure to a decreased pH.

In addition, U.S. Pat. No. 4,882,165 similarly discloses a light-sensitive liposome which undergoes a trans to cis isomerization upon irradiation with an appropriate wavelength of light (ultraviolet light) to allow the fluid contents of the liposome to escape through the membrane into the surrounding environment. Finally, GB Patent 2,209,468 discloses liposomes having incorporated therein a photosensitizing agent that absorbs light and alters the lipid membrane to release a drug from the liposome.

Such liposomes and triggering systems can advantageously be used in combination with the liposomes of the present invention to further enhance their properties.

VI. Virosome-Mediated Intracellular Delivery of Therapeutic Agents

In another embodiment, the present invention provides virosome compositions and methods for introducing a therapeutic compound into cells of a host. Liposomes having membrane-bound viral envelope fusion protein (referred to herein as "virosomes") are employed as carriers for the therapeutic compounds. As explained in more detail below, the viral fusion protein facilitates membrane fusion between the virosome and cell membranes to release the therapeutic compound into the cell cytoplasm.

"Liposome", "vesicle" and "liposome vesicle" will be understood to indicate structures having lipid-containing membranes enclosing an aqueous interior. The structures may have one or more lipid membranes unless otherwise indicated, although generally the liposomes will have only one membrane. Such single-layered liposomes are referred to herein as "unilamellar". Multilayer liposomes are referred to herein as "multilamellar".

The virosomes present in the pharmaceutical compositions of the present invention have at least one viral fusion protein, such as influenza hemagglutinin, in the membranes of the liposomes. This structure typically requires insertion of the viral fusion protein in the liposome membrane during preparation, as generally described in Bron, et al., *Meth. Enzymol.*, 220:313–331 (1993) and Stegmann, et al., *EMBO J.*, 6:2651–2659 (1987), incorporated herein by reference. The virosomes can also be prepared from other viruses which have lipid bilayer envelopes, such as Semliki Forest virus containing the viral fusion protein E1–E2, vesicular stomatitis virus having the G protein as a membrane fusion protein, Sendai virus having the HN and F membrane fusion proteins, and others.

For preparing virosomes, the viral membrane fusion protein such as, e.g., hemagglutinin, is often purified from the corresponding virus, but it can also be produced by recombinant techniques. Purification of hemagglutinin from viral stocks is described in more detail below. Hemagglutinin from human strains of influenza A, influenza B, or influenza C, or animal (avian, swine, equine, and the like) influenza strains may be used to prepare the virosomes, although influenza A hemagglutinin is generally preferred. A wide variety of suitable virus stocks are generally available as a hemagglutinin source, such as may be available from the American Type Culture Collection (ATCC), Rockville, Md., or other sources.

Influenza virus has a lipid bilayer envelope. The virions acquire this membrane as they bud from the plasma membrane of an infected host cell. Enveloped viruses, in general, utilize membrane fusion to introduce their genome into the cytoplasm of new host cells during subsequent rounds of infection (see, e.g., White, *Ann. Rev. Physiol.*, 52:675–697 (1990)). This fusion reaction may either occur at the level of the host cell plasma membrane, or within acidic endosomes after uptake of intact virions through receptor-mediated endocytosis. During endocytic cellular infection, the target membrane for fusion of the viral envelope is the limiting membrane of the endosomal cell compartment.

Influenza membrane fusion capacity is activated only under mildly acidic conditions. Low-pH-dependent viruses, such as influenza virus, must utilize the endocytic route of cellular infection for exposure to the necessary acidic conditions, which they encounter in the lumen of the endosomes (Mellman, et al., *Ann. Rev. Biochem.*, 55:663–700 (1986)). Fusion at the plasma membrane is precluded by the strict pH dependence of their fusion activity. Infection of cells by low-pH-dependent viruses can be blocked by inhibitors of vacuolar acidification, such as chloroquine or $NH_4Cl$. In cultured cell systems influenza virus can be induced to fuse with the cell plasma membrane by a transient lowering of the pH in the extracellular medium.

The influenza virus membrane contains two major integral spike glycoproteins, hemagglutinin (HA) and neuraminidase (NA). The infectious entry of the virions into the host cell is mediated by hemagglutinin. First, HA binds to sialic-acid-containing receptors on the cell surface. Second, following the internalization of the virus particles into the endosomal cell compartment (Stegmann, et al., *Biochim. Biophys. Acta*, 904:165–170 (1987)), the HA also triggers the fusion reaction with the endosomal membrane.

The HA spike, protruding some 13.5 nm from the viral surface, is a homotrimeric molecule. Each monomer consists of two disulfide-linked subunits: HA1 (47 kD) and HA2 (28 kD), which are generated from a single polypeptide chain, HA0 (75 kD), by posttranslational cleavage by a host-cell protease. The globular HA1 domains contain the sialic-acid binding pockets. The N-terminus of HA2, generated by the post-translational cleavage of HA0, appears crucial for the expression of fusion activity of HA: Uncleaved HA0 is not fusion-active, while site-specific mutations within this region of the molecule severely affect the fusion activity of HA (Gething, et al., *J. Cell Biol.*, 102:11–23 (1986)). The N-terminus of HA2, the so-called "fusion peptide", is a conserved stretch of some 20 amino acid residues that are mostly hydrophobic in nature (White, supra). At neutral pH the fusion peptides are buried within the stem of the HA trimer about 3.5 nm from the viral surface. However, at low pH an irreversible conformational change in the HA results in their exposure (White and Wilson, *J. Cell Biol.*, 105:2887–2896 (1987)).

Influenza virus envelopes, including the hemagglutinin, can be solubilized by treatment of virus particles with a detergent. Nonionic detergents having a relatively low critical micellar concentration (CMC) are generally used to solubilize the envelope membranes. Octaethyleneglycol mono(n-dodecyl)ether ($C_{12}E_8$) and Triton X-100 may be used for solubilization, although other nonionic detergents may also be employed.

One potential disadvantage of using low-CMC detergents for solubilization and reconstitution of viral envelopes is that they can not be easily removed from the system by, e.g., dialysis. Detergents with a relatively high CMC such as N-octyl-β-D-glucopyranoside (octyl glucoside; CMC of about 20 nM), may be used to solubilize influenza virus envelopes. However, fusogenic virosomes are not readily prepared by subsequent removal of the octyl glucoside detergent. During dialysis, the hemagglutinin appears to concentrate primarily in lipid-poor aggregates with a very limited aqueous space, while the viral lipid is recovered in protein-poor vesicles. Although these vesicles exhibit some HA-mediated membrane fusion activity, only a small fraction of the HA is recovered in these vesicles (Stegmann, et al., supra).

To obtain virus for solubilization, influenza virus is grown to high titers on cultured cells (e.g., Madin-Darby Kidney cells, or MDCK) or in the allantoic cavity of 10-day-old embryonated chicken eggs. To purify the virus from the allantoic fluid the harvested allantoic fluid is centrifuged (e.g., at 1000 g for 15 min in the cold) to remove debris, after which the virus is sedimented from the supernatant (e.g., at 75,000 g for 90 min at 4°). The virus pellet is resuspended in buffer such as "HNE" (150 mM NaCl, 0.1 mM EDTA, and 5 mM HEPES, adjusted to pH 7.4) and subjected to sucrose gradient centrifugation (e.g., 10–60%, w/v, linear sucrose gradient in HNE at 100,000 g for 16 hr at 4°). The virus equilibrates as a single band at approximately 45% (w/v) sucrose. The band is collected, then frozen in small aliquots at −80°. Virus can also be purified by a one-step affinity column chromatography, which is particularly useful with virus which has been obtained from cell culture. The protein content of virus preparations can be determined according to Peterson, *Anal. Biochem.*, 83:346 (1977), incorporated herein by reference, and the phospholipid content, after quantitative extraction of the lipids from a known amount of virus, determined according to Böttcher et al., *Anal. Chim. Acta*, 24:203 (1961), incorporated herein by reference.

For solubilization of viral envelopes a detergent such as, e.g., $C_{12}E_8$ (Nikko Chemicals, Tokyo, Japan; Fluka, Buchs, Switzerland; or Calbiochem, San Diego, Calif.) is dissolved in HNE at a concentration of about 100 mM. BioBeads SM2 (Bio-Rad, Richmond, Calif.) or the like are washed with methanol and subsequently with water, according to Holloway, *Anal. Biochem.*, 55:304 (1973), incorporated herein by reference, and stored under water. Just before use the beads are drained on filter paper and weighed. Sucrose solutions for gradient centrifugation are made in HNE on a weight per volume basis.

A representative method for producing the virosomes of the invention is now described, although it will be understood that the procedure can be subjected to modifications in various aspects without affecting the outcome. As described more fully below in the experimental section, influenza virus (the equivalent of about 1.5 µmol membrane phospholipid) is diluted in HNE and sedimented (e.g., for 30 min at 50,000 g in a Beckman Ti50 rotor) at 4°. HNE buffer containing detergent is added to the pellet (e.g., 0.7 ml of 100 mM $C_{12}E_8$) and the pellet resuspended and solubilization allowed to occur for another 15 min on ice. Subsequently, the viral nucleocapsid is removed by centrifugation (e.g., for 30 min at 85,000 g at 4°) and a small sample of the supernatant can be taken at this stage for protein and phospholipid analysis. Of the initial viral protein and phospholipid, 35% (representing almost all of the membrane protein) and over 90%, respectively, may be recovered in the supernatant. The supernatant (e.g., 0.63 ml) is transferred to a 1.5-ml Eppendorf vial containing pre-washed BioBeads SM2 (e.g., 180 mg, wet weight) and the supernatant gently mixed with the beads. An additional amount of BioBeads (e.g., 90 mg wet) is added and mixing continued. The formation of vesicular structures is indicated when the suspension becomes turbid. An alternative procedure for removing the detergent from small volumes is according to Lundberg, et al., *Biochim. Biophys. Acta*, 1149:305 (1993), which is incorporated herein by reference. BioBeads are packed into a minicolumn and the preparation run through the column. A centrifugation procedure or applying negative pressure can be used to force the preparation through the column. The column procedure provides more flexibility in terms of the ratio of the amount of BioBeads used and the volume of the preparation. The virosome suspension is then centrifuged on a discontinuous sucrose gradient (e.g., 10–40% (w/v) for 90 min. at 130,000 g at 4°), and the virosomes appear as a thin opalescent band and are collected from the interface between the two sucrose-containing layers.

Other lipids can also be added to the virosome membranes during preparation. Fusion activity of the virosomes is optimally maintained when lipids similar to those of viral origin or lipid mixtures which closely resemble the lipid composition of the viral envelope are added. These lipids comprise cholesterol and phospholipids such as phosphatidylcholine (PC), sphingomyelin (SPM), phosphatidylethanolamine (PE), and phosphatidylserine (PS). However, other phospholipids may also be added. These include, but are not limited to, phosphatidylglycerol (PG), phosphatidic acid (PA), cardiolipin (CL), and phosphatidylinositol (PI), with varying fatty acyl compositions and of natural and/or (semi) synthetic origin, and dicetyl phosphate. Ceramide and various glycolipids, such as cerebrosides or gangliosides, may also be added. Cationic lipids may also be added, e.g., for concentrating nucleic acids in the virosomes and/or for facilitating virosome-mediated delivery of nucleic acids to cells. These include DOTMA, DOTAP (N-[1-(2,3-dioleoyloxy)propyl]-N,N,N-trimethylammonium chloride), DODAC (N,N-dioleyl-N,N, dimethylammonium chloride), DDAB and stearylamine or other aliphatic amines and the like. DODAC is a preferred cationic lipid for complexing nucleic acids to the virosome and the ensuing delivery of nucleic acids to cells, and is described in copending application U.S. Ser. No. 08/316,399, incorporated herein by reference. Particularly preferred concentrations of DODAC range from 25–45% (mol % of total phospholipids in the virus), more preferably 30–40%, and most preferably about 30% for the delivery of a nucleic acid such as DNA or antisense RNA to a cell. Additional lipids which may be suitable for use in the virosomes of the present invention are well known to persons of skill in the art. Nucleic acids such as oligonucleotides and DNA can also be encapsulated in virosomes after condensation with polylysine to form particles that are then enclosed within a virosome for delivery to a cell rather than being complexed to it, thereby minimizing or avoiding, if desired, the use of a cationic lipid. Furthermore, encapsulated DNA is protected from DNase degradation.

Typically, in a virosome preparation procedure involving additional lipids, the additional lipids are dried from a mixed solution in chloroform/methanol to a film at the bottom of a tube by evaporation of the solvent and subsequent exposure to vacuum for 1 h. Then the supernatant fraction obtained after solubilization of the viral envelope in detergent (e.g., $C_{12}E_8$) and sedimentation of the nucleocapsid by ultracentrifugation is added to the film. The quantities of additional lipid and supernatant are chosen such that the desired ratio of viral to additional lipid is obtained. The detergent is then removed via treatment with BioBeads or the like as described above.

Generally, the virosomes should resemble a viral envelope in structure and composition as closely as possible. The virosome preparation should generally consist of a relatively uniform population of vesicles in terms of size and protein-to-lipid ratio. Residual detergent should be minimal and not interfere with virosome function. The virosomes should mimic the biological activity of the native viral envelope. Generally, the virosomes should exhibit pH-dependent membrane fusion activity.

Virosomes can also be prepared with viral fusion proteins having different pH sensitivities, derived from, e.g., different influenza virus strains. The different pH sensitivities of the virosome can be taken advantage of to prepare virosome-liposome hybrids that encapsulate and deliver large therapeutic molecules such as DNA or proteins that may be difficult to encapsulate directly and with high efficiency in virosomes prepared according to the above protocol. A liposome is first prepared which encapsulates the therapeutic agent with high efficiency. The liposome is then fused with the virosome at the pH of the viral membrane fusion protein having the higher pH threshold for fusion. This results in a virosome-liposome hybrid containing the encapsulated therapeutic agent. The virosome-liposome hybrid is then used to deliver the encapsulated therapeutic agent to the cytosol of cells by fusion triggered at the pH of the viral fusion protein with the lower pH threshold for fusion.

The incorporation of hemagglutinin in reconstituted vesicles is readily assessed by equilibrium density-gradient analysis. The virosome preparation, collected from the discontinuous sucrose gradient, is diluted with HNE and applied to a linear sucrose gradient in HNE (e.g., 10–60% (w/v)) and the gradient centrifuged (e.g., at 170,000 g for 30 hr at 4°), after which fractions are collected and analyzed for protein and phospholipid content. The virosomes appear as a single band, containing both protein and phospholipids. The density of the virosomes will differ depending on the presence of additional lipids. In general, the density will decrease when the ratio of additional lipids to viral lipids increases.

Analysis of influenza virosomes by sodium dodecyl sulfate-polyacrylamide gel electrophoresis (SDS-PAGE) may be performed to confirm that the virosomes contain the hemagglutinin protein. The viral nucleoprotein NP, the matrix protein M1 the minor integral membrane protein of influenza virus, M2, are generally not detectable in such analysis. The virosomes have a protein-to-(phospho)lipid ratio that is similar to the ratio in the solubilization mixture after sedimentation of the nucleocapsid, but which will change when additional lipid is added to the virosome preparation.

Recovery of viral membrane protein and phospholipid in the virosome preparation ranges from 30 to 50% relative to the initially solubilized material. Residual detergent in virosomes prepared according to the above protocol is typically about 7.5 mol % relative to the total virosomal lipid. This level of detergent generally does not significantly affect the fusogenic activity of the virosomes, but residual detergent may have an effect on the capacity of the virosomes to retain low-molecular-weight encapsulated compounds.

Negative-stain electron microscopy (EM) is the most widely applied and accessible technique for assessing the structure and size of virosomes. The staining solution preferably has a neutral pH, so as to avoid acid-induced conformational changes of the hemagglutinin protein. Briefly, a droplet of the virosome suspension, after dialysis against isotonic ammonium acetate buffered to neutral pH with 5 mM HEPES, is applied to a grid with a carbon-coated Formvar film, after glow-discharge of the grid. The specimen is placed upside down for 1 min on a droplet of 2% phosphotungstic acid (PTA) at neutral pH (or, e.g., 1% sodium silicotungstate of neutral pH), drained and dried in air.

Fusion of virosomes with biological or artificial target membranes can be followed with a fluorescent resonance energy transfer assay (RET). In a convenient assay, N-(7-nitrobenz-2-oxa-1,3-diazol-4-yl)phosphatidylethanolamine (N-NBD-PE) is used as a donor probe and N-(lissamine rhodamine B sulfonyl)PE (N-Rh-PE) as the acceptor. A variant of this assay, utilizing the same donor N-NBD-PE but a different acceptor, cholesterol-anthracene-9-carboxylate (CAC), may also be used. Upon fusion of a membrane, labeled with the N-NBD-PE/N-Rh-PE pair, the two fluorophores dilute into the target membrane, resulting in a decrease of their overall surface density and a concomitant decrease of the RET efficiency. This decrease can be followed as an increase of the donor (N-NBD-PE) fluorescence. This assay can be used to assess pH-dependent fusion of influenza virosomes with a membrane, including, e.g., erythrocyte ghosts and BHK cells.

Another in vitro means to assess fusion of virosomes is an excimer assay using pyrene-labeled lipids. Pyrene fluorophores may form excited dimers (excimers) between a probe molecule in the excited state and a probe molecule in the ground state. The fluorescence emission of the excimer is shifted to higher wavelengths by about 100 nm relative to the emission of the monomer. Excimer formation is dependent on the distance between the probe molecules. Thus, coupled to one of the acyl chains of a phospholipid molecule, such as phosphatidylcholine (PC), the pyrene probe provides a sensitive measure of the surface density of the labeled molecules in a lipid bilayer membrane. On fusion of a pyrene-PC-labeled membrane with an unlabeled membrane, the pyrene-PC surface density decrease can be monitored as a reduction of the excimer fluorescence.

The RET probes N-NBD-PE/N-Rh-PE or the Pyrene-PC probe (Molecular Probes, Eugene, OR) are incorporated in the virosomal membrane as follows. The supernatant obtained after solubilization of the viral membrane and sedimentation of the nucleocapsid (see above) is added to a dry film of the probe (10 mol % with respect to the viral lipid). The mixture is lightly shaken to allow mixing of the probe with the viral lipids, and detergent is removed as described above.

Fusion of the labeled virosomes can be conveniently measured using resealed human erythrocyte ghosts as a model biological target membrane system. Alternatively, fusion activity toward liposomes can be assessed, in which case it is important to avoid liposomes consisting primarily of negatively charged phospholipids, such as cardiolipin, as these appear to support a fusion reaction with influenza virus or virosomes, whose characteristics deviate from those of fusion with biological membranes. Fusion with liposomes consisting of a 2:1 mixture of PC and PE (Avanti Polar Lipids, Alabaster, Ala.), and containing 5 mol % of the ganglioside $G_{Dta}$ or total bovine brain gangliosides (Sigma Chemical Co., St. Louis, Mo.) serving as sialic acid-containing receptors for the virus/virosomes, provides a convenient assay. Fusion may also be monitored in an on-line fashion using cultured cells as targets. Either endocytic uptake of the virosomes at neutral pH and subsequent fusion from within endosomes or direct fusion with the cell plasma membrane induced by a transient lowering of the extracellular pH may be used.

An alternative to direct assessment of the fusion activity of influenza virosomes is determining their hemolytic activity. The fusion activity of influenza virosomes, produced according to the procedure described above, typically corresponds closely to hemolytic activity, exhibiting a pH dependence identical to that of fusion. Hemolytic activity of influenza virosomes may be determined by, for example, adding the virosomes (the equivalent of 1 nmol of phospholipid, in a volume of 25 $\mu$l) to $4\times10^7$ washed human erythrocytes in 975 $\mu$l fusion buffer (135 mM NaCl, 15 mM sodium citrate, 10 mM MES, 5 mM HEPES), set to various pH values. After incubation at 37° for 30 min, the mixture is centrifuged for 3 min at 1350 g. Lysis of erythrocytes is quantified by the measurement of absorbance of the hemoglobin in the supernatant at 541 nm. Maximal hemolysis is determined after lysis of the erythrocytes in distilled water.

Additional components may be added to the virosomes to target the virosomes to specific cell types. For example, the virosomes can be conjugated to monoclonal antibodies that bind to epitopes present only on specific cell types. For example, monoclonal antibodies may bind specifically to cancer-related antigens providing a means for targeting the virosomes following systemic administration. Alternatively, ligands that bind surface receptors of the target cell types may also be bound to the virosomes. Other means for targeting liposomes may also be employed in the present invention.

The fusogenic virosomes are employed to carry therapeutic compounds for introduction into cells. As used herein, "therapeutic compound" is meant to indicate a synthetic compound suitable for therapeutic use. "Therapeutic compound" is meant to include, e.g., nucleic acids (antisense, DNA), proteins, peptides, oncolytics, anti-infectives, anxiolytics, psychotropics, ionotropes, toxins such as gelonin and inhibitors of eucaryotic protein synthesis, and the like. "Synthetic compounds" are compounds that are not naturally occurring or compounds that are isolated from the environment in which they naturally occur.

The therapeutic compound may be carried in the aqueous interior of the virosome or in the lipid membrane of the virosome. A variety of therapeutic compounds may be carried in the virosomes of the present invention. The virosomes provide a means for facilitated entry of the therapeutic compounds into the cells.

Particularly useful is encapsulation of therapeutic compounds that are active within the cytoplasm of host cells. Such compounds include, e.g., DNA encoding proteins or peptides operably linked to a promoter active in the host cell, RNA encoding a protein or peptide, nucleic acids such as antisense oligonucleotides (as described in, e.g., WO 93/09813 and WO 93/01286, both incorporated herein by reference) and ribozymes (e.g., U.S. Pat. Nos. 4,987,071, 5,254,678, and WO 94/26877, each incorporated herein by reference), oncolytic agents, anti-inflammatory agents, cardiovascular agents, anti-infective agents, psychotropic agents, and the like. The therapeutic compounds are delivered into the host cell cytoplasm upon fusion of the virosome with the endosome or plasma membrane.

The therapeutic compounds will generally be foreign to the host. By "foreign," it is meant a compound that is not naturally present in the host. Alternatively, the therapeutic compound may not be foreign to the host. The compound may naturally occur within the host. For example, nucleic acids encoding a naturally occurring protein may be introduced into host cells to increase expression of the protein in the cells. The nucleic acid can be either DNA or RNA. For expression, the nucleic acid will typically comprise at least the following operably linked elements: a transcriptional promoter, a gene encoding the desired therapeutic protein, and a transcriptional terminator.

Therapeutic compounds may be incorporated into the virosome at the time of virosome preparation. Typically, the therapeutic compound is added to the lipid/hemagglutinin-containing solution following removal of the nucleocapsid. Alternatively, the therapeutic compound is encapsulated in a virosome-liposome hybrid by initial encapsulation of the compound in a liposome, followed by fusion of the liposome with a virosome containing two hemagglutinins with different pH thresholds for fusion, as outlined above.

For administration to host cells the virosomes are carried in a pharmaceutically acceptable carrier. Many pharmaceutically acceptable carriers may be employed in the compositions of the present invention. Generally, normal buffered saline (135–150 mM NaCl) will be employed as the pharmaceutically acceptable carrier, but other suitable carriers will suffice. These compositions may be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of virosomes in the carrier may vary. Generally, the concentration will be about 20–200 mg/ml, usually about 50–150 mg/ml, and most usually about 75–125 mg/ml, e.g., about 100 mg/ml. Persons of skill may vary these concentrations to optimize treatment with different virosome components or for particular patients. For example, the concentration may be increased to lower the fluid load associated with treatment. This may be particularly desirable in patients having atherosclerosis-associated congestive heart failure or severe hypertension.

The present invention also provides methods for introducing therapeutic compounds into cells of a host. The methods generally comprise contacting the cells of the host with a virosome containing the therapeutic compound, wherein the virosome has a membrane and an aqueous interior, and a viral membrane fusion protein, e.g., influenza hemagglutinin, is contained in the membrane. The host may be a variety of animals, including humans, non-human primates, avian species, equine species, bovine species, swine, lagomorpha, rodents, and the like.

The cells may be contacted by in vivo administration of the virosomes or ex vivo contacting of the virosomes to the cells. In vivo contact is obtained by administration of the virosomes to host. The virosomes may be administered in many ways. These include parenteral routes of administration, such as intravenous, intramuscular, subcutaneous, and intraarterial. Generally, the virosomes will be administered intravenously or via inhalation. Often, the virosomes will be administered into a large central vein, such as the superior vena cava or inferior vena cava, to allow highly concentrated solutions to be administered into large volume and flow vessels. The virosomes may be administered intraarterially following vascular procedures to deliver a high concentration directly to an affected vessel. The virosomes may also be administered topically. In some instances, the virosomes may be administered orally or transdermally. The virosomes may also be incorporated into implantable devices for long term release following placement.

As described above, the virosomes are typically administered intravenously or via inhalation in the methods of the present invention. Often multiple treatments will be given to the patient. The dosage schedule of the treatments will be determined by the disease and the patient's condition. Standard treatments with therapeutic compounds that are well known in the art may serve as a guide to treatment with virosomes containing the therapeutic compounds. The duration and schedule of treatments may be varied by methods well known to those of skill.

The dose of virosomes of the present invention may vary depending on the clinical condition and size of the animal or patient receiving treatment. The standard dose of the therapeutic compound when not encapsulated may serve as a guide to the dose of the virosome-encapsulated compound. The dose will typically be constant over the course of treatment, although the dose may vary in some instances. Standard physiological parameters may be assessed during treatment that may alter the dose of the virosomes.

VII. EXAMPLES

A. Examples Relating to Fusogenic Liposomes Containing Bilayer Stabilizing Components

1. MATERIALS AND GENERAL METHODS a. Materials

All phospholipids including fluorescent probes and PEG-PE conjugates were purchased from Avanti Polar Lipids, Birmingham, Ala., USA. 1-O-methyl-(poly(ethoxy)-O-succinyl-O-(egg)ceramide which was a gift from Dr L. Choi of Inex Pharmaceuticals Corp., Vancouver, BC, Canada. Di-[1-$^{14}$C]-palmitoylphosphatidyl-choline was purchased from DuPont, Mississuaga, Ont., Canada. [$^{3}$H]-DSPE-PEG$_{2000}$ was synthesized as described previously (Parr, et al., *Biochim. Biophys. Acta*, 1195: 21–30 (1994)). Other reagents were purchased from Sigma Chemical Co., St Louis, Mo., USA.

b. Preparation of Multilamellar Vesicles and Large Unilamellar Vesicles

Lipid components were mixed in 1–2 ml of benzene:methanol (95:5, v/v) and then lyophilized for a minimum of 5 hours at a pressure of <60 millitorr using a Virtis lyophilizer equipped with a liquid N$_2$ trap. Multilamellar vesicles (MLVs) were prepared by hydrating the dry lipid mixtures in 150 mM NaCl, buffered with 10 mM Hepes-NaOH, pH 7.4 (Hepes-buffered saline, HBS). Mixtures were vortexed to assist hydration. To produce large unilamellar vesicles (LUVs), MLVs were first frozen in liquid nitrogen and then thawed at 30° C. five times. LUVs were produced by extrusion of the frozen and thawed MLVs ten times through 2 stacked polycarbonate filters of 100 nm pore size at 30° C. and pressures of 200–500 psi (Hope, et al., *Biochim. Biophys. Acta*, 812:55–65 (1985)).

c. $^{31}$P-NMR Spectroscopy $^{31}$P-NMR spectra were obtained using a temperature controlled Bruker MSL200 spectrometer operating at 81 MHz. Free induction decays were accumulated for 2000 transients using a 4 µs, 90° pulse, 1 sec. interpulse delay, 20 KHz sweep width and Waltz decoupling. A 50 Hz line broadening was applied to the data prior to Fourier transformation. Samples were allowed to equilibrate at the indicated temperature for 30 minutes prior to data accumulation. Lipid concentrations of 30–70 mM were used.

d. Freeze-fracture Electron Microscopy

MLVs were prepared by hydrating a mixture of DOPE:cholesterol:DOPE-PEG$_{2000}$ (1:1:0:1) with HBS. A portion of the mixture was extruded as described above to produce LUVs. Glycerol was added to both MLVs and LUVs to a fmal concentration of 25% and samples were rapidly frozen in liquid freon. The samples were fractured at −110° C. and <10$^{-6}$ torr in a Balzers BAF400 unit. Replicas were prepared by shadowing at 45° with a 2 nm layer of platinum and coating at 90° with a 20 nm layer of carbon. The replicas were cleaned by soaking in hypochlorite solution for up to 48 hrs and were visualized in a Jeol JEM-1200 EX electron microscope.

e. Gel Filtration of LUVs and Micelles

LUVs composed of DOPE:cholesterol:DSPE-PEG$_{2000}$ (1:1:0:1) with trace amounts of $^{14}$C-DPPC and $^{3}$H-DSPE-PEG$_{2000}$ were chromatographed at a flow rate of approximately 0.5 ml/min on a column of Sepharose CL-4B was pretreated with 10 mg of eggPC, which had been suspended in HBS by bath sonication, to eliminate non-specific adsorption of lipid to the column. Micelles were prepared by hydrating DSPE-PEG$_{2000}$ containing a trace amount of $^{3}$H-DSPE-PEG$_{2000}$ with HBS and chromatographed as described for LUVs.

f. Lipid Mixing Assays

Lipid mixtures were prepared as described for NMR measurements. The resultant multilamellar vesicles (MLV) were frozen in liquid nitrogen and then thawed at 30° C. five times. Large unilamellar vesicles (LUV) were produced by extrusion of the frozen and thawed MLV ten times through 2 stacked polycarbonate filters of 100 mn pore size at 30° C. and pressures of 200–500 psi (Hope, et al., *Biochim. Biophys. Acta*, 812:55–65 (1985)).

Lipid mixing was measured by a modification of the fluorescence resonance energy transfer (FRET) assay of Struck, et al. (*Biochemistry*, 20:4093–4099 (1981)). LUVs were prepared containing the fluorescent lipids, N-(7-nitro-2-1,3-benzoxadiazol-4-yl)- dioleoylphosphatidylethanolamine (NBD-PE) and N-(lissamine rhodamine B sulfonyl)-dipalmitoylphosphatidylethanolamine (Rh-PE) at 0.5 mol %. LUVs (50–60 $\mu$M) and a three-fold excess of unlabelled target vesicles were mixed in the fluorimeter at 37° C. for short term assays ($\leq$1 hour), or in sealed cuvettes in a dark water bath at 37° C. for longer assays. For measurements of fusion after PEG-lipid transfer, an excess of liposomes prepared from 1-palmitoyl-2-oleoyl-phosphatidylcholine (POPC) was added as a sink for the PEG-lipid. Fluorescence emission intensity was measured at 517 nm with excitation at 465 nm both before and after the addition of Triton X-100 (final concentration of 0.5% or 1% when POPC sink was used). Data is presented as either uncorrected fluorescence intensity for short term assays ($\leq$1 hour) or as percentage fusion. Light scattering controls were performed by replacing LUVs labelled with 0.5 mol % probes with unlabelled vesicles. Maximum fusion was determined using mock fused vesicles containing 0.125 mol % of each fluorescent probe. The percentage fusion was calculated as:

$$\% \text{ Fusion} = \frac{\frac{(F_{(t)} - L_{(t)})}{(F_T - L_T)} - \frac{(F_O - L_O)}{(F_T - L_T)}}{\frac{(M_{(t)} - L_{(t)})}{(M_T - L_T)} - \frac{(F_O - L_O)}{(F_T - L_T)}} \times 100$$

where $F_{(t)}$=fluorescence intensity at time t; $F_o$=fluorescence intensity at zero time; $F_T$ =fluorescence intensity in the presence of Triton X-100. M and L represent the same measurements for the mock fused control and the light scattering control respectively. Changes in fluorescence of the mock fused control indicated that exchange of the fluorescent probes over 24 hours accounted for 10% of the fluorescence change observed, but was negligible over the first hour.

g. Fusion of Liposomes with Red Blood Cells

LUVs composed of DOPE:cholesterol:DODAC (40:45.15) or DOPE:cholesterol:DODAC:PEG-ceramide (35:45:15:) were prepared by standard extrusion techniques. LUVs also contained 1 mol % rhodamine-PE. LUVs (200 $\mu$M) were incubated at 37° C. with 50 $\mu$l packed RBCs in a fmal volume of 1 ml. For assays of fusion after PEG-lipid exchange, a sink of 2 mM POPC:cholesterol (55:45) was included. In some assays, the fusogenic liposomes were pre-incubated with the sink before being mixed with the RBCs (See, figure legends for FIGS. 22–24). Aliquots of the mixtures were transferred to glass microscope slides, covered with cover slips and examined by phase contrast and fluorescent microscopy. Fusion was assessed as fluorescent labeling of the RBC plasma membranes. For FIGS. 22–24, fluorescent liposomes were incubated with POPC:cholesterol liposomes and/or RBCs as described in section "L," infra. Panels a,c and e of FIGS. 22–24 are views under phase contrast, whereas panels b,d and f of FIGS. 22–24 are the same fields viewed under fluorescent light.

h. Other Procedures

Phospholipid concentrations were determined by assaying for phosphate using the method of Fiske and Subbarow (*J. Biol. Chem.*, 66:375–400 (1925)). Liposome size distributions were determined by quasi-elastic light scattering (QELS) using a Nicomp model 370 particle sizer.

2. Experimental Findings a. Influence of BSC on the Polymorphic Phase Properties of an Equimolar Mixture of DOPE and Cholesterol $^{31}$P-NMR was used to examine the effect of bilayer stabilizing component (BSC), in this instance poly-(ethyleneglycol)$_{2000}$ conjugated to DOPE (i.e., DOPE-PEG$_{2000}$), on the phase preference of an equimolar mixture of DOPE and cholesterol (FIG. 1). In the absence of BSC, the mixture adopted an inverse hexagonal phase (H$_{II}$) at 20° C. as determined from the characteristic $^{31}$P-NMR lineshape with a low field peak and high field shoulder (Cullis and deKruijff, *Biochim. Biophys. Acta* 559:399–420 (1979)). As the amount of BSC in the mixture was increased, the peak corresponding to H$_{II}$ phase phospholipid disappeared and a high field peak with a low field shoulder, characteristic of bilayer phase phospholipid (Cullis and deKruijff, supra, 1979) appeared. When DOPE-PEG$_{2000}$ was present at 20 mol % of phospholipid, the mixture was almost exclusively bilayer with no evidence of H$_{II}$ phase lipid.

Figure 2:
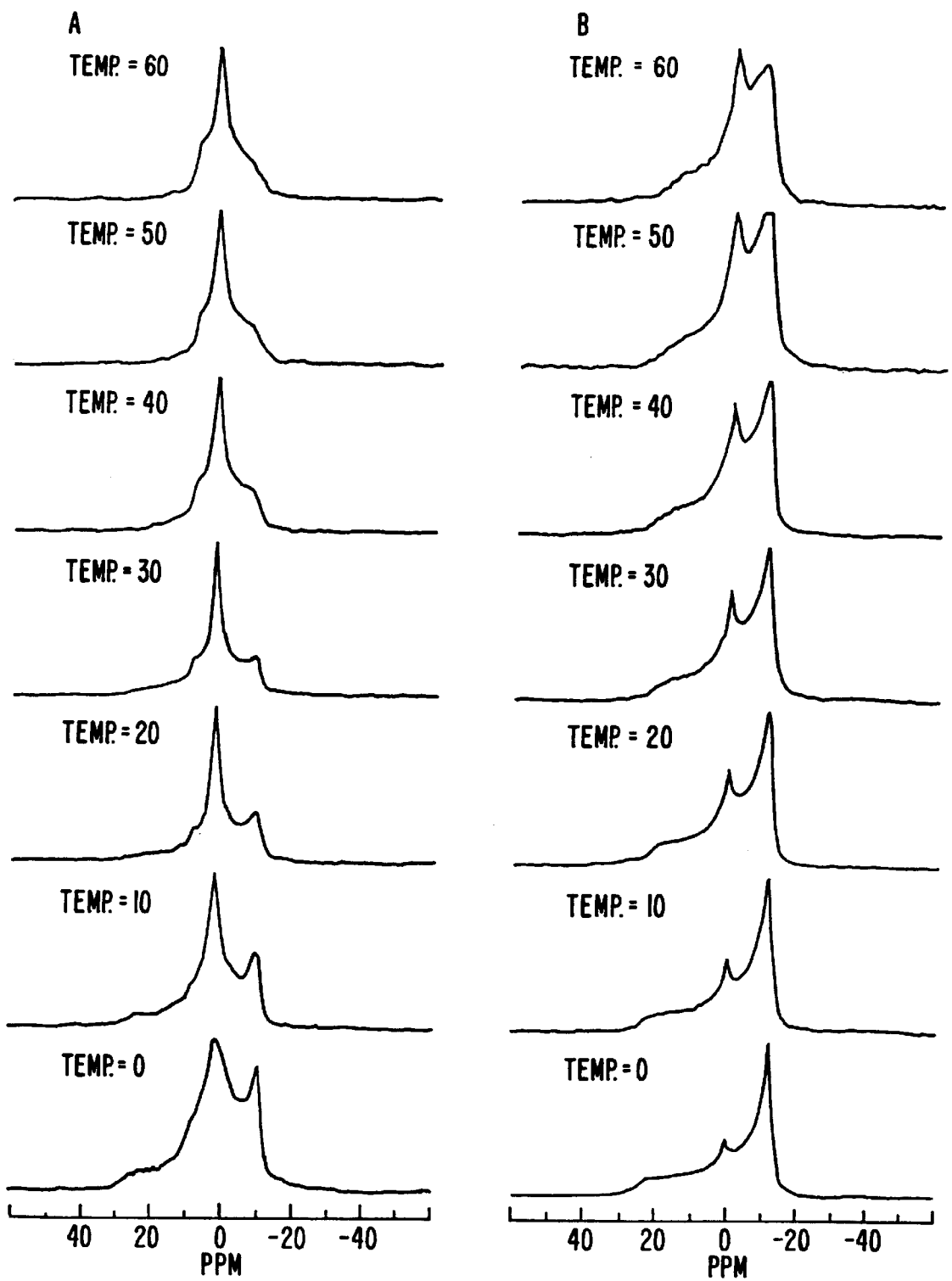
FIG. 2 illustrates the temperature dependence of bilayer stabilization by BSC. Multilamellar vesicles were prepared, as described in the examples, from mixtures of DOPE:cholesterol:DOPE-PEG$_{2000}$ at a ratio of: A, 1:1:0.1; or B, 1:1:0.25. The samples were cooled to 0° C. and $^{31}$P-NMR spectra were determined from 0° C. to 60° C. at 10° C. intervals. The samples were allowed to equilibrate at each temperature for 30 min. prior to data accumulation.

In addition to the peaks corresponding to H$_{II}$ phase and bilayer phase, a third peak indicative of isotropic motional averaging was observed in the presence of BSC (FIG. 1). The size of the isotropic signal varied with the amount of BSC present and, as shown in subsequent Figures, the nature of the BSC species. The signal was largest at concentrations of BSC that allowed H$_{II}$ and bilayer phases to co-exist and diminished when either H$_{II}$ or bilayer phase predominated. Such a signal may be produced by a number of phospholipid phases which allow isotropic motional averaging on the NMR timescale, including micellar, small vesicular, cubic and rhombic phase phospholipids.

b. The Influence of BSC on the Thermotropic Properties of an Equimolar Mixture of DOPE and Cholesterol FIG. 2 illustrates the effect of temperature on the phase properties of mixtures of DOPE, cholesterol and BSC. When DOPE-PEG$_{2000}$ was present at 9 mol %, there was a large isotropic signal which dominated the spectrum at all temperatures. The predominant, non-isotropic phase at 0° C. was bilayer. However, as the temperature was increased the high field peak diminished and a shoulder corresponding to the low field peak of the H$_{II}$, phase appeared. The apparent bilayer to hexagonal phase transition occurred at 40–50° C., but was almost obscured by the large isotropic signal. DOPE on its own exhibits a sharp transition over an interval of approximately 10° C. (see, FIG. 1 in Tilcock, et al., *Biochemistry*, 21:4596–4601 (1982)). The transition in mixtures of DOPE, cholesterol and BSC was slow in comparison with both phases present over a temperature range of almost 40° C. (See also, FIG. 3).

The mixture was stabilized in the bilayer conformation over the same temperature range when the BSC content was increased to 20 mol % (FIG. 2). There was no evidence of phospholipid in the H$_{II}$ phase. In addition, the isotropic signal was markedly reduced at the higher BSC concentration at all temperatures studied. The amount of lipid experiencing isotropic motional averaging increased as the temperature increased for both concentrations of BSC.

c. The Effect of Head Group size Sn the Bilayer Stabilizing Properties of BSCs

Figure 3:
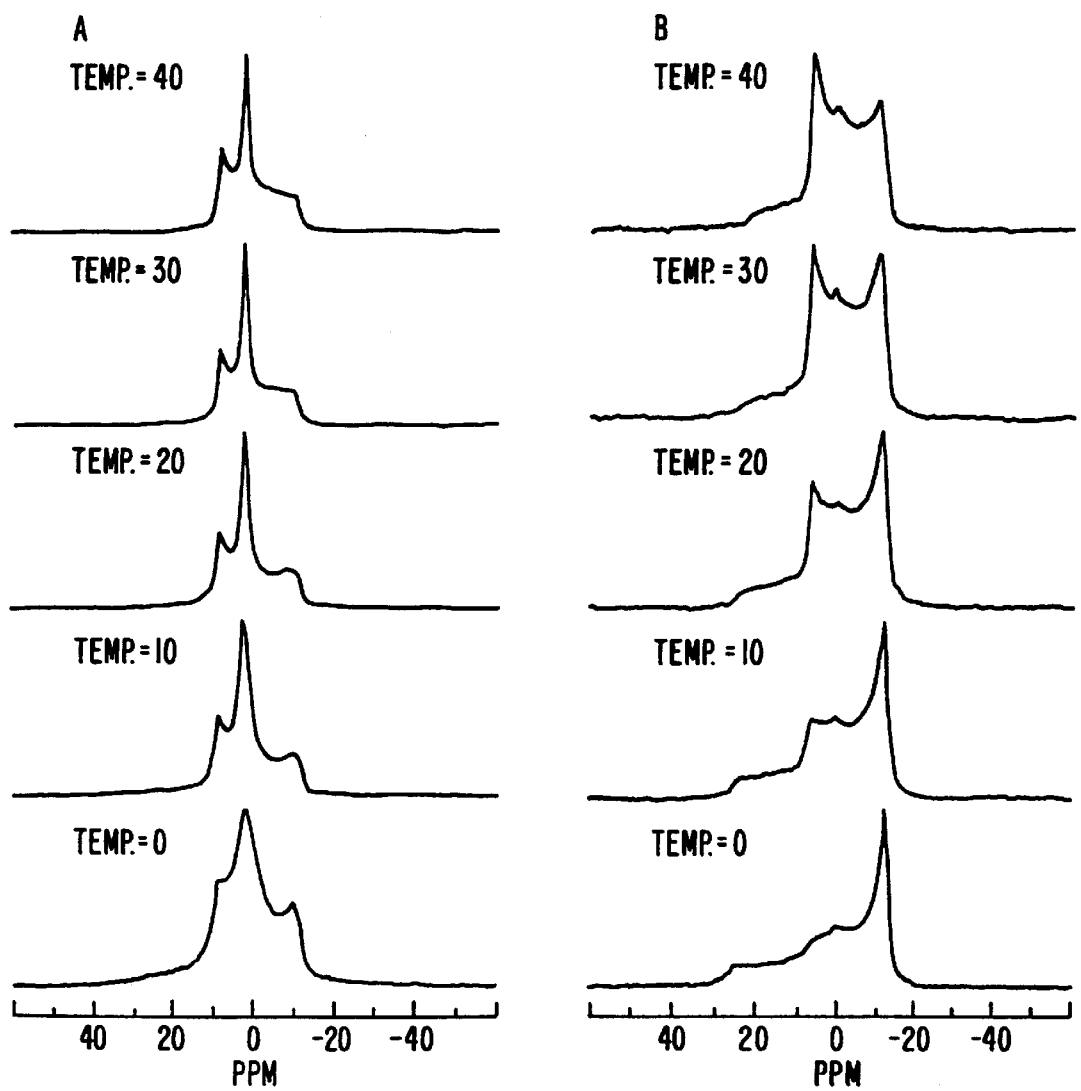
FIG. 3 illustrates the effect of headgroup size on the bilayer stabilizing ability of BSC. Multilamellar vesicles were prepared from either A, DOPE:cholesterol: DOPE-PEG$_{2000}$, 1:1:0.05, or B, DOPE:cholesterol:DOPE-PEG$_{5000}$, 1:1:0.05. Other conditions were the same as for FIG. 2.
Figure 4:
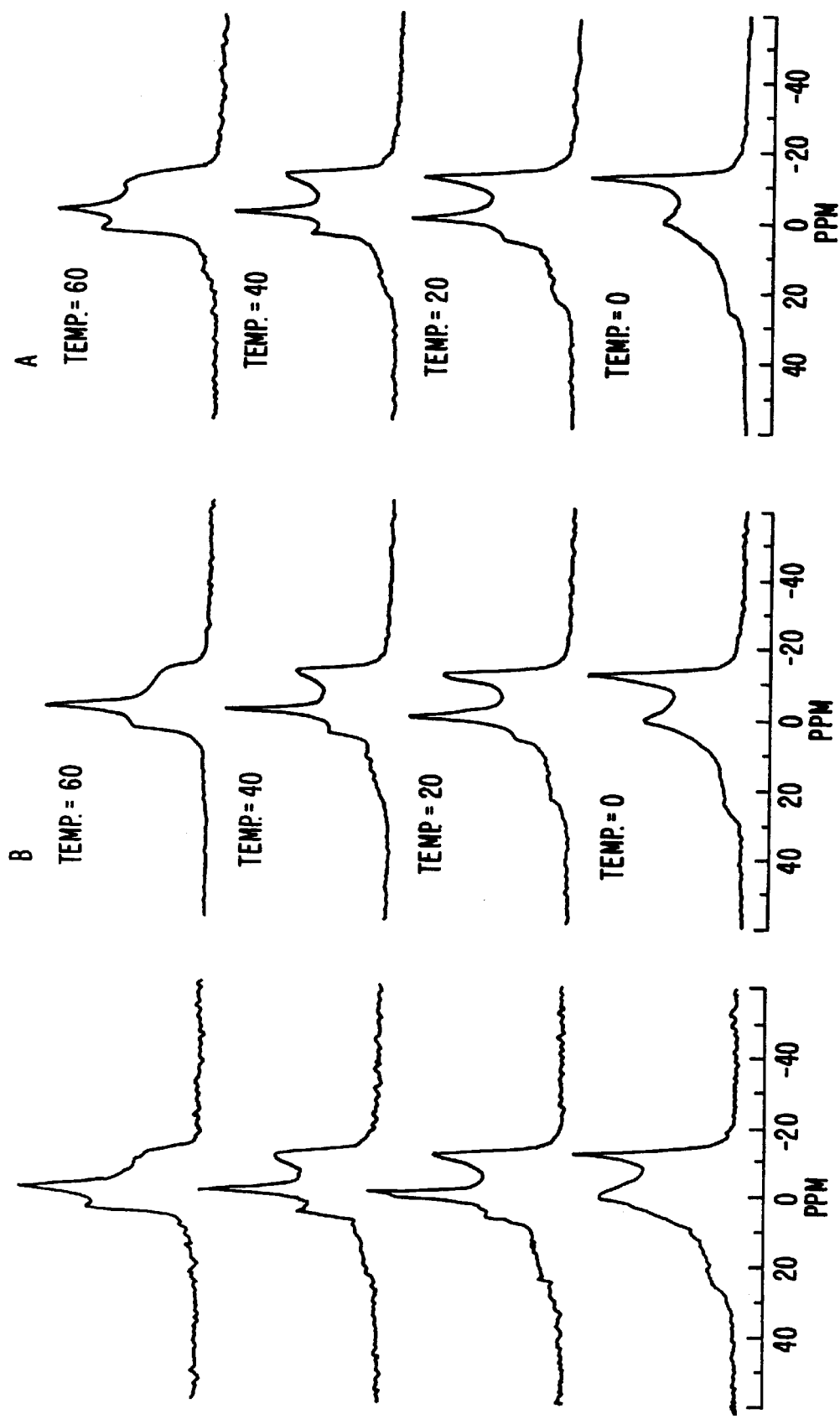
FIG. 4 illustrates the effect of the acyl chain composition on the bilayer stabilizing ability of BSC. Multilamellar vesicles were prepared, as described in the examples, from either A, DOPE:cholesterol:DMPE-PEG$_{2000}$, 1:1:0.1, B, DOPE:cholesterol:DPPE-PEG$_{2000}$, 1:1:0.1, or C, DOPE:cholesterol:DSPE-PEG$_{2000}$, 1:1:0.1. Other conditions were the same as for FIG. 2.

The influence of head group size on the bilayer stabilizing properties of BSCs is illustrated in FIG. 3. DOPE-PEG$_{2000}$ at 5 mol % had limited bilayer stabilizing ability. A broad bilayer to H$_{II}$ transition was centered at approximately 10° C., but a large proportion of the lipid adopted non-bilayer phases at all temperatures examined. Increasing the size of the headgroup by using poly-(ethyleneglycol)$_{5000}$ conjugated to DOPE (DOPE-PEG$_{5000}$) in place of DOPE-PEG$_{2000}$, at the same molar fraction, caused a marked increase in bilayer stability. The bilayer to H$_{II}$ transition temperature increased to approximately 30° C. and the isotropic signal was barely discernible. The broadening of the bilayer to H$_{II}$ transition noted above is particularly evident here with $H_{II}$ phase lipid present at 0° C. and bilayer phase lipid present at 40° C.

d. The Influence of Acyl Chain Composition on the Bilayer Stabilizing Properties of BSCs The bilayer stabilizing ability of three BSCs differing only in acyl chain composition is shown in FIG. 4. $PEG_{2000}$ conjugated to dimyristoylphosphatidyl-ethanolamine (DMPE-$PEG_{2000}$), dipalmitoylphosphatidylethanolamine (DPPE-$PEG_{2000}$) or distearoylphosphatidylethanolamine (DSPE-$PEG_{2000}$) showed a similar ability to stabilize an equimolar mixture of DOPE and cholesterol. The bilayer to $H_{II}$ phase transition was raised to approximately 40–50° C. The results are similar to those presented in FIG. 2 which were obtained using a BSC with the same headgroup, but unsaturated acyl groups (DOPE-PEG2000) at the same concentration. The size of the isotropic signal varied somewhat with the different BSCs, being smallest with DSPE-$PEG_{2000}$ and largest with DOPE-$PEG_{2000}$ (cf., FIG. 2 and FIG. 4).

e. The Use of PEG-ceramides as Bilayer Stabilizing Components

Figure 5:
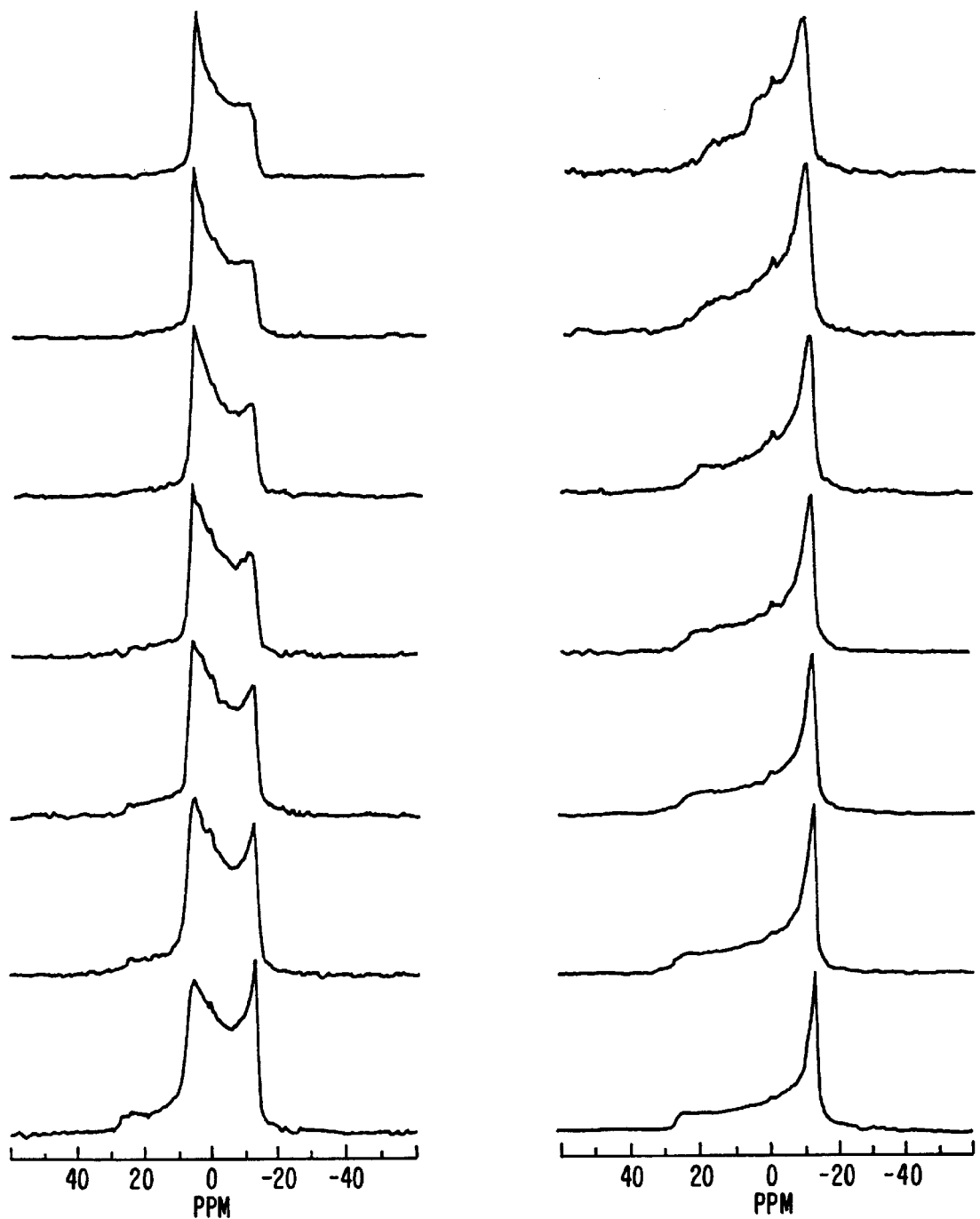
FIG. 5 illustrates the ability of PEG-Ceramide to act as a bilayer stabilizing component. Multilamellar vesicles were prepared, as described in the examples, from DOPE:cholesterol:egg ceramide-PEG$_{2000}$ at a ratio of A, 1:1:0.1 or B, 1:1:0.25. Other conditions were the same as for FIG. 2.

The spectra set forth in FIGS. 1–4 were all obtained using PEG conjugated to phosphatidylethanolamine through a carbamate linkage. In addition, however, the use of ceramide as an alternative anchor for the hydrophilic polymer was examined. $PEG_{2000}$ was conjugated via a succinate linker to egg ceramide. FIG. 5 shows the $^{31}$P-NMR spectra obtained using mixtures of DOPE:cholesterol:egg ceramide-$PEG_{2000}$ (1:1:0.1 and 1:1:0.25) over the temperature range of 0 to 60° C. At the lower molar ratio of PEG-ceramide, both bilayer and $H_{II}$ phase lipid are in evidence at most temperatures. However, at the higher PEG-ceramide molar ratio, the spectra are exclusively bilayer up to 60° C. at which point a low field shoulder corresponding to $H_{II}$ phase lipid is visible. Unlike the spectra obtained using PEG-PEs, there was almost no isotropic signal when PEG-ceramide was used.

f. Freeze-fracture Electron Microscopy

Figure 6:
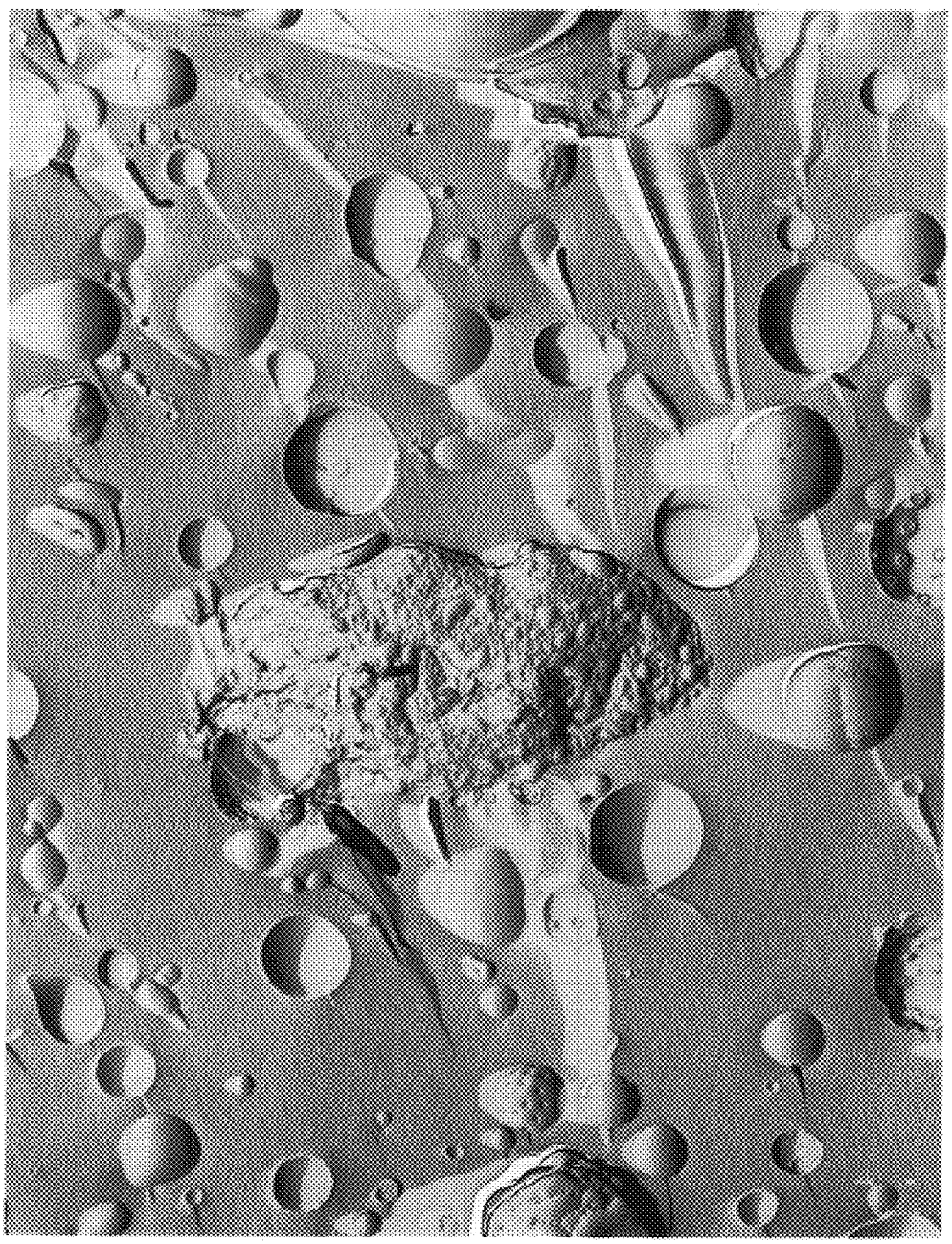
FIG. 6 illustrates the freeze-fracture electron micrograph of MLVs prepared from DOPE:cholesterol:DOPE-PEG$_{2000}$ (1:1:0.1). The samples were prepared as described in the examples. The bar represents 500 nm.

One of the interesting features of several of the NMR spectra was the narrow signal at 0 ppm, indicative of isotropic motional averaging. This signal can arise from a number of phospholipid phases such as micellar, small vesicular, cubic and rhombic phase structures. Freeze-fracture electron microscopy was used to investigate this aspect further. FIG. 6 shows an electron micrograph of MLVs prepared by hydrating a mixture of DOPE:cholesterol:DOPE-$PEG_{2000}$ (1:1:0.1) with HBS at room temperature. This lipid mixture corresponds to the NMR spectra set forth in FIG. 2A which exhibited evidence of bilayer, $H_{II}$ and isotropic phases.

A number of different structures are visible in the micrograph. Much of the lipid is present as large spherical vesicles of 400 to 600 nm in diameter. Many of the vesicles have indentations which appear to be randomly distributed in some vesicles, but organized in straight or curved lines in others. Cusp-like protrusions are also visible on the concave surfaces of some vesicles. These features are commonly referred to as lipidic particles (Verkleij, A. J., Biochim. Biophys. Acta, 779:43–92 (1984)) and may represent an intermediate structure formed during fusion of bilayers. These large vesicles would be expected to give rise to a predominantly bilayer $^{31}$P-NMR spectrum with a narrow isotropic signal due to the lipidic particles. Similar results have been observed with N-methylated PEs (Gagne, et al., Biochemistry, 24:4400–4408 (1985)). A number of smaller vesicles of around 100 nm diameter can also be seen. These vesicles may have been formed spontaneously on hydration, or may have been produced by vesiculization of larger vesicles. These vesicles are sufficiently small for lipid lateral diffusion, or tumbling of the vesicles in suspension, to produce motional averaging on the NMR timescale (Burnell, et al., Biochim. Biophys. Acta, 603:63–69 (1980)), giving rise to an isotropic signal (see, FIG. 2A). In the center of FIG. 6 is a large aggregate showing evidence of several different structures. The right side of the aggregate is characterized by what appears to be closely packed lipidic particles. The upper left hand side shows a distinct organization into three-dimensional cubic arrays and the lower left hand region has the appearance of stacked tubes characteristic of lipid adopting the $H_{II}$ phase (Hope, et al., J. Elect. Micros. Tech., 13:277–287 (1989)). This is consistent with the corresponding $^{31}$P-NMR spectrum.

Figure 7:
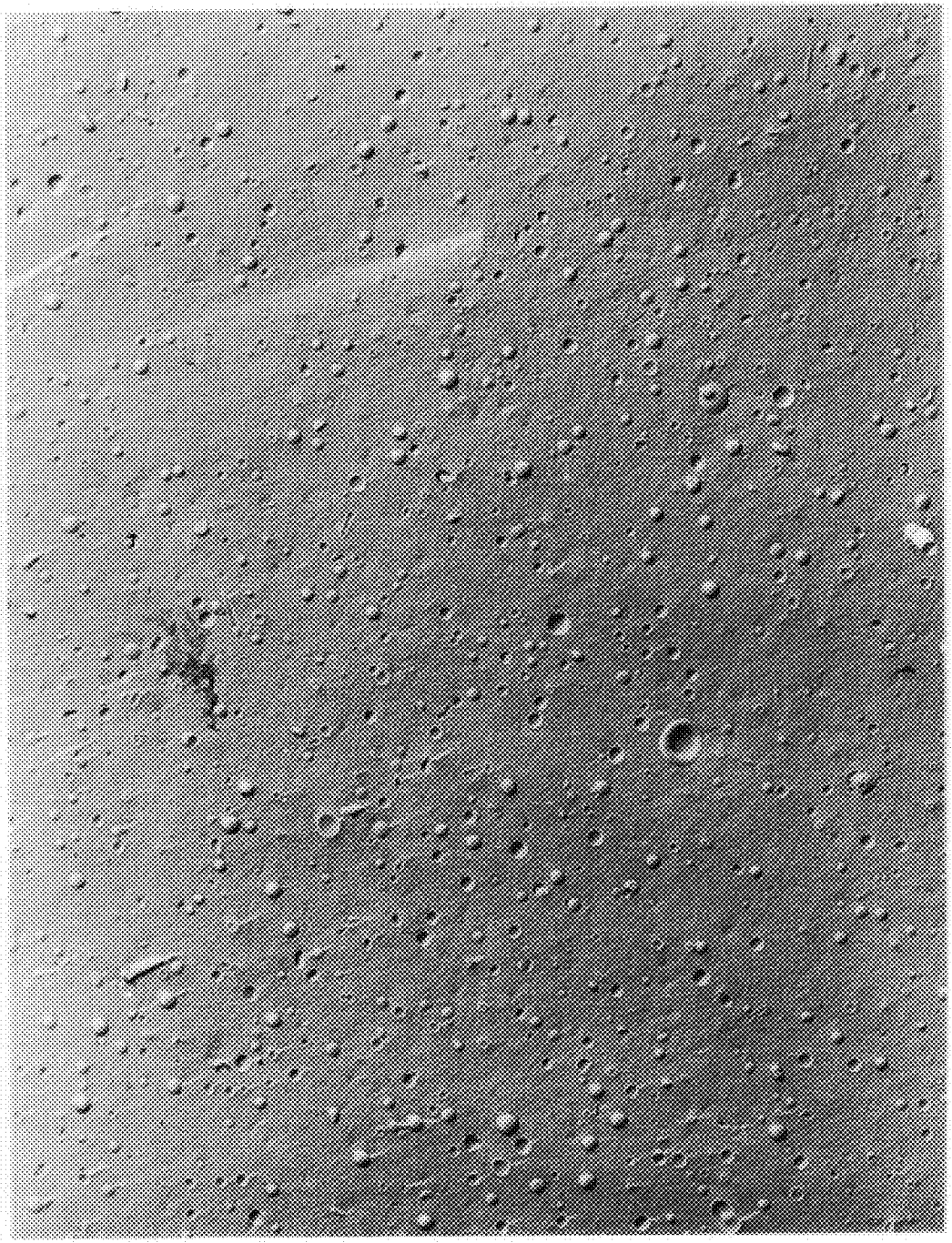
FIG. 7 illustrates the freeze-fracture electron micrograph of LUVs prepared from DOPE:cholesterol:DOPE-PEG$_{2000}$ (1:1:0.1). The samples were prepared as described in the examples. The bar represents 500 nm.

FIG. 7 shows the appearance of the same mixture after extrusion through polycarbonate filters of 100 nm pore size to produce LUVS. The lipid is predominantly organized into vesicles of approximately 100 nm in diameter. Closer inspection reveals the presence of occasional larger vesicles and some of tubular shape. Overall the fairly uniform size distribution is typical of that obtained when liposomes are produced by extrusion.

Figure 8:
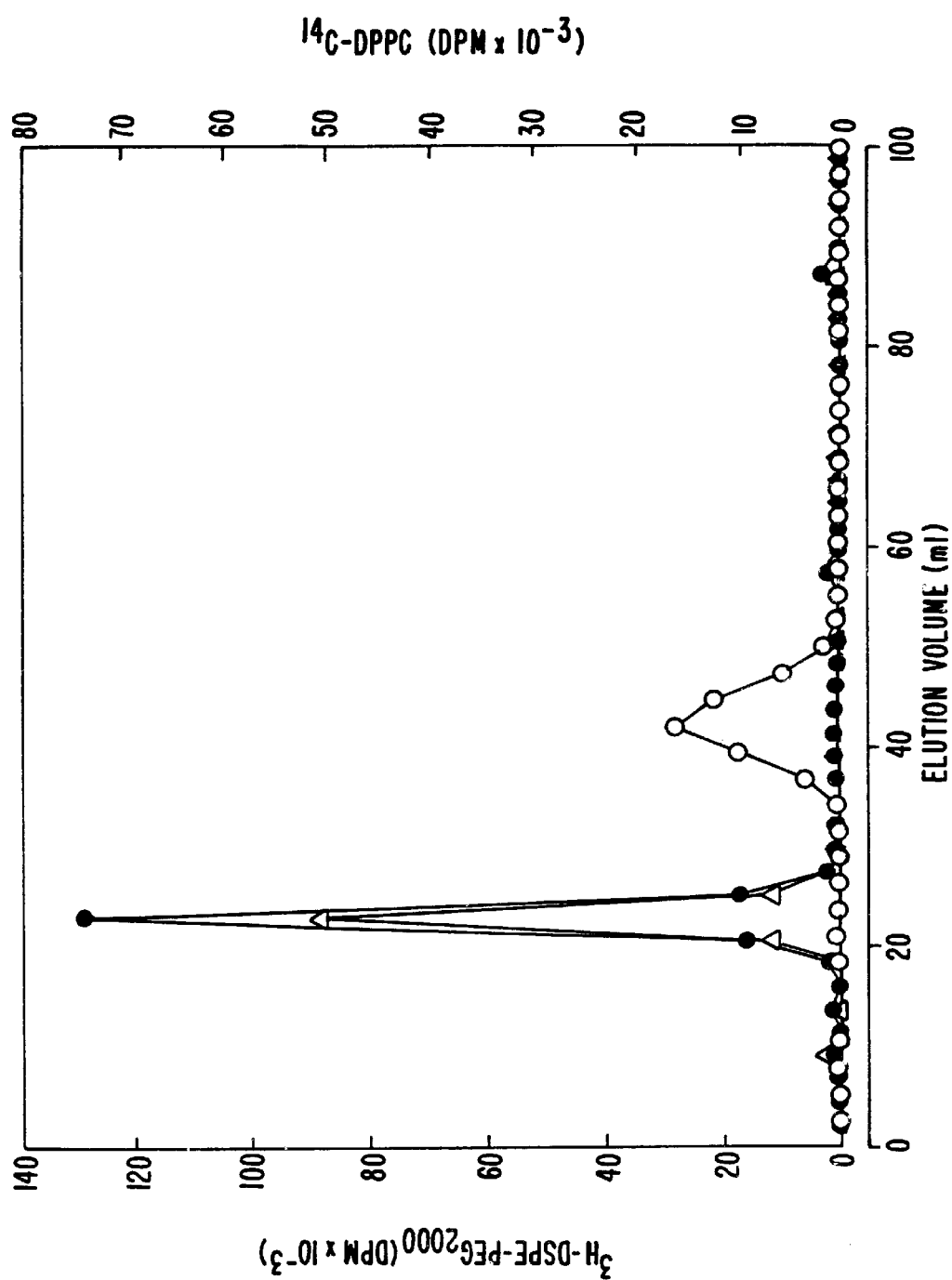
FIG. 8 illustrates the elution profiles of LUVs prepared from DOPE:cholesterol:DSPE-PEG$_{2000}$, and micelles composed of DSPE-PEG$_{2000}$. LUVs were prepared, as described in the examples, from DOPE:cholesterol:DSPE-PEG$_{2000}$ (1:1:0.1) with trace amounts of $^{14}$C-DPPC (Δ) and $^{3}$H-DSPE-PEG$_{2000}$. (●) They were chromatographed as described in the examples. In a separate experiment, micelles were prepared from DSPE-PEG$_{2000}$ labelled with $^{3}$H-DSPE-PEG$_{2000}$ (○) and chromatographed on the same Sepharose 4B column.

The presence of lipid micelles is not readily apparent from freeze fracture electron microscopy. Lipid in the micellar phase could, however, contribute to the isotropic signal observed in NMR spectra, and it has previously been shown that PEG-PE conjugates form micelles when hydrated in isolation (Woodle and Lasic, Biochim. Biophys. Acta, 113:171–199 (1992)). As such, the presence of micelles was tested by subjecting a suspension of LUVs to molecular sieve chromatography on Sepharose 4B. The liposomes were of the same composition used for the freeze fracture studies above except that DSPE-$PEG_{2000}$ was used in place of DOPE-$PEG_{2000}$, and they contained trace amounts of $^{14}$C-DPPC and $^{3}$H-DSPE-$PEG_{2000}$. The elution profile is shown in FIG. 8. A single peak containing both the phospholipid and PEG-PE conjugate markers was found in the void volume. A control experiment also shown in FIG. 8 demonstrated that micelles, which formed when PEG-PE was hydrated in isolation, were included into the column and would have been clearly resolved if present in the liposomal preparation.

g. Effect of PE-$PEG_{2000}$ on Fusion of PE:PS LUVs

Figure 9:
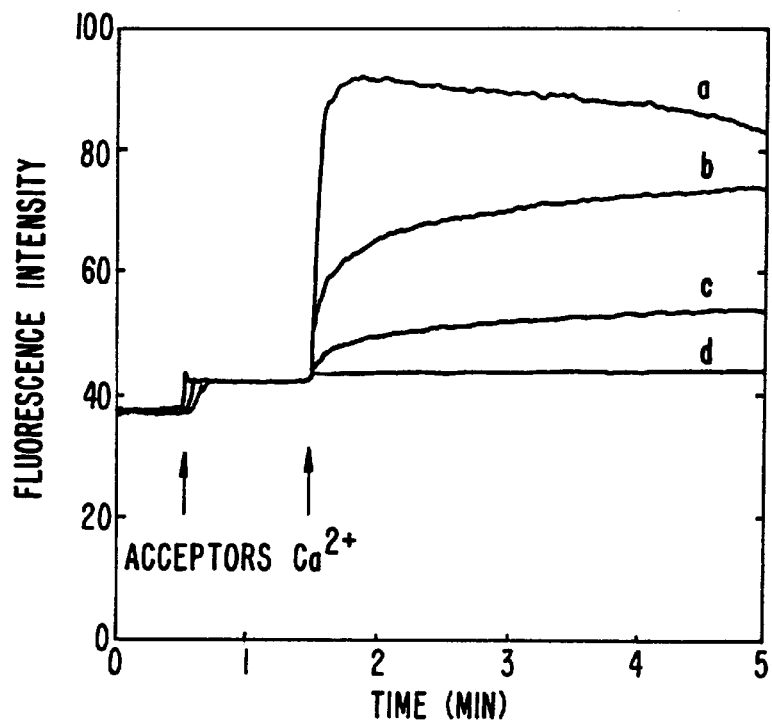
FIG. 9 illustrates the inhibition of fusion by PEG-PE. Liposomes were prepared from equimolar mixtures of DOPE and POPS containing (a) 0; (b) 0.5; (c) 1 or (d) 2 mol % DMPE-PEG$_{2000}$. In addition to the above lipids, labelled liposomes also contained the fluorescent lipids NBD-PE and Rh-PE at 0.5 mol %. Fluorescently labelled liposomes (final concentration 60 $\mu$M) were incubated at 37° C. for 30 sec. before the addition of a three-fold excess of unlabelled liposomes, followed one minute later by CaCl$_2$ (final concentration 5 mM).

When unlabelled LUVs composed of DOPE:POPS (1:1) were added to fluorescently labelled LUVs there was a small jump in fluorescence intensity due to increased light scattering but no fusion (FIG. 9, trace a). Upon addition of 5 mM $Ca^{2+}$, there was a rapid increase in fluorescence consistent with lipid mixing as a result of membrane fusion. Fusion was complete within a few seconds and was followed by a slow decrease in fluorescence. Inspection of the cuvette revealed the presence of visible aggregates that settled despite stirring, resulting in the observed decrease in fluorescence. When $PEG_{2000}$ conjugated to dimyristoylphosphatidylethanolamine (DMPE-$PEG_{2000}$) was included in both vesicle populations, however, inhibition of fusion was observed. As shown in FIG. 9 (traces b–d), inhibition was dependent on the concentration of DMPE-PEG2 $_{2000}$ in the vesicles with as little as 2 mol % being sufficient to eliminate $Ca^{2+}$—induced fusion.

h. The Effect of PE-PEG Loss on Fusion

Figure 10:
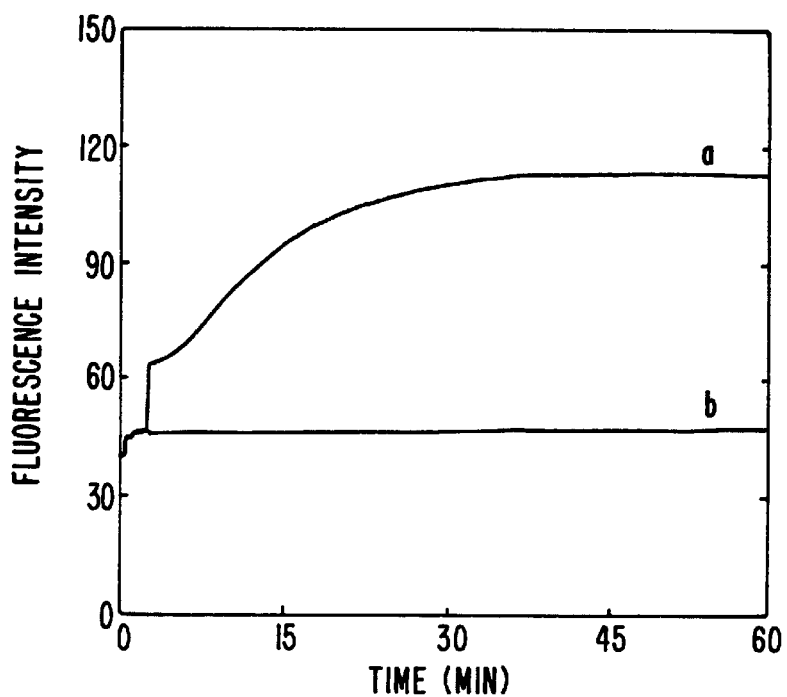
FIG. 10 illustrates the recovery of fusogenic activity after PEG-PE removal. Fusion between fluorescently labelled and unlabeled liposomes containing 2 mol % DMPE-PEG$_{2000}$ was assayed as described under FIG. 9, except that one minute after addition of CaCl$_2$, a 12-fold excess (over labelled vesicles) of POPC liposomes (curve a) or an equivalent volume of buffer (curve b) was added.

Recently, it has been demonstrated that phospholipids conjugated to PEG of molecular weights 750–5,000 Da have enhanced rates of spontaneous transfer between liposomes. The half-time for transfer of these conjugates can vary from minutes to hours and depends on both the size of the PEG group and the nature of the acyl chains which anchor the conjugate in the bilayer. As such, fusion was examined under conditions where the PEG-lipid would be expected to transfer out of the liposomes. $Ca^{2+}$ ions were added to PE:PS liposomes containing 2 mol % $DMPE-PEG_{2000}$, followed by a twelve-fold excess (over labelled vesicles) of 1-paimitoyl-2-oleoyl-phosphatidylcholine (POPC) liposomes as a sink for the PEG-PE. As shown in FIG. 10 (curve a), while fusion was initially blocked by the presence of $DMPE-PEG_{2000}$, the addition of POPC liposomes, which acted as a sink, lead to recovery of full fusogenic activity following a short time lag. The small initial jump in fluorescence intensity that occurred when POPC liposomes were added to PE:PS liposomes resulted from increased light scattering, not fusion. Control experiments demonstrated that no fusion occurred between the PE:PS liposomes and the POPC liposomes (data not shown), and no fusion occurred in the absence of POPC liposomes (FIG. 10, curve b).

Figure 11:
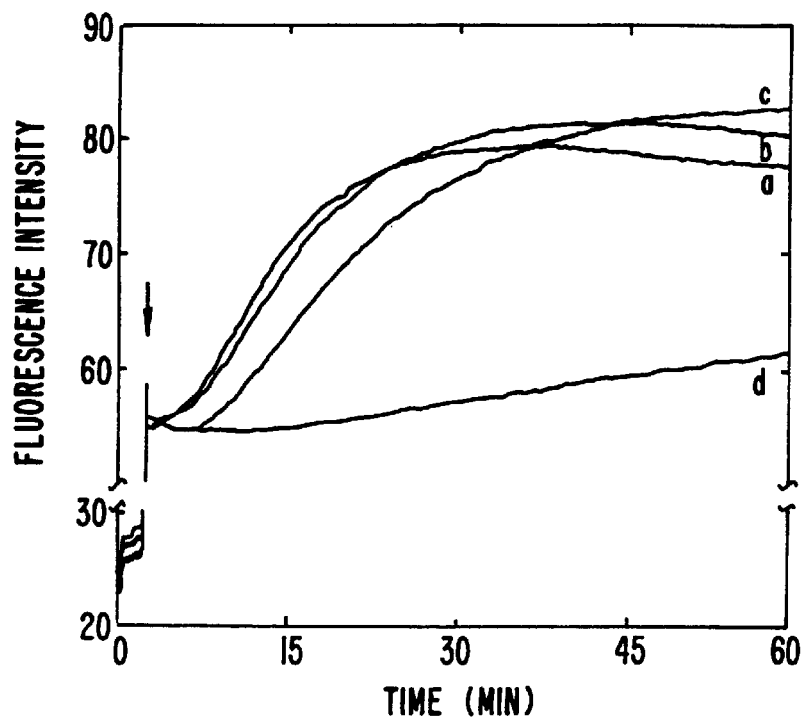
FIG. 11 illustrates the concentration dependence of recovery of fusogenic activity. Fusion between fluorescently labelled and unlabelled liposomes containing (a) 2; (b) 3; (c) 5 or (d) 10 mol % DMPE-PEG$_{2000}$ was assayed as described under FIG. 10, except that POPC liposomes were added as a 36-fold excess over labelled vesicles.

To confirm that recovery of fusogenic activity was dependent on removal of the PEG-PE, the influence of initial PEG-lipid concentration on the duration of the lag phase prior to fusion was examined (FIG. 11). Liposomes containing equimolar PE and PS were prepared with 2, 3, 5 or 10 mol % $DMPE-PEG_{2000}$ m. Fluorescently labelled and unlabelled vesicles were mixed at a ratio of 1:3 and after the addition of 5 mM $CaCl_2$, a 36-fold excess (over labelled vesicles) of POPC liposomes was added. As expected, there was an increase in the time delay prior to fusion with increasing PEG-lipid concentration.

i. The Effect of Conjugate Acyl Chain Composition on Fusogenic Activity

Figure 12A:
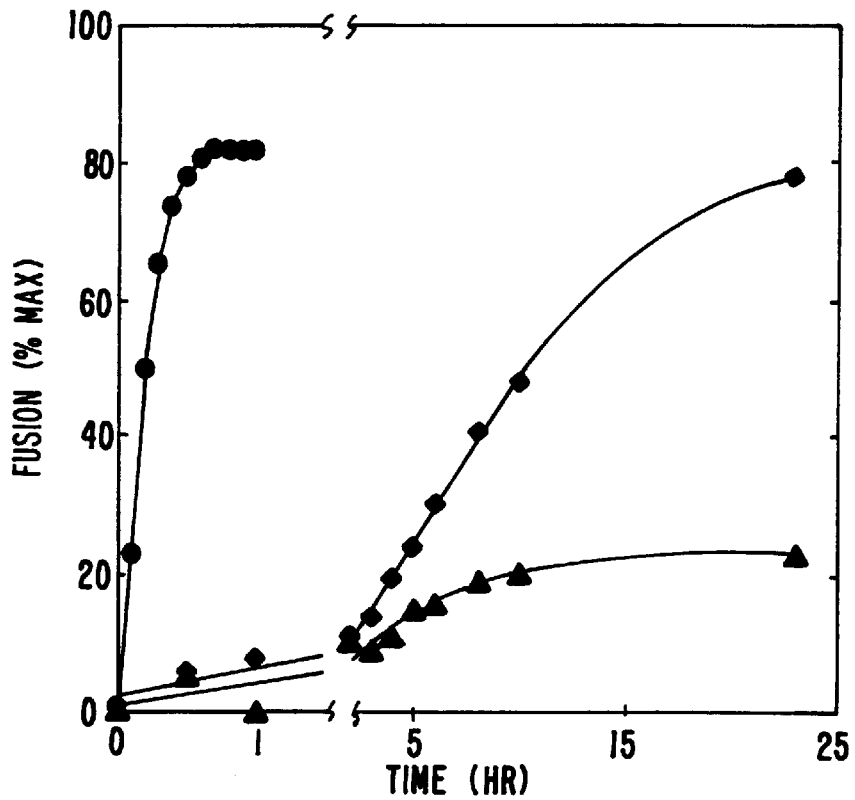
FIG. 12A: DMPP-PEG$_{2000}$ (●); DPPE-PEG$_{2000}$ (♦); DSPE-PEG$_{2000}$ (▲)

Since fusion is dependent on prior transfer of the PEG-PE out of the liposomes, it was thought that the rate at which fusogenic activity was recovered would depend on the rate of transfer of the PEG-PE. One factor that affects the rate at which a phospholipid transfers from one membrane to another is the length of its acyl chains. As such, the effect of conjugate acyl chain composition on fusogenic activity was investigated. In doing so, the recovery of fusogenic activity of PE:PS LUVs containing 2 mol % $DMPE-PEG_{2000}$ was compared with PE:PS LUVs containing 2 mol % $DPPE-PEG_{2000}$ and 2 mol % $DSPE-PEG_{2000}$ (FIG. 12A). Increasing the length of the acyl chains from 14 to 16 carbons caused a dramatic increase in the lag period before fusion was initiated. Although the same level of fusion occurred using either $DMPE-PEG_{2000}$ or $DPPE-PEG_{2000}$, it was essentially complete in 40 minutes when $DMPE-_{2000}$ was the stabilizer, but took 24 hours when $DPPE-PEG_{2000}$ was used. The implied decrease in rate of transfer (30–40 fold) is consistent with previous measurements of the effect of acyl chain length on rates of spontaneous phospholipid transfer. Increasing the acyl chain length to 18 carbons ($DSPE-PEG_{2000}$, FIG. 12A) extended the lag in fusion even further and, after 24 hours, the level was only 20% of maximum.

Figure 12B:
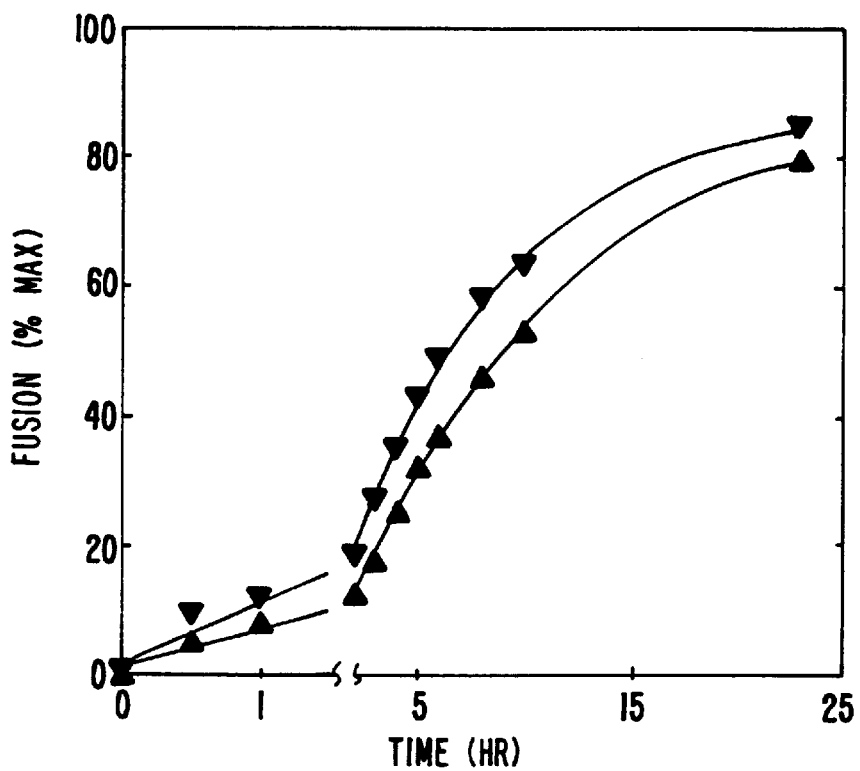
FIG. 12B: DOPE-PEG$_{2000}$ (▲), egg ceramide-PEG2000 (▼).

A second factor that affects the rate of spontaneous transfer of phospholipids between bilayers is the degree of saturation or unsaturation of the acyl chains. The rate of fusion of LUVs containing 2 mol % DOPE-PEG2000 is shown in FIG. 12B. The presence of a double bond increased the rate of recovery of fusogenic activity in the presence of a sink for the $DOPE-PEG_{2000}$ over that of the corresponding saturated species ($DSPE-PEG_{2000}$, FIG. 12A). The rate of fusion was similar to that seen with $DPPE-PEG_{2000}$. FIG. 12B also shows the rate of fusion obtained when the neutral PEG-lipid species, egg ceramide-$PEG_{2000}$ was used. The rate was somewhat faster than observed with DPPE-$PEG_{2000}$. Although differences in the interaction of the two lipid anchors with neighboring phospholipids in the bilayer make direct comparison of interbilayer transfer rates and, hence, fusion difficult, it appears that the presence of a negative charge on the conjugate (PE-PEG) is not required for desorption of the conjugate from negatively charged bilayers.

j. Effect of PEG Molecular Weight on Fusogenic Activity

Figure 13A:
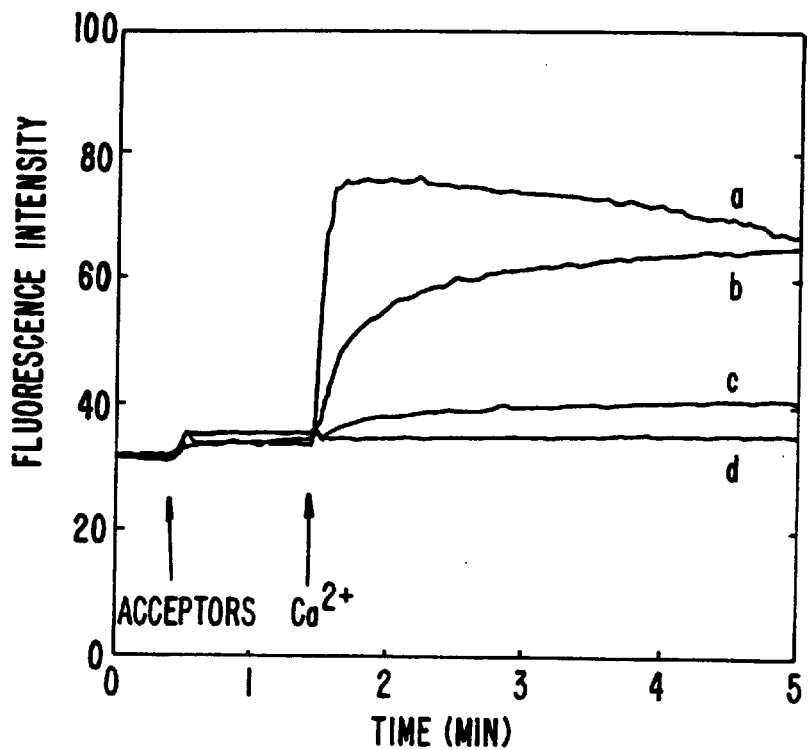
FIG. 13A: Assays were carried out as described in FIG. 9 using liposomes which contained (a) 0; (b) 0.25; (c) 0.5 or (d) 1 mol % DMPE-PEG$_{5000}$.

The presence of PEG conjugated to the liposome surface results in a steric barrier that inhibits close bilayer apposition and subsequent fusion. The magnitude of the barrier should increase with increasing PEG molecular weight. When $DMPE-PEG_{5000}$ was incorporated into PE:PS (1:1) LUVS, a concentration dependent inhibition of fusion was observed (FIG. 13A). The results are similar to those obtained with $DMPE-PEG_{2000}$ (FIG. 9), except that only 1 mol % $DMPE-PEG_{5000}$ was required to completely inhibit fusion compared to 2 mol % $DMPE-PEG_{2000}$.

Figure 14:
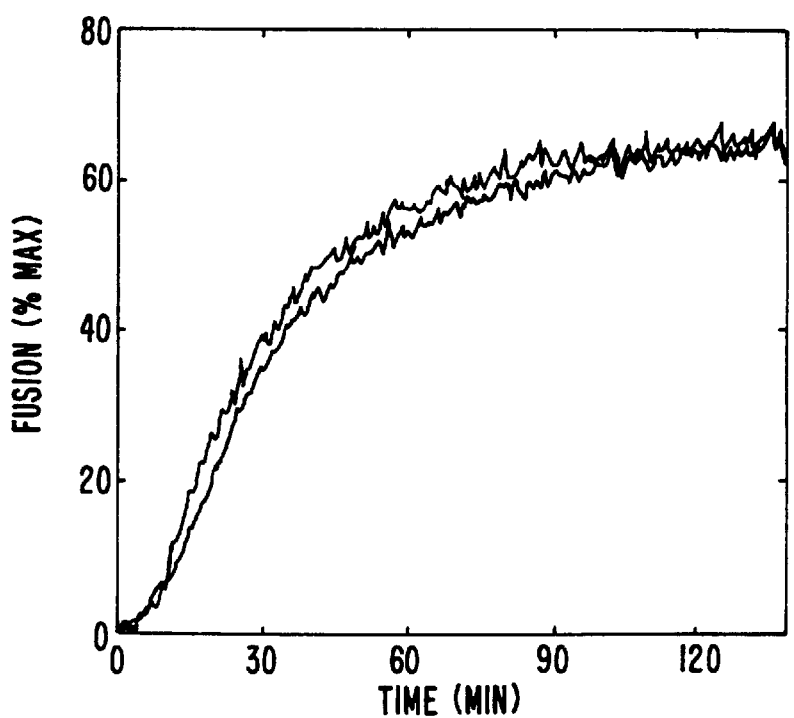
FIG. 14 illustrates the comparison of PEG$_{2000}$ to PEG$_{5000}$ at equal concentration of oxyethylene groups. Liposomes contained either 2 mol % PEG$_{5000}$ (upper curve) or 5 mol % PEG$_{2000}$ (lower curve). Other conditions were as described under FIG. 11.
Figure 13B:
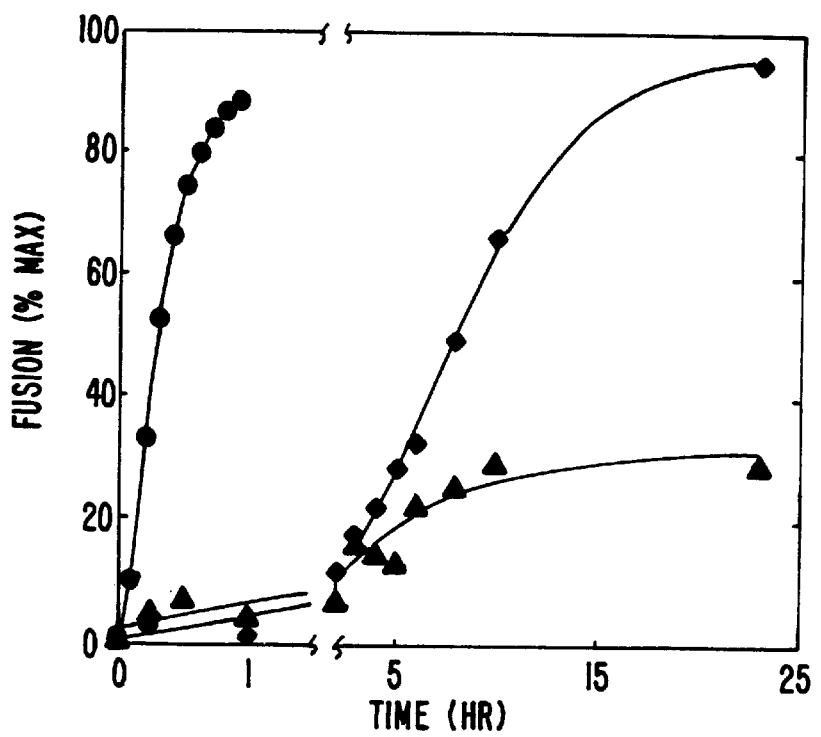
FIG. 13B: Assays were performed as described under FIG. 12 using liposomes which contained 1 mol % DMPE-PEG$_{5000}$ (●); DPPE-PEG$_{5000}$ (♦) or DSPE-PEG$_{5000}$ (▲).

FIG. 13B shows the effect of varying acyl chain composition of the larger PEG-lipid conjugate on fusion. Interestingly, the rates of fusion observed with 1 mol % $PE-PEG_{50000}$ were similar to those with 2 mol % $PE-PEG_{2000}$. The concentrations used were those shown to be sufficient to completely inhibit fusion (cf., FIG. 9 and FIG. 13A). It was thought that the larger PEG group would increase the rate of interbilayer transfer of the conjugate and, hence, the rate of fusion. However, this was not the case. To examine this aspect further, the rates of fusion under conditions where the initial surface density of ethylene glycol groups was similar were compared. FIG. 14 shows the fusion of PE:PS (1:1) LUVs containing 5 mol % $DMPE-PEG_{2000}$ or 2 mol % $DMPE-PEG_{5000}$ after addition of a sink for the PEG-lipid. The rates observed were very similar suggesting that factors other than loss of the steric barrier as a direct result of interbilayer transfer of the conjugate were involved.

k. Programmable Fusogenic Liposomes Comprising DOPE:Cholesterol:DODAC:Ceramides

Figure 15:
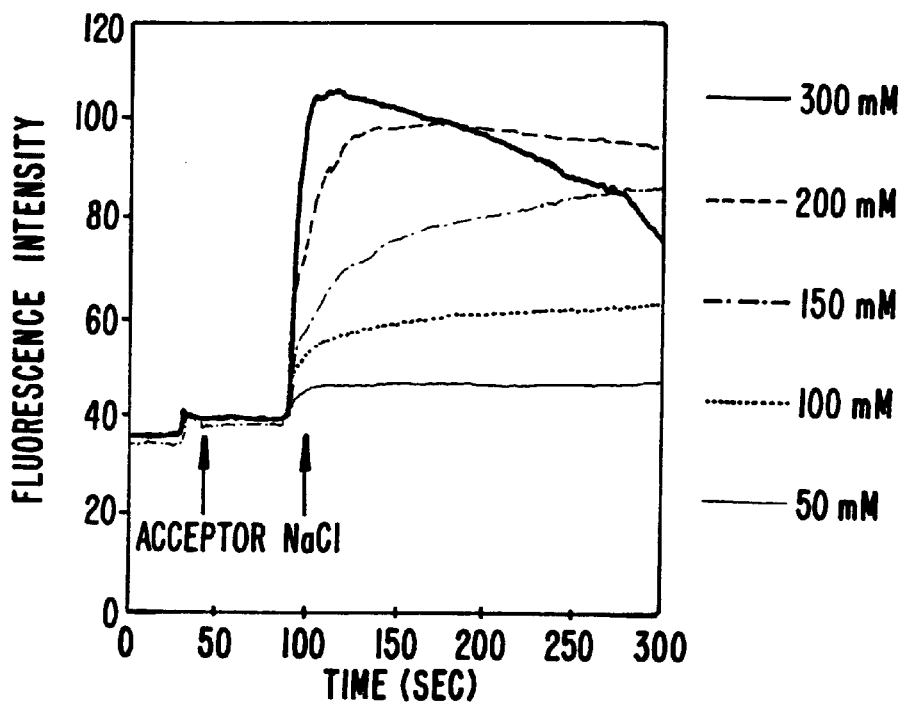
FIG. 15 illustrates the effect of salt concentration on fusion of DOPE:DODAC Liposomes. Liposomes were prepared from DOPE:DODAC (85:15). Donor liposomes also contained the fluorescent lipids, NBD-PE and Rh-PE at 0.5 mol %. Donor liposomes (final concentration 60 $\mu$M) were incubated at 37° C. for 30 sec. before the addition of a three-fold excess of unlabelled acceptor liposomes followed 1 min later by NaCl to give the indicated final concentration.

Fluorescently labelled liposomes were prepared in distilled water from a mixture of DOPE and N,N-dioleoyl-N, N-dimethylammonium chloride (DODAC) at a molar ratio of 85:15. A three-fold excess of acceptor liposomes of the same composition, but containing no fluorescent probes, was added to labelled liposomes and fusion was initiated after 60 sec. by the addition of NaCl (FIG. 15). Fusion was highly dependent on ionic strength. Little fusion was observed at 50 mM NaCl, but with increasing salt concentration, the rate and extent of fusion increased dramatically. At 300 mM NaCl fusion was so extensive that visible aggregates occurred and these aggregates could not be maintained in suspension resulting in the apparent decrease in fluorescence seen in FIG. 15 for the 300 mM NaCl curve. Importantly, substantial fusion was observed at physiological salt concentration (150 mM).

Figure 16:
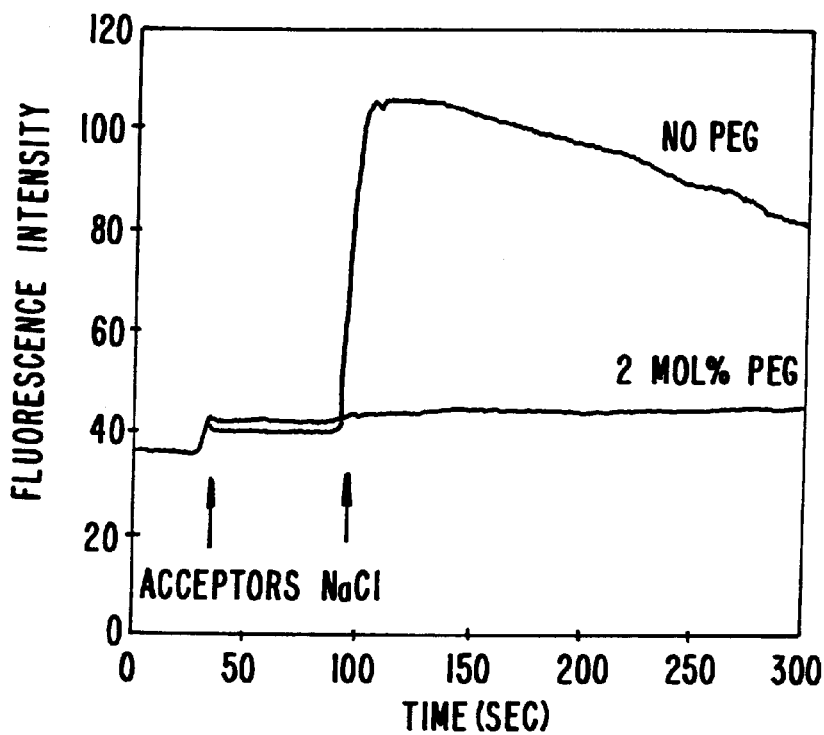
FIG. 16 illustrates the inhibition of fusion of DOPE:DODAC liposomes by PEG-PE. Liposomes were prepared from either DOPE:DODAC (85:15) or DOPE:DODAC:DMPE-PEG$_{2000}$ (83:15:2). Fusion was assayed as described under FIG. 1 using 300 mM NaCl.

As described above, the inclusion of 2 mol % PEG-lipid in PE:PS liposomes is sufficient to inhibit $Ca^{2+}$-induced fusion. When 2 mol % $DMPE-PEG_{2000}$ was included in DOPE:DODAC liposomes (DOPE:DODAC:DMPE-$PEG_{2000}$, 83:15:2), the same inhibitory effect was observed (FIG. 16). However, unlike the PE:PS system, when these liposomes were incubated for 1 hr. in the presence of a large excess of POPC liposomes, which acted as a sink for the PEG-PE, little, if any, fusion was observed. Since PEG-PEs are negatively charged the complementary charge, interaction with DODAC likely results in a dramatic decrease in the rate of transfer out of the bilayer.

Figure 17:
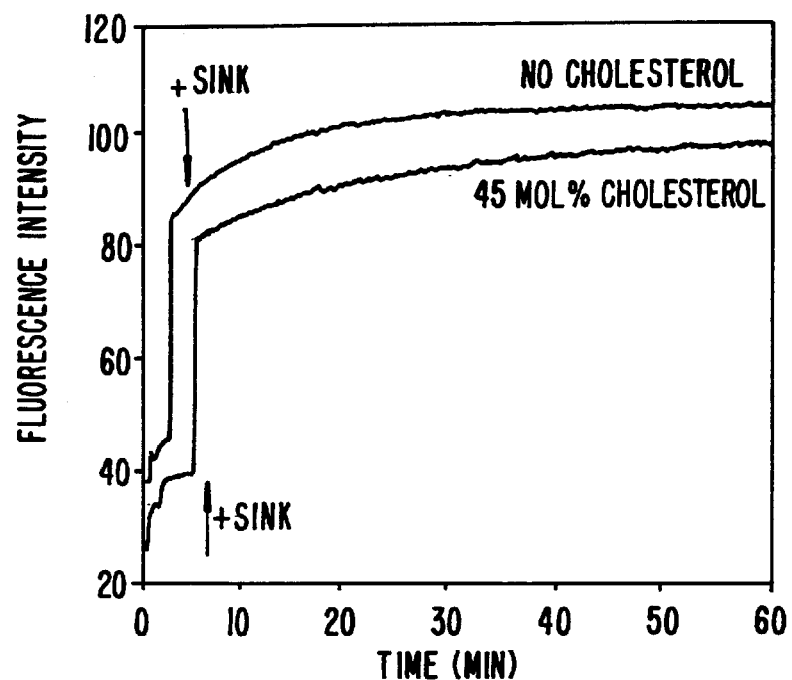
FIG. 17 illustrates the recovery fusogenic activity after PEG removal. Liposomes were prepared from either DOPE:DODAC:ceramide(C8:0)-PEG$_{2000}$, 83:15:2 or DOPE:cholesterol:ceramide(C8:0)-PEG$_{2000}$, 38:45:15:2. Fusion was assayed as described under FIG. 2 except that at the indicated times a 30 fold excess (over donors) of liposomes composed of POPC or POPC:cholesterol (55:45) was added.

As an alternative bilayer stabilizing component, therefore, the ability of a neutral PEG-lipid species, i.e., PEG-ceramide, to inhibit fusion in this system was examined. PEG-ceramides have similar bilayer stabilizing properties to PEG-PEs. For these studies, PEG$_{2000}$ was conjugated to ceramides of various fatty amide chain lengths through a succinate linker. Liposomes prepared from DOPE:DODAC: (C8:0) ceramide-PEG$_{2000}$ (83:15:2) did not fuse in the presence of 300 mM NaCl. However, when an excess of POPC liposomes was added, fusion occurred fairly rapidly (FIG. 17). Similar results were observed when cholesterol was incorporated into the liposomes (DOPE:cholesterol:DODAC:(C8:0) ceramide-PEG$_{2000}$, 38:45:15:2), although the rate of fusion was slower than with cholesterol-free liposomes (FIG. 17).

Figure 18:
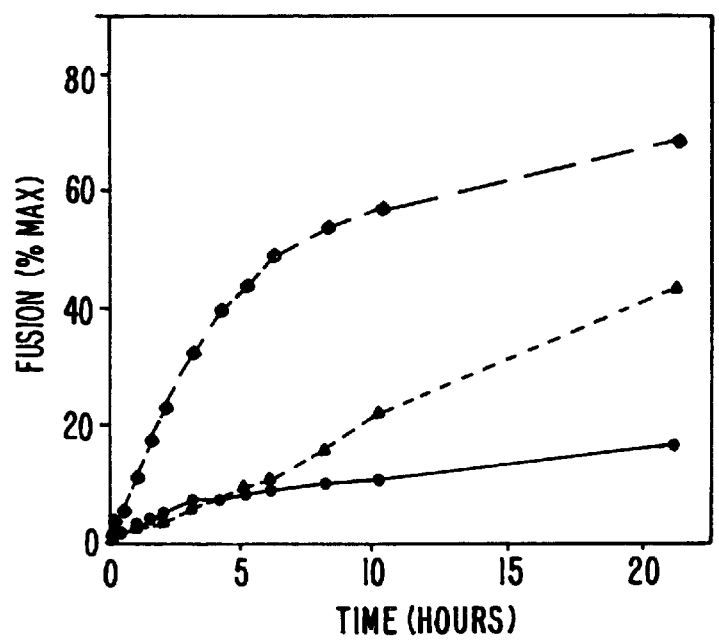
FIG. 18 illustrates the effect of the lipid anchor on the rate of PEG-lipid removal. Fluorescently labelled and unlabelled liposomes were prepared from DOPE:DODAC:PEG-lipid, 83:15:2, using DMPE-PEG$_{2000}$ (●), ceramide(egg)-PEG$_{2000}$ or (C14:0) ceramide-PEG$_{2000}$ (♦). Labelled liposomes were mixed with a 3 fold excess of unlabelled liposomes and 300 mM NaCl in a cuvette in a dark water bath at 37° C. At zero time a 13-fold excess (over labelled vesicles) of POPC liposomes was added and the fluorescence intensity was measured at the indicated times. At the end of the assay Triton X-100 (0.5% fmal) was added to eliminate energy transfer and the % fusion was calculated from the change in efficiency of energy transfer. Maximum fusion was calculated from a standard curve of energy transfer efficiency against the molar fraction of Rh-PE in. the membrane assuming complete mixing of labelled and unlabelled liposomes.

To determine if the rate of fusion in this system can be controlled, the chain lengths of the fatty amide groups of the PEG-ceramides were varied. Using a (C14:0) ceramide-PEG$_{2000}$, 50% maximal fusion was observed after approximately 6 hr (FIG. 18). This was a dramatic increase over the rate with (C8:0) ceramide-PEG$_{2000}$ shown in FIG. 18, where maximal fusion was achieved in about 40 minutes. The time for 50% maximal fusion was increased to over 20 hr when egg ceramide-PEG$_{2000}$ was used. Ceramides derived from egg have a fatty amide chain length of predominantly 16:0 (approximately 78%), with small amounts of longer saturated chains. FIG. 18 also shows an extended time course with DMPE-PEG$_{2000}$. The limited extent of fusion (<20% of maximum at 21 hr) shows the dramatic effect that charge interaction can have on PEG-lipid transfer rates.

Figure 19:
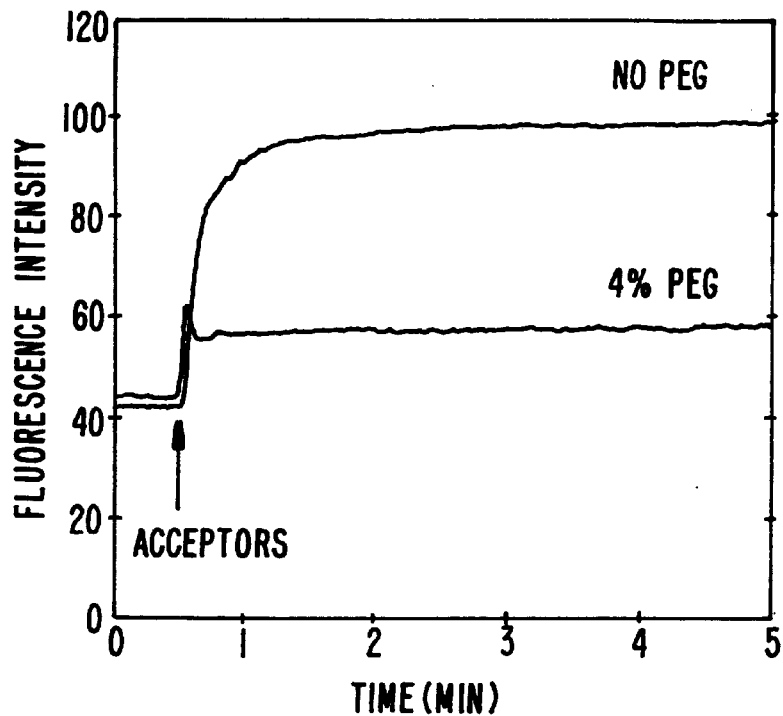
FIG. 19 illustrates the inhibition of fusion between DOPE:cholesterol:DODAC liposomes and anionic liposomes by PEG-ceramide. Liposomes were prepared from DOPE:cholesterol:DODAC, 40:45:15 (no PEG) or DOPE:cholesterol:DODAC:(C14:0) ceramide-PEG$_{2000}$, 36:45:15:4 (4% PEG). Acceptor liposomes were prepared from DOPE:cholesterol:POPS, 25:45:30. A three-fold excess of acceptors was added to labelled vesicles after 30 sec. and the fluorescence monitored at 517 nm with excitation at 465 nm.

The rationale for using cationic liposomes is that complementary charge interaction with anionic plasma membranes will promote association and fusion of liposomes with cells in vivo. It is important, therefore, to confirm that not only will DOPE:DODAC liposomes fuse with membranes carrying a negative charge, but that incorporation of PEG-lipid conjugates prevents fusion in a programmable manner. This ability is demonstrated in FIG. 19 which shows that liposomes composed of DOPE:cholesterol:DODAC, 40:45:15, fuse with negatively charged liposomes and inclusion of a PEG-lipid conjugate in the cationic liposomes inhibits fusion. Fusion between DOPE:DODAC liposomes could be prevented when 2 mol % PEG-lipid was present in both fluorescently labelled and acceptor liposomes. When PEG-lipid was omitted from the acceptor liposomes, however, its concentration in the labelled vesicles had to be increased to 4–5 mol % to block fusion between cationic and anionic liposomes.

Figure 20:
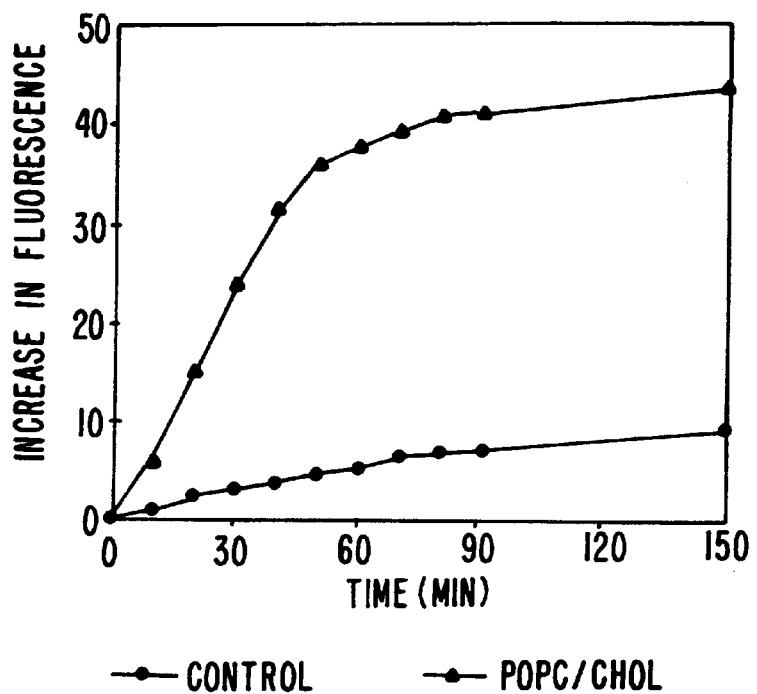
FIG. 20 illustrates the recovery of fusogenic activity upon PEG removal. Donor liposomes (50 $\mu$M) were prepared from DOPE:cholesterol:DODAC: (C14:0)ceramide-PEG$_{2000}$, 36:45:15:4 and mixed with acceptor liposomes (150 $\mu$M) prepared from DOPE:cholesterol:POPS, 25:45:30. At zero time either 1 mM POPC:cholesterol liposomes (▲) or an equivalent volume of buffer (●) was added. Fluorescence was monitored at 517 nm with excitation at 465 mn.

Again, while PEG-lipids can inhibit fusion in this system, under conditions where the PEG-lipid can transfer out of the liposomes, fusogenic activity can be restored. FIG. 20 shows that this is, indeed, the case. Incubation of DOPE:cholesterol: DODAC:(C14:0) ceramide-PEG$_{2000}$ (36:45:15:4) liposomes with PE:PS liposomes, in the presence of excess POPC:cholesterol (55:45) vesicles which act as a sink, results in recovery of fusogenic activity. In the absence of a sink, a slow rate of fusion is observed, indicating that a higher concentration of PEG-lipid is required to completely prevent fusion over longer periods.

Figure 21:
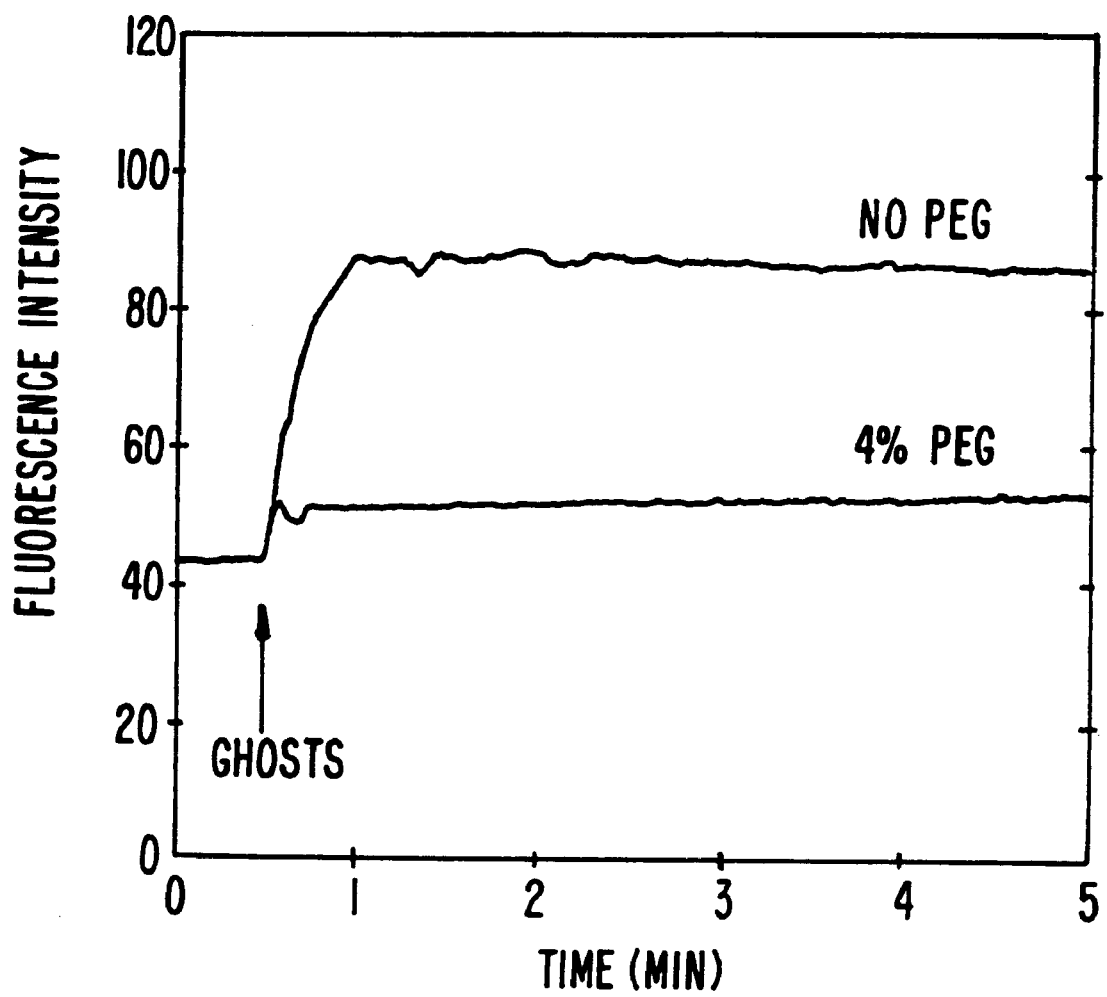
FIG. 21 illustrates the inhibition of fusion between DOPE:cholesterol:DODAC liposomes and erythrocyte ghosts by, PEG-ceramide. Liposomes were prepared from DOPE:cholesterol:DODAC, 40:45:15 (no PEG) or DOPE:cholesterol:DODAC:(C14:0)ceramide-PEG$_{2000}$, 36:45:15:4 (4% PEG). Ghosts (50 $\mu$M phospholipid) were added to donors (50 $\mu$M total lipid) after 30 sec. and the fluorescence monitored at 517 nm with excitation at 465 nm.
Figure 22A:
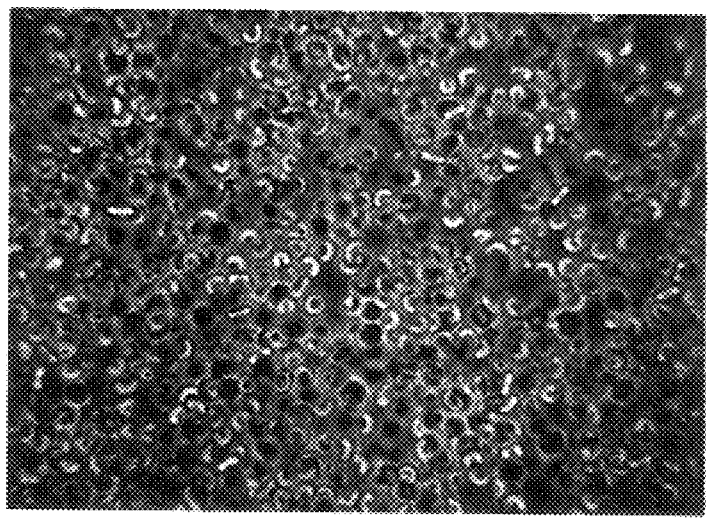
FIG. 22 illustrates the fusion of fluorescent liposomes composed of DOPE:cholesterol:DODAC (40:45:15) or DOPE:cholesterol:DODAC:PEG-ceramide (35:45:15:5). LUVs composed of DOPE:cholesterol:DODAC (40:45:15) fused with RBCs (panels a and b); incorporation of PEG-ceramide (C8:0) into the LUVs at 5 mol % blocked fusion (panels c and d); however, when an exogenous sink for the PEG-ceramide was included, fusogenic activity was recovered within minutes (panels e and f). Panels a, c and e are views under phase contrast, and panels b,d and f are the same fields view under fluorescent light.
Figure 22B:
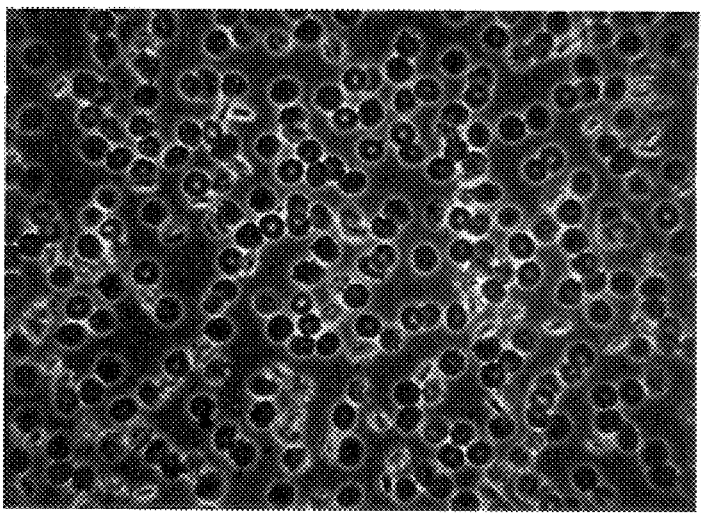
Figure 22C:
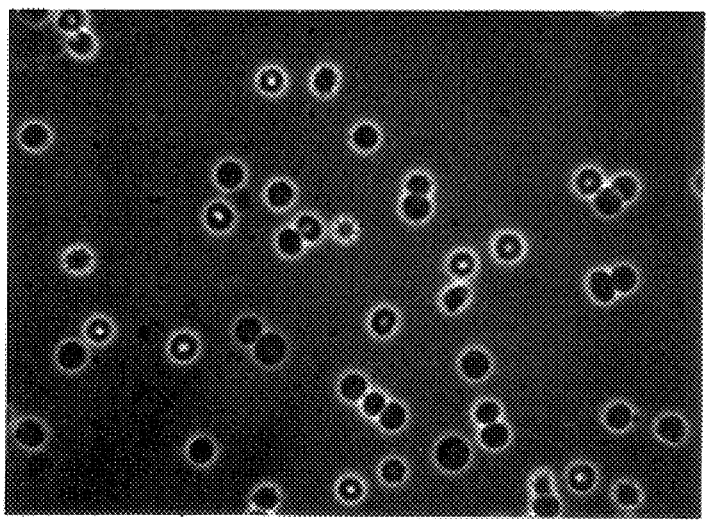
Figure 22D:
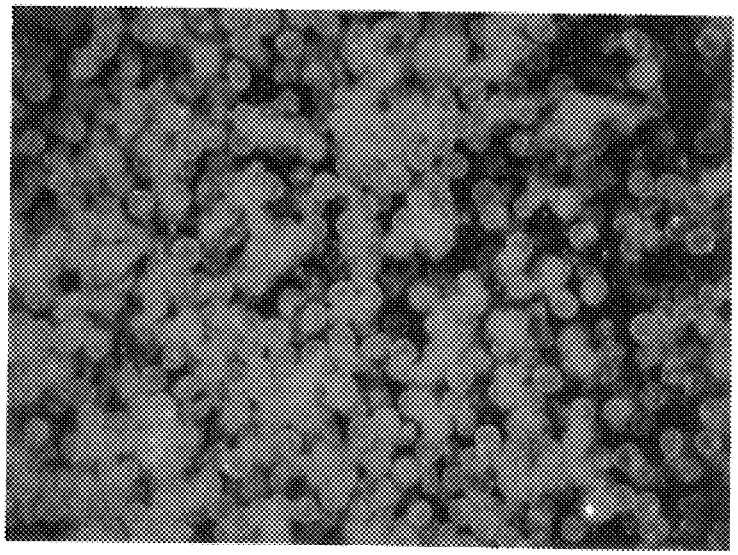
Figure 22E:
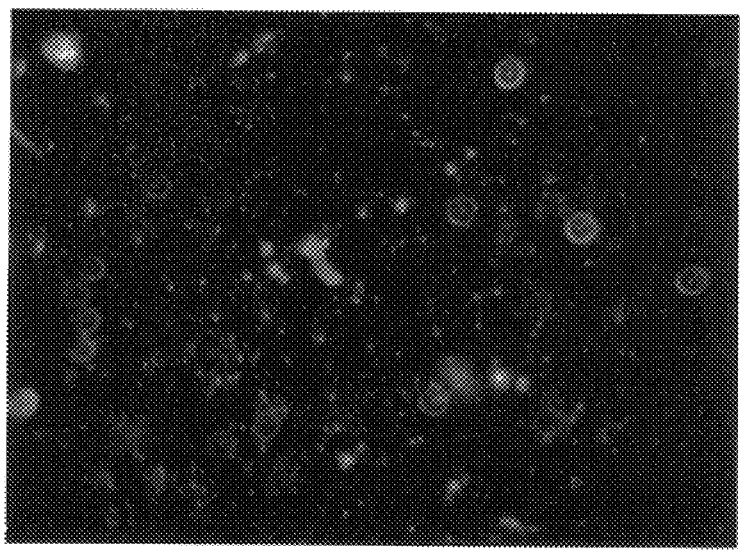
Figure 22F:
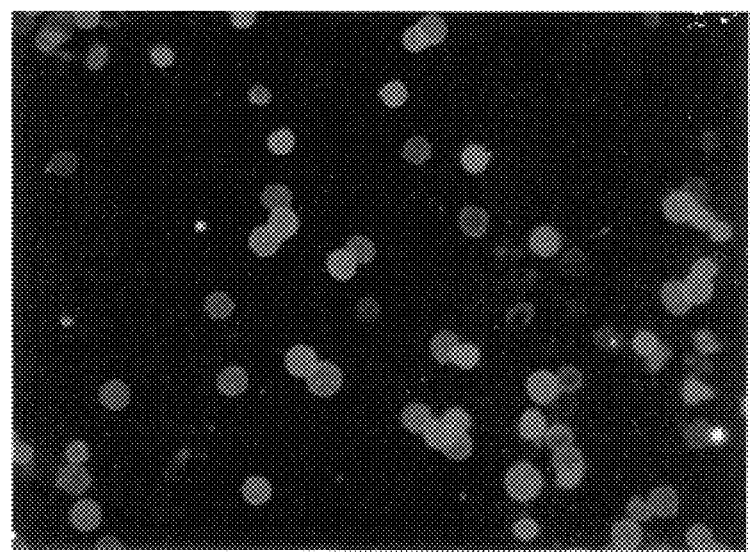
Figure 23A:
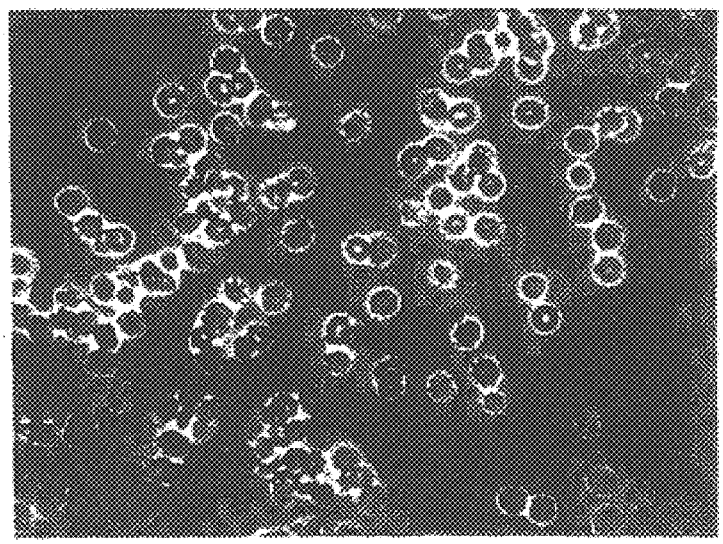
FIG. 23 illustrates the results when PEG-ceramides with longer fatty amide chains (C14:0) are used and the liposomes are pre-incubation with an exogenous sink prior to the addition of the RBCs. No fusion was observed after pre-incubation of the fusogenic LUVs with the sink for five minutes prior to addition of RBC (panels a and b); after a 1 hour pre-incubation, some fusion with RBCs was observed (panels c and d); however, with longer incubations times (2 hours), the pattern of fluorescent labeling changed and extensive punctate fluorescence was observed (panels e and f). Panels a, c and e are views under phase contrast, and panels b,d and f are the same fields view under fluorescent light.
Figure 23B:
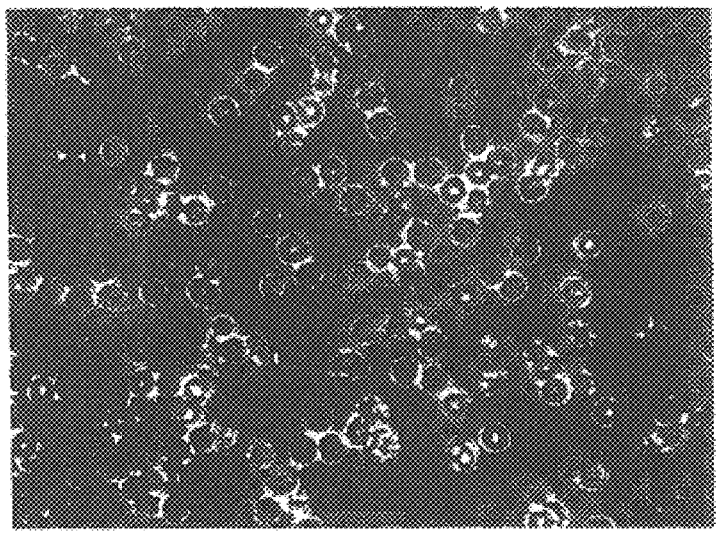
Figure 23C:
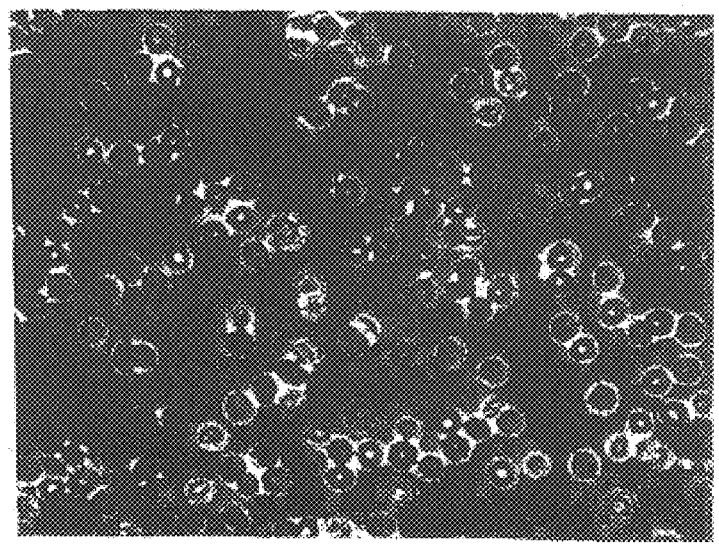
Figure 23D:
Figure 23E:
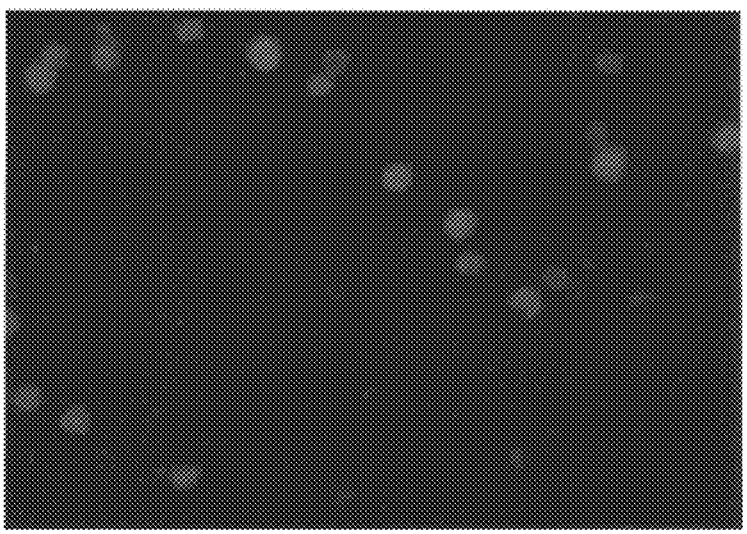
Figure 23F:
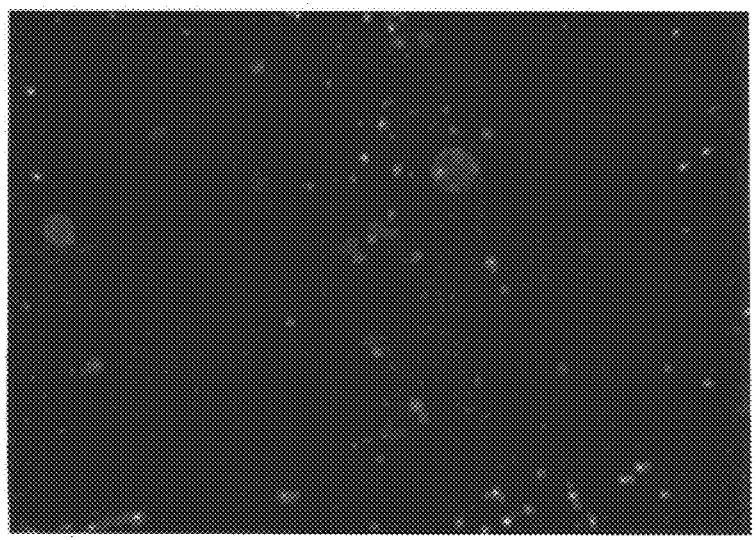
Figure 24A:
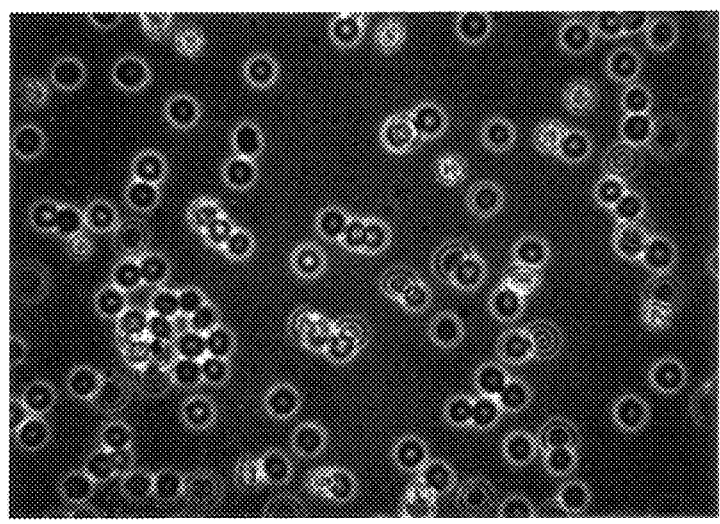
FIG. 24 illustrates the results when PEG-ceramides with longer fatty amide chains (C20:0) are used and the liposomes are preincubation with an exogenous sink prior to the addition of the RBCs. No fusion was observed after pre-incubation of the LUVs with the sink for five minutes (panels a and b), 1 hour (panels c and d) or 2 hours (panels e and f). Panels a, c and e are views under phase contrast, and panels b,d and f are the same fields view under fluorescent light.
Figure 24B:
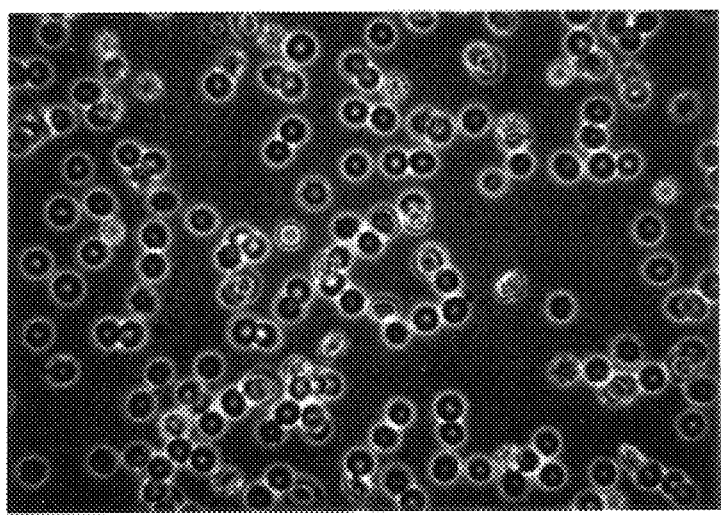
Figure 24C:
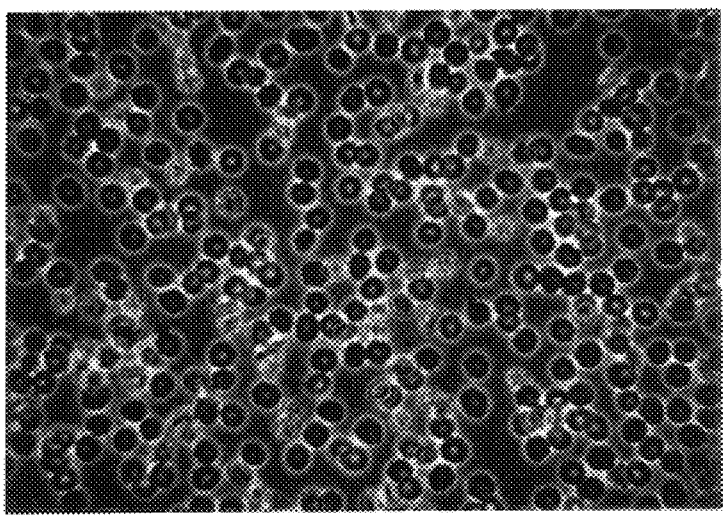
Figure 24D:
Figure 24E:
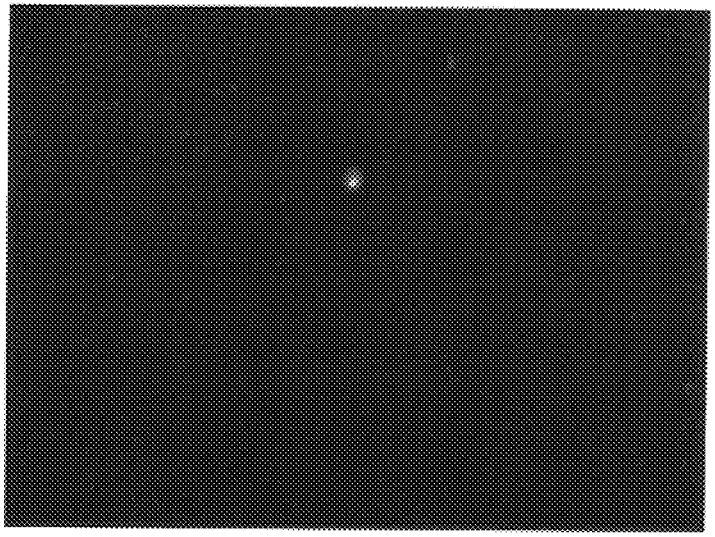
Figure 24F:
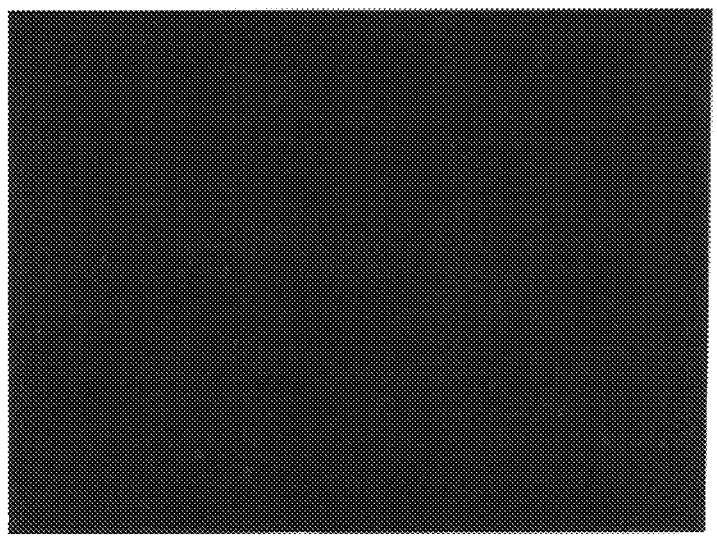

While fusion between cationic and anionic liposomes provides a good model system, fusion in vivo is somewhat different. The acceptor membrane is not composed solely of lipid, but contains a high concentration of proteins, many of which extend outward from the lipid bilayer and may interfere with fusion. Using erythrocyte ghosts as a representative membrane system, it was found that liposomes composed of DOPE:cholesterol:DODAC (40:45:15) fuse with cellular membranes (see, FIG. 21). In addition, it was found that fusion in this system, like those presented above, can also be inhibited using PEG-lipid conjugates. This results clearly establish the usefulness of these systems as programmable fusogenic carriers for intracellular drug delivery.

1. Programmed Fusion with Erythrocytes (RBCs)

LUVs composed of DOPE:cholesterol:DODAC (40:45:15) fused rapidly and extensively with RBCs (FIG. 22, panels a and b). Prolonged incubation caused extensive lysis of the RBCs and numerous fluorescently labeled "ghosts" were formed. Incorporation of PEG-ceramide (C8:0) at 5 mol % blocked fusion (FIG. 22, panels and d) and this effect was maintained for up to 24 hr. This effect was somewhat surprising since the (C8:0) ceramide can exchange rapidly (i.e., within minutes) between liposomal membranes. It appears that either the RBCs cannot act as a sink for the PEG-ceramide, or there were insufficient RBCs to remove enough PEG-ceramide to allow fusion. However, when an exogenous sink for the PEG-ceramide was included, fusogenic activity was recovered within minutes (FIG. 22, panels e and f).

When PEG-ceramides with longer fatty amide chains (i.e., C14:0 or C20:0) were used, there was little fusion over 24 hr, even in the presence of an exogenous sink. This again was surprising as substantial fusion is observed over this time frame in liposomal systems when a sink is present. It was thought that some non-specific interaction between the sink (POPC/cholesterol) and the RBCs was occurring which hindered the ability of the POPC:cholesterol liposomes to absorb the PEG-ceramide. To overcome this, the fusogenic liposomes were pre-incubated with the sink before adding RBCS. FIG. 23 shows the results obtained under these conditions using PEG-ceramide (C14:0). No fusion was observed after pre-incubation of the fusogenic LUVs with the sink for 5 minutes prior to addition of RBCs (FIG. 23, panels a and b). However, after a 1 hr pre-incubation, some fusion with RBCs was observed (FIG. 23, panels c and d), suggesting that under these conditions the PEG-ceramide could transfer out of the liposomes and became fusogenic. With longer incubations (2 hrs.), the pattern of fluorescent labeling changed. Rather than diffuse labeling of the RBC plasma membranes, extensive punctate fluorescence was observed (FIG. 23, panels e and f) and this pattern was maintained for up to 24 hr. The punctate fluorescence did not appear to be associated with cells and it may represent fusion of fluorescent liposomes with the sink, although previous fluorescent measurements of liposome-liposome fusion indicated that this did not occur to any appreciable extent. A second possibility is that exchange of the fluorescent probe over the longer time courses leads to labeling of the sink, although it seems unlikely that this would prevent fusion and labeling of the RBCS. When PEG-ceramide (C20:0) was used, there was no evidence for fusion after preincubation of LUVs with the sink for 5 min (FIG. 24, panels a and b), 1 hr (FIG. 24, panels c and d), 2 hr (FIG. 24, panels e and f), or for up to 24 hr (results not shown).

Figure 25:
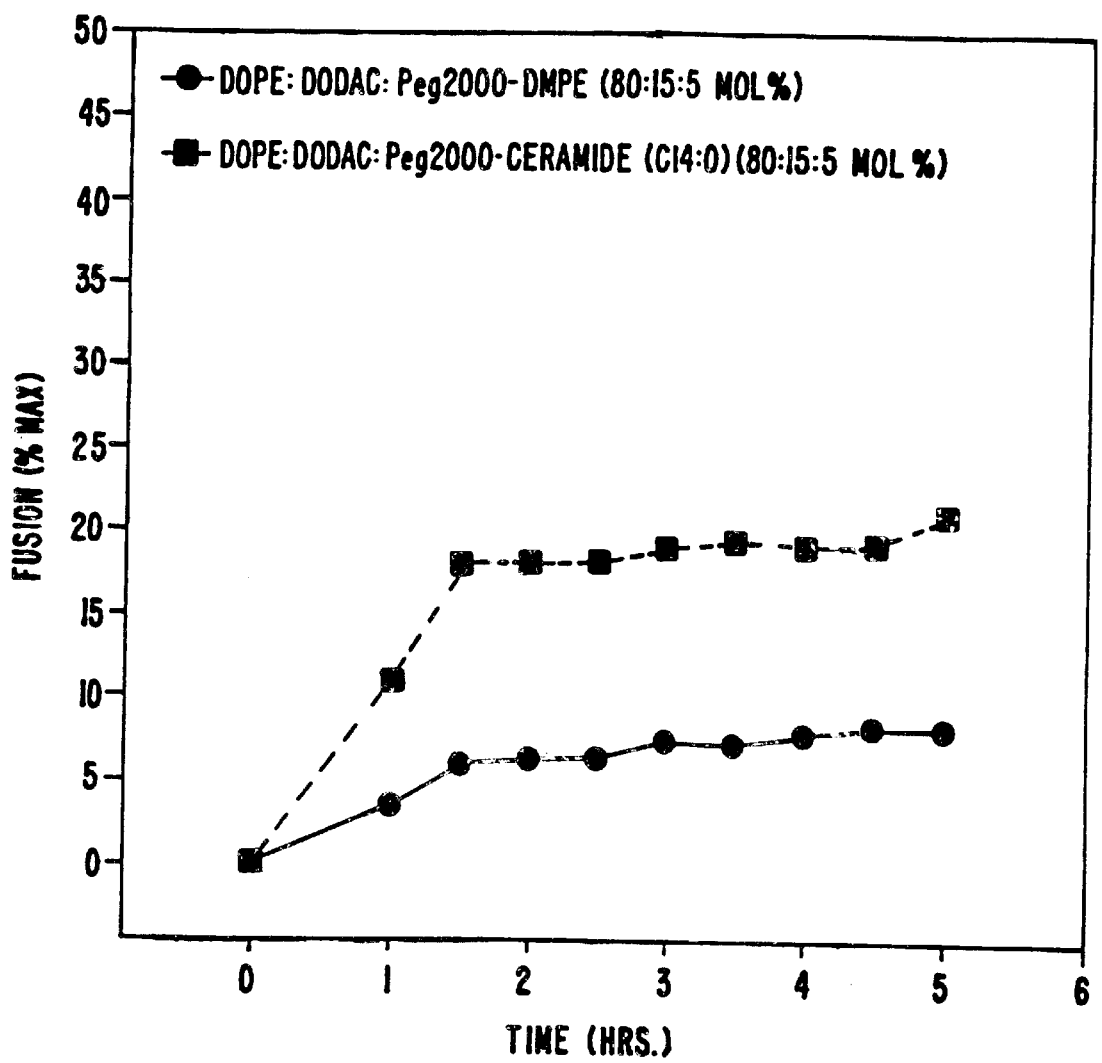
FIG. 25 graphically illustrates the fusion of $PEG_{2000}$-DMPE and $PEG_{2000}$-Ceramide (C14:0) containing vesicles with an anionic target.

FIGS. 22–24 unequivocally establish that the liposomes of the present invention exhibit programmable fusion with intact cells. Firstly, liposomes composed of DOPE:cholesterol:DODAC (40:45:15) that contain no PEG-lipid fuse rapidly and extensively with RBCs. Secondly, when the liposomes contain 5 mol % PEG-lipid fusion is blocked regardless of the composition of the lipid anchor. Thirdly, in the presence of a sink to which the PEG-lipid can transfer, fusogenic activity can be restored at a rate that is dependent on the nature of the lipid anchor. Although exchange leading to fusion could not be demonstrated when the PEG-ceramide (C20:0) was used, it is believed this is a problem with the assay rather than a lack of fusogenic potential. In vivo there would be an almost infinite sink for PEG-lipid exchange.

m. Inhibition of Transmembrane Carrier System (TCS) Fusion by PEG$_{2000}$-Ceramide (C14:0) and PEG$_{2000}$-DMPE TCS composed of 1,2-dioleoyl-3-phosphatidylethanolamine (DOPE), N,N-dioleoyl-N,N-dimethylammoniumchloride (DODAC), the fluorophores N-(7-nitro-2-1,3-benzoxadiazol-4-yl)-1,2-dioleoyl-sn-phosphatidylethanolamine (NBD-PE) and N-(lissamine rhodamine B sulfonyl)-1,2-dioleoyl-sn-phosphatidylethanolamine (Rh-PE), and either PEG$_{2000}$-Ceramide (C14:0) or PEG$_{2000}$-DMPE were prepared by extrusion through 100 nm diameter polycarbonate filters (Hope, M. J., et al., *P.R. Biochim. Biophys. Acta,* 812:55–65 (1985)). TCS contained 0.5 mol % NBD-PE and 0.5 mol % Rh-PE and either DOPE:DODAC:PEG$_{2000}$-DMPE (80:15:5 mol %) or DOPE:DODAC:PEG$_{2000}$-Ceramide (C14:0) (80:15:5 mol %). Fluorescently labelled liposomes were incubated at 37° C. in 20 mM HEPES, 150 mM NaCl, pH 7.4 (HBS) with a three-fold excess of liposomes composed of DOPE:POPS (85:15 mol %). POPC liposomes were added at 10-fold the concentration of the fluorescently labelled liposomes and lipid mixing was assayed by the method of Struck, D. K., et al. (*Biochemistry,* 20:4093–4099 (1981)). The excitation wavelength used was 465 nm and an emission filter placed at 530 nm minimized intensity due to scattered light. Rates and extents of fusion were followed by monitoring the increase in NBD fluorescence intensity at a wavelength of 535 nm over time. Percent maximum fusion was determined from the relationship Fusion (% max)(t)= $(F(t)-F_o)/(F_\infty-F_o)$, where $F_o$ is the initial NBD fluorescence intensity at time zero, F(t) is the intensity at time t and $F_\infty$ is the maximum achievable fluorescence intensity under conditions of complete lipid mixing of fluorescently labelled and DOPC:POPS liposomes (Bailey, A. L., et al., *P.R. Biochemistry,* 33:12573–12580 (1994)). FIG. 25 illustrates considerable mixing of DOPE/DODAC/PEG$_{2000}$-Ceramide (C14:0) with DOPC:POPS compared to that of DOPE/DODAC/PEG$_{2000}$-DMPE with DOPC:POPS, suggesting that the PEG$_{2000}$-DMPE is only minimally removed from the TCS. This result is attributed to the electrostatic interaction between the anionic PEG$_{2000}$-DMPE and cationic DODAC which effectively decreases the monomer concentration of the PEG$_{2000}$-DMPE in aqueous solution.

n. In vivo Stabilization of Liposomes Containing Cationic Lipids Using Amphipatic Bilayer Stabilizing Components The ability of a series of bilayer stabilizing components (e.g., PEG-modified lipids) to stabilize fusogenic liposomes containing a cationic lipid in vivo were examined in this study. A freeze-fracture electron microscope analysis of liposomes composed of dioleoylphosphatidylethanolamine (DOPE) and N,N-dioleoyl-N,N-dimethylammonium chloride (DODAC) showed that inclusion of a bilayer stabilizing component, e.g., PEG-DSPE and PEG-Ceramide, effectively prevented liposome aggregation in the presence of mouse serum. Biodistribution of fusogenic liposomes composed of DOPE and DODAC, additionally containing a bilayer stabilizing component (i.e., an amphipatic polyethyleneglycol (PEG) derivative), were then examined in mice using $^3$H-labelled cholesterylhexadecylether as a lipid marker. Bilayer stabilizing components included PEG-DSPE and various PEG-Ceramide (PEG-Cer) with different acyl chain length ranging from C8 to C24. DOPE/DODAC liposomes (85:15, mol/mol) were shown to be cleared rapidly from the blood and accumulate exclusively in the liver. Inclusion of a bilayer stabilizing component at 5.0 mol % of the lipid mixture resulted in increased liposome levels remaining in the blood and concomitantly decreased accumulation in the liver. Among the various bilayer stabilizing components, PEG-DSPE shows the highest activity in prolonging the circulation time of DOPE/DODAC liposomes. The activity of PEG-Ceramide is directly proportional to the acyl chain length: the longer the acyl chain, the higher the activity. The activity of PEG-Ceramide (C20) exhibiting the optimal acyl chain length depends on its concentration of the lipid mixture, with the maximal circulation time obtained at 30 mol % of the lipid mixture. While inclusion of bilayer stabilizing components in the lipid composition generally results in increased circulation time of DOPE/DODAC liposomes, the presence of a cationic lipid, DODAC, appeared to promote their rapid clearance from the blood.

The preparations and uses of DODAC liposomes are disclosed in U.S. patent application Ser. No. 08/316,399, filed Sep. 30, 1994, the teachings of which are incorporated herein by reference.

i. Materials and Methods aa. Liposome Preparation

Small unilamellar liposomes composed of DOPE and DODAC and bilayer stabilizing components at various ratios were prepared by the extrusion method. Briefly, the solvent-free lipid mixture containing $^3$H-labelled CHE, as a nonexchangeable and nonmetabolizable lipid marker, was hydrated with distilled water overnight. Normally, the liposome suspension (5 mg lipid per ml) was extruded, at room temperature, 10 times through stacked Nuclepore membranes (0.1 μm pore size) using an extrusion device obtained from Lipex Biomembranes, Inc. to generate liposomes with homogeneous size distributions. Liposome size was determined by quasi-elastic light scattering using a particle sizer and expressed as average diameter with standard deviation (SD).

bb. Liposome Biodistribution Study $^3$H-labelled liposomes with various lipid compositions were injected i.v. into female CD-1 mice (8–10 weeks old) at a dose of 1.0 mg lipid per mouse in 0.2 ml of distilled water. At specified time intervals, mice were killed by overexposure to carbon dioxide, and blood was collected via cardiac puncture in 1.5-ml microcentrifuge tubes and centrifuged (12000 rpm, 2 min, 4° C.) to pellet blood cells. Major organs, including the spleen, liver, lung, heart, and kidney, were collected, weighed, and homogenized in distilled water. Fractions of the plasma and tissue homogenates were transferred to glass scintillation vials, solubilized with Solvable (NEN) at 50° C. according to the manufacturer's instructions, decolored with hydrogen peroxide, and analyzed for $^3$H radioactivity in scintillation fluid in a Beckman counter. Data were expressed as percentages of the total injected dose of $^3$H-labelled liposomes in each organ. Levels of liposomes in the plasma were determined by assuming that the plasma volume of a mouse is 5.0% of the total body weight.

ii. Results and Discussion aa. Freeze-Fracture Electron Microscopic Studies

Liposomes composed of DOPE/DODAC (85:15, mol/mol), DOPE/DODAC/PEG-Ceriamide (C20) (80:15:5, mol/mol), and DOPE/DODAC/PEG-DSPE (80:15:5, mol/mol) were prepared by the extrusion method and had similar average diameters (100 nm). Freeze-fracture electron micrographs of the three liposomal formulations showed unilamellar liposomes with relatively narrow size ranges. However, preincubation of DOPE/DODAC liposomes in 50% mouse serum at 37° C. for 30 minutes resulted in their massive aggregations. On the other hand, both DOPE/DODAC/PEG-Ceramide (C20) and DOPE/DODAC/PEG- DSPE liposomes did not show any aggregation when these liposomes were pretreated with mouse serum. Thus, these results show the effectiveness of the bilayer stabilizing components in preventing serum-induced rapid aggregations of DOPE/DODAC liposomes.

bb. Biodistribution of DOPE/DODAC Liposomes Containing Bilayer

Stabilizing Components, i.e., Amphiphatic PEG Derivatives

DOPE/DODAC liposomes with or without bilayer stabilizing components were prepared to include $^3$H-labelled cholesterolhexadecylether as a lipid marker, and their biodistribution was examined in mice at 1 hour after injection. Liposomes tested in this study were composed of DOPE/DODAC (85:15, mol/mol), DOPE/DODAC/PEG-Ceramide (80:15:5, mol/mol), and DOPE/DODAC/PEG-DSPE (80:15:5, mol/mol). To also examine the effect of the hydrophobic anchor on biodistribution of liposomes, various PEG-Ceramide derivatives with different acyl chain lengths were used. These liposomal formulations had similar average diameters, ranging from 89 to 103 nm. Table II below shows levels of liposomes in the blood, spleen, liver, lung, heart, and kidney, together with respective blood/liver ratios. DOPE/DODAC liposomes were shown to be cleared rapidly from the blood and accumulate predominantly in the liver with the blood/liver ratio of approximately 0.01. Inclusion of bilayer stabilizing components at 5.0 mol % in the lipid composition resulted in their increased blood levels and accordingly decreased liver accumulation to different degrees. DOPE/DODAC/PEG-DSPE liposomes showed the highest blood level (about 59%) and the lowest liver accumulation (about 35%) with the blood/liver ratio of approximately 1.7 at 1 hour after injection. Among various PEG-Ceramide derivatives with different acyl chain lengths, PEG-Ceramide (C20)-containing liposomes showed the highest blood level (about 30%) with the blood/liver ratio of approximately 0.58, while PEG-Ceramide C8)-containing liposomes showed a lower blood level (about 6%) with the blood/liver ratio of approximately 0.1. It appeared that, among different PEG-Ceramide derivatives, the activity in increasing the blood level of liposomes is directly proportional to the acyl chain length of ceramide; the longer the acyl chain length, the greater the activity. It also appeared that the optimal derivative for increasing the blood level of liposomes is PEG-Ceramide (C20).

cc. Optimization of DOPE/DODAC Liposomes for Prolonged Circulation Times

Figure 26:
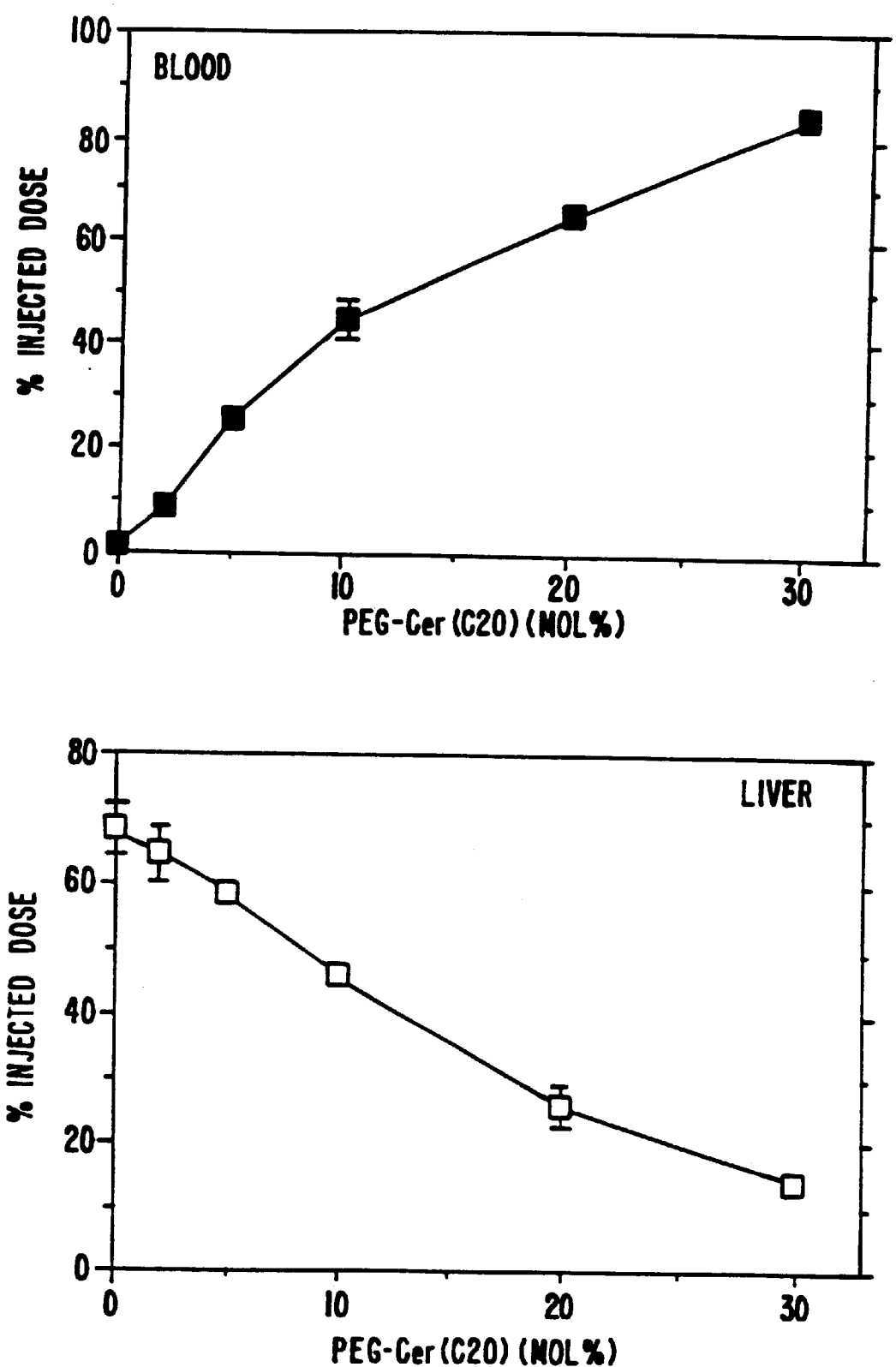
FIG. 26 graphically shows the effect of increasing concentrations of PEG-Ceramide (C20) on liposome clearance from the blood. $^3$H-labeled liposomes composed of DOPE (dioleoylphosphatidylethanolamine), 15 mol % DODAC (N,N-dioleoyl-N,N-dimethylammonium chloride) and the indicated concentrations of PEG-Ceramide (C20) were injected i.v. into mice. Biodistribution was examined at 1 hour after injection, and the data were expressed as a percentage of the injected dose in the blood (upper panel) and liver (lower panel) with SD (standard deviation) (n=3).

The effect of increasing concentrations of PEG-Ceramide (C20) in the lipid composition on biodistribution of DOPE/DODAC liposomes was examined. PEG-Ceramide (C20) was included in DOPE/DODAC liposomes at increasing concentrations (0–30 mol %) in the lipid composition, while the concentration of DODAC was kept at 15 mol % of the lipid mixture. Liposomes were prepared by the extrusion method and had similar average diameters ranging from 102 nm to 114 nm. Liposomes were injected i.v. into mice, and biodistribution was examined at 1 hour after injections. FIG. 26 shows the liposome level in the blood and liver at 1 hour after injections as a function of the PEG-Ceramide (C20) concentration. Clearly, increasing the concentration of PEG-Ceramide in the lipid composition resulted in progressive increase in liposome levels in the blood, accompanied by decreased accumulation in the liver. The highest blood level (about 84% at 1 hour after injection) was obtained for DOPE/DODAC/PEG-Ceramide (C20) (55:15:30, mol/mol) showing the blood/liver ratio of about 6.5.

Figure 27:
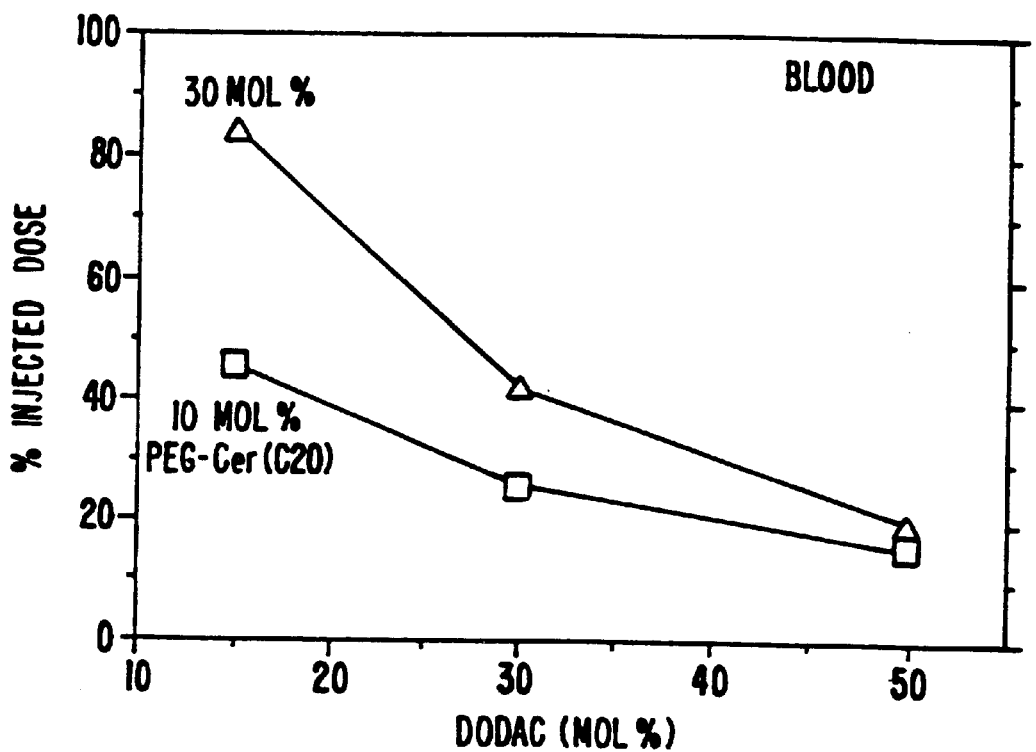
FIG. 27 graphically illustrates the effect of increasing concentrations of DODAC on the biodistribution of liposomes in the blood. $^3$H-labeled liposomes composed of DOPE, 10 (open squares) or 30 (open triangles) mol % PEG-Ceramide (C20), and the indicated concentration of DODAC were injected i.v. into mice. Biodistribution was examined at 1 hour after injection, and the data were expressed as a percentage of the injected dose in the blood.

The effect of increasing concentrations of DODAC on the biodistribution of DOPE/DODAC liposomes also was examined. DOPE/DODAC liposomes containing either 10 mol % or 30 mol % PEG-Ceramide (C20) and various concentrations (15, 30, 50 mol %) were prepared by the extrusion method and had similar average diameters ranging from 103 to 114 nm. Biodistribution was examined at 1 hour after injections, and expressed as percentages of liposomes in the blood as a function of the DODAC concentration (FIG. 27). As shown in FIG. 27, increasing DODAC concentrations in the lipid composition resulted in decreased levels in the blood for both liposomal formulations. Thus, the presence of a cationic lipid, DODAC, in the lipid composition results in rapid clearance from the blood. Also, shown in FIG. 27 is that such a DODAC effect can be counteracted by increasing the concentration of PEG-Ceramide (C20) in the lipid composition.

Figure 28A:
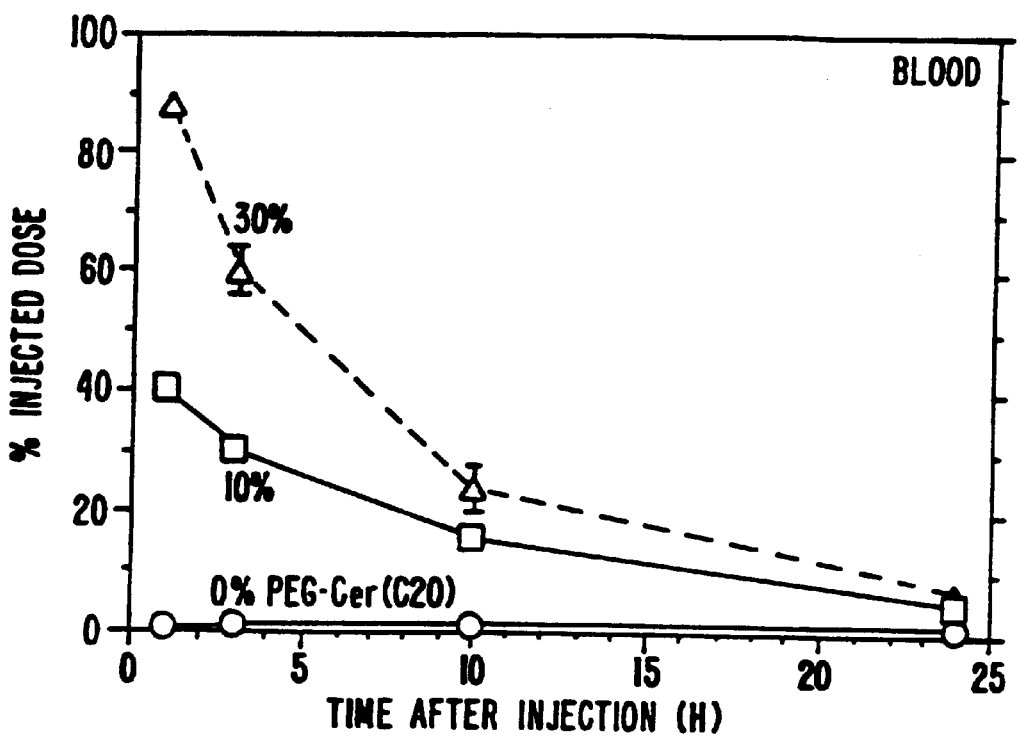
FIG. 28 graphically shows the liposome levels in the blood and liver at different times after injection. $^3$H-labeled liposomes composed of DOPE/DODAC (85:15 mol/mol) (open circles with 0% PEG-Ceramide (C20)), DOPE/DODAC/PEG-Ceramide (C20) (75:15:10 mol/mol/mol) (open squares with 10% PEG-Ceramide (C20)), and DOPE/DODAC/PEG-Ceramide (C20) (55:15:30 mol/mol/mol) (open triangles with 30% PEG-Ceramide (C20)) were injected i.v. into mice. Biodistribution was examined at indicated times, and the data were expressed as a percentage of the injected dose in the blood (FIG. 28A) and in the liver (FIG. 28B) with SD (n=3).
Figure 28B:
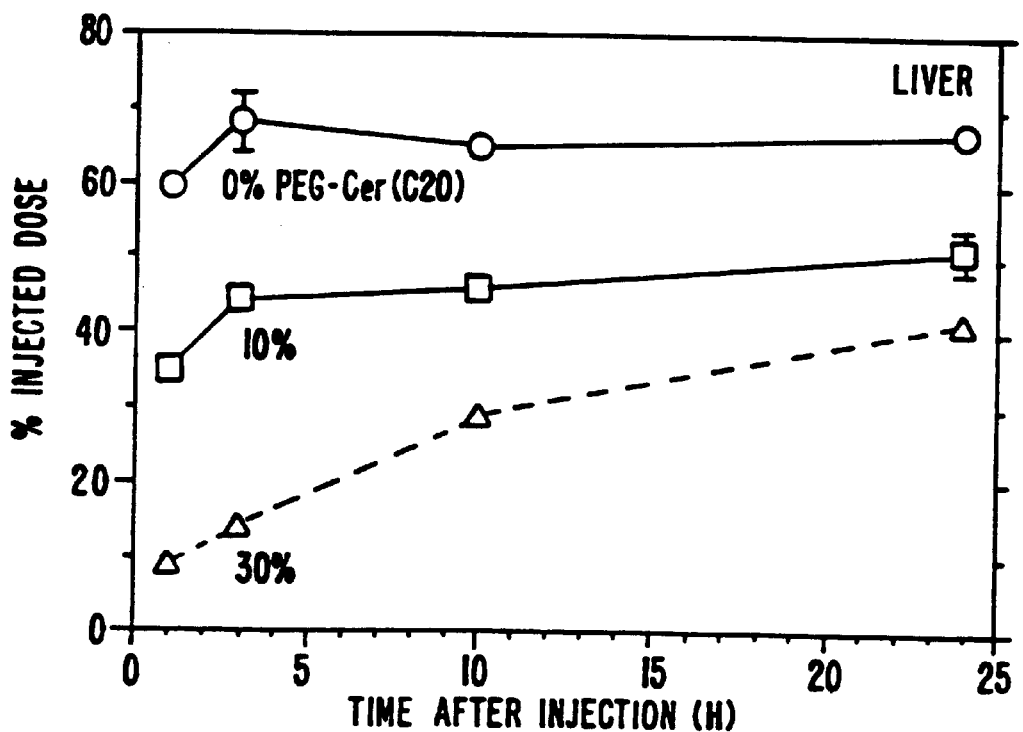
Figure 29:
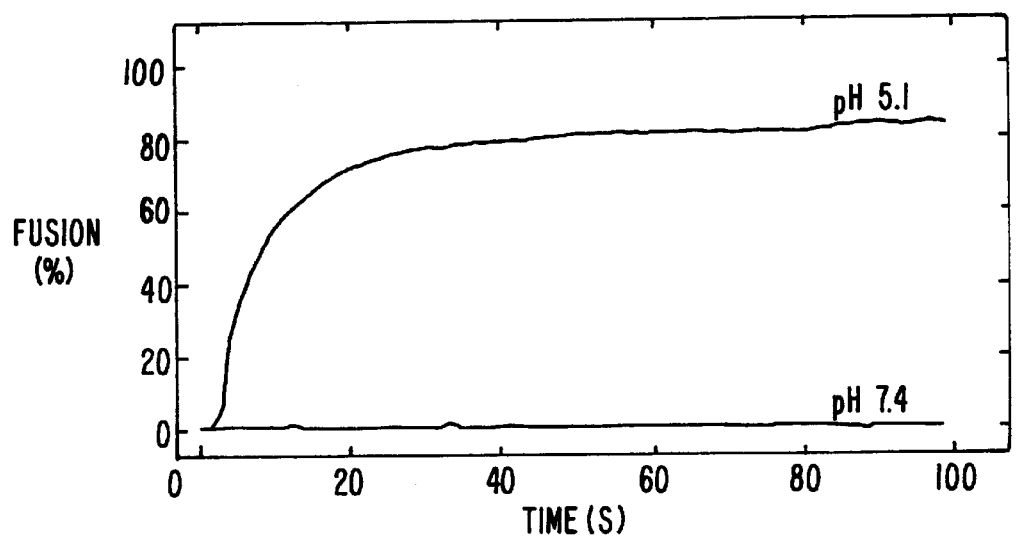
FIG. 29 illustrates that the fusion of reconstituted influenza virosomes with erythrocyte membranes is dependent on low pH.
Figure 30:
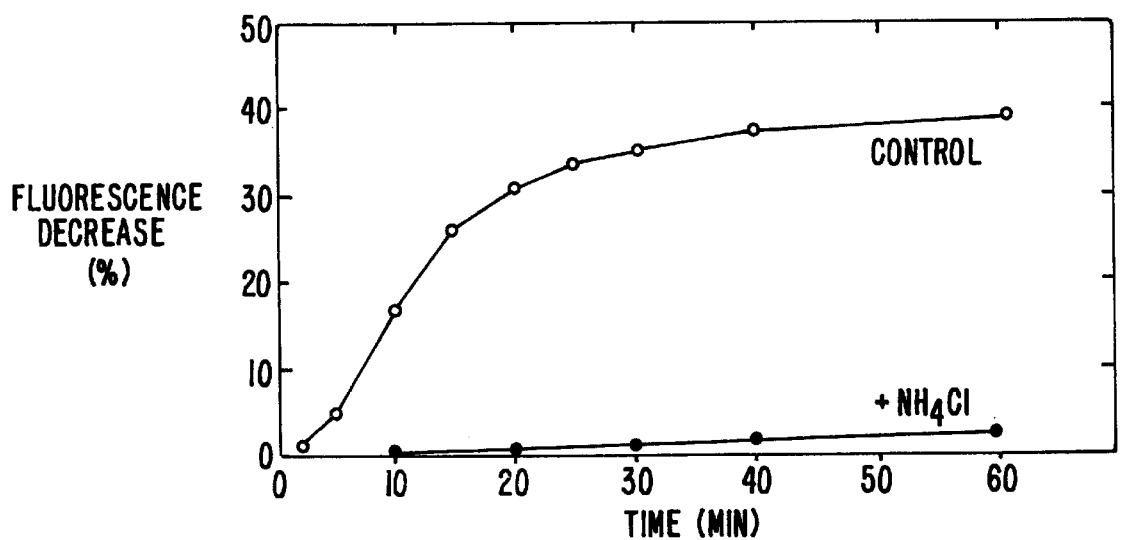
FIG. 30 illustrates the fusion of influenza virosomes from within BHK cell endosomes as monitored by a decrease of pyrene excimer fluorescence and the blocking of fusion by $NH_4Cl$, an inhibitor of endosomal acidification.
Figure 31:
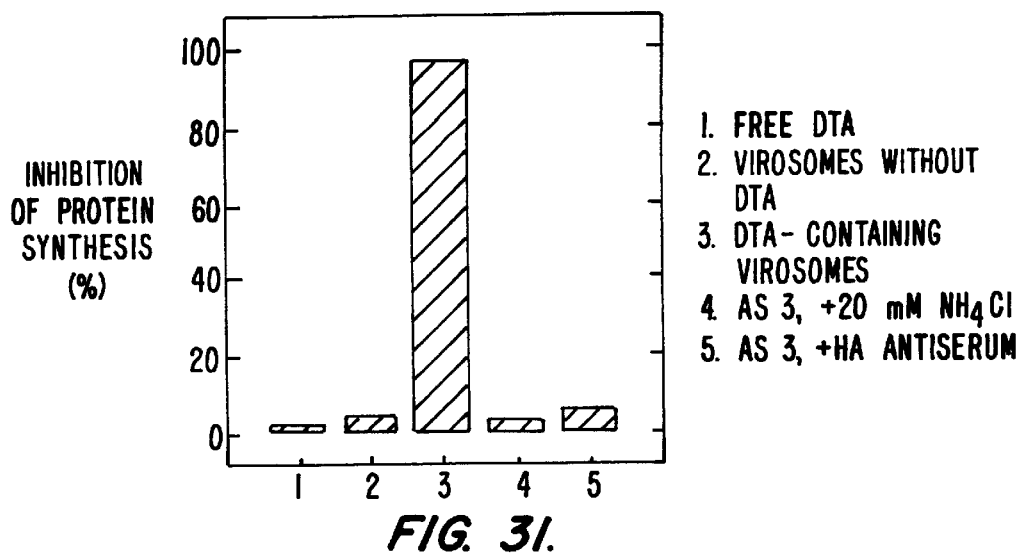
FIG. 31 illustrates that delivery of diphtheria toxin A chain encapsulated in fusogenic virosomes induces complete inhibition of the cellular protein synthesis in BHK-21 cells, whereas free DTA or empty virosomes have no effect on protein synthesis, and that the effect of virosome-encapsulated DTA is blocked completely by $NH_4Cl$, or by pretreatment of the virosomes at low pH causing an irreversible inactivation of their fusion activity.
Figure 32:
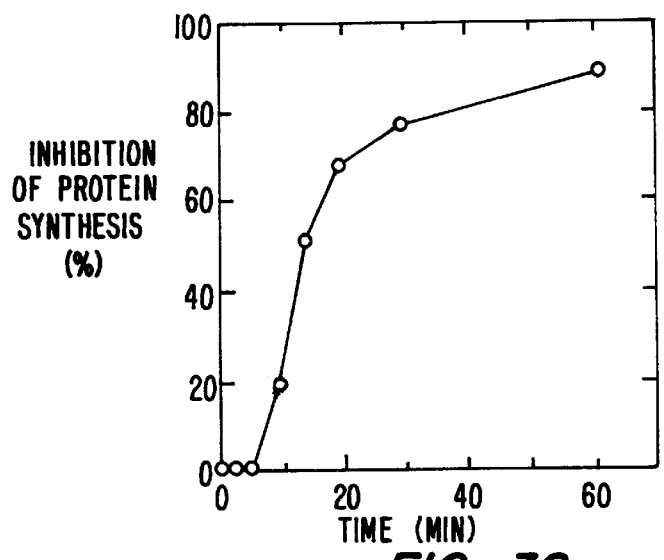
FIG. 32 illustrates the time course of gelonin delivery to BHK cells, as mediated by influenza virosomes fusing from within endosomes.
Figure 33:
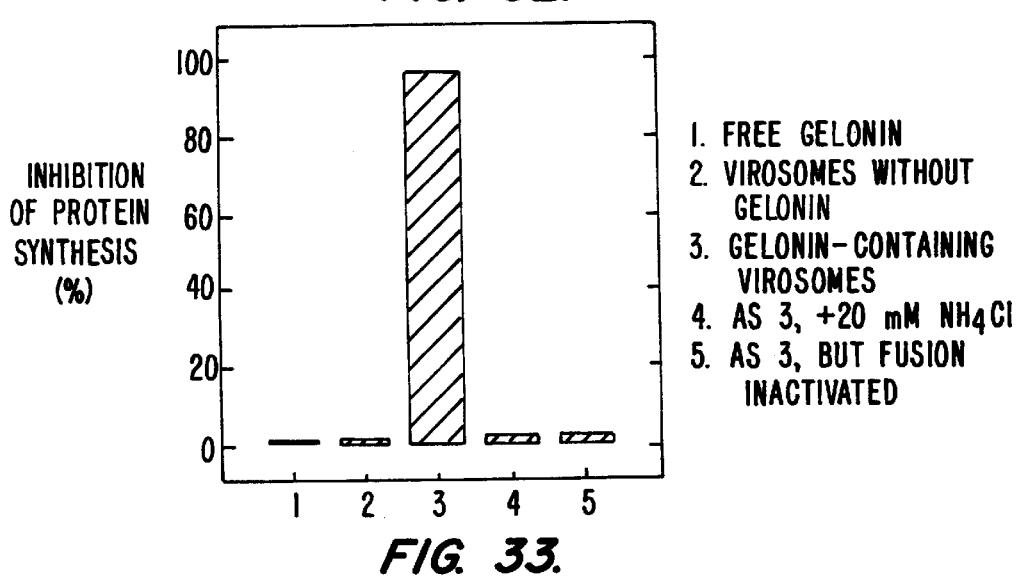
FIG. 33 depicts gelonin delivery to BHK-21 cells mediated by influenza virosomes fusing from within endosomes.
Figure 34:
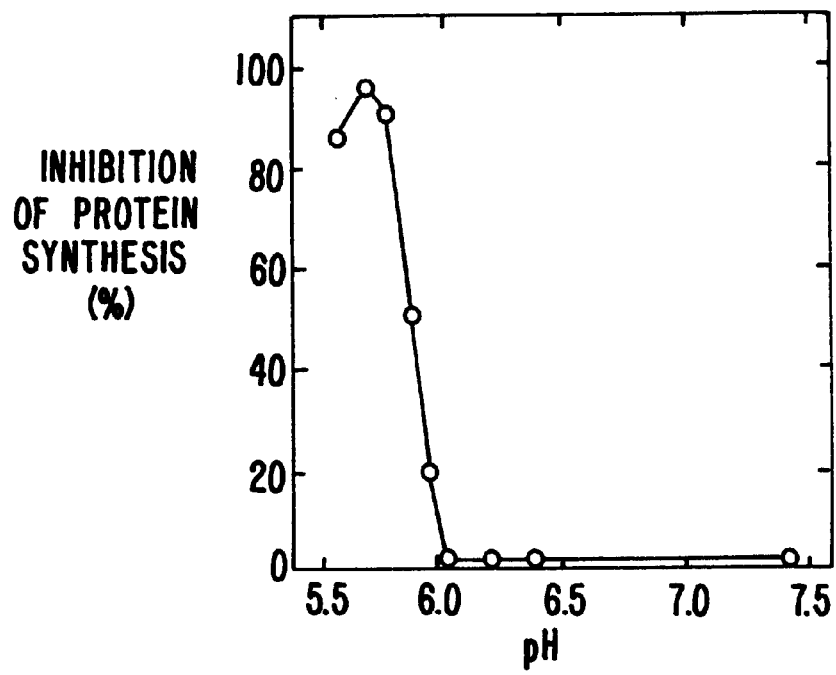
FIG. 34 demonstrates that influenza virosomes can fuse with the plasma membrane of BHK cells, thereby mediating intracellular delivery of encapsulated gelonin.
Figure 35:
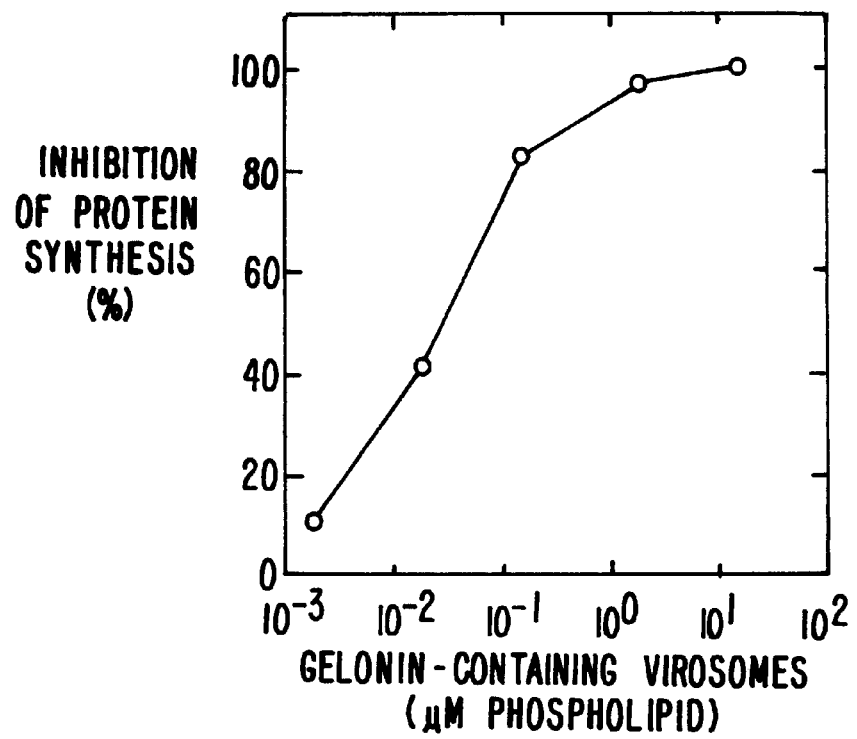
FIG. 35 illustrates titration of gelonin-mediated inhibition of protein synthesis to a level corresponding to a single virosome fusing per cell.
Figure 36:
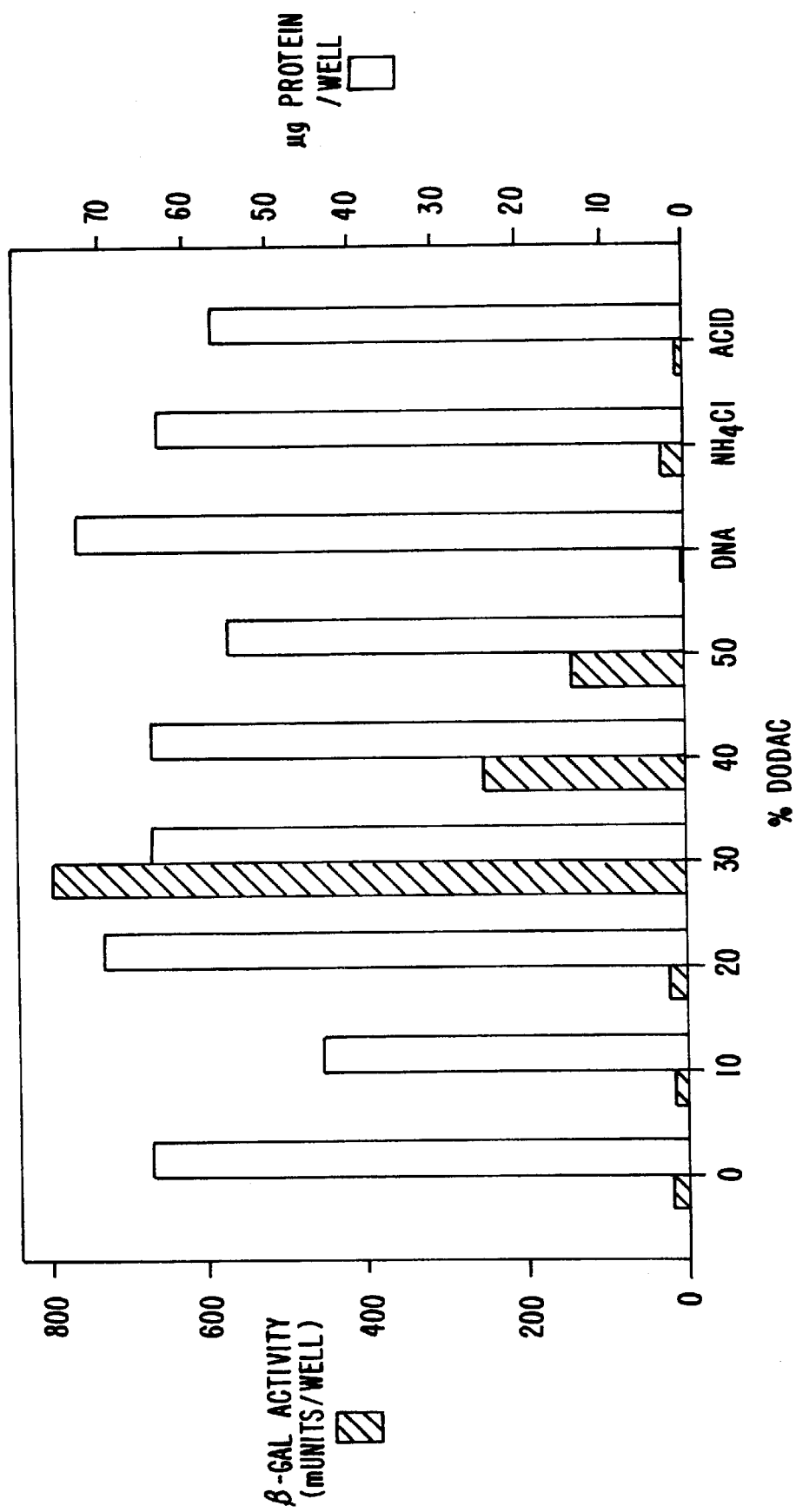
FIG. 36 shows the expression of β-Gal in transfected BHK cells as a function of % DODAC in the fusion protein TCS.
Figure 37:
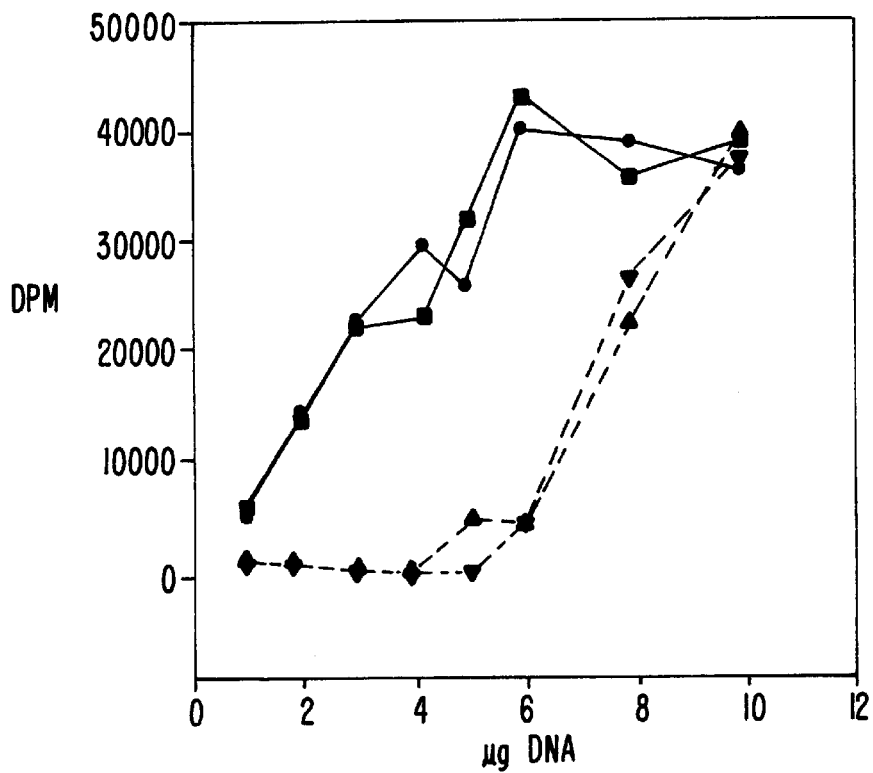
FIG. 37 shows the DNA binding capacity of the virosomes containing 30 mol % DODAC, where increasing amounts of $^3$H-pCMVβ-gal were added to virosomes and, after incubation and centrifugation, radioactivity determined in the pellet (●, ■) and in the supernatant (▲, ▼) of two independent experiments.
Figure 38:
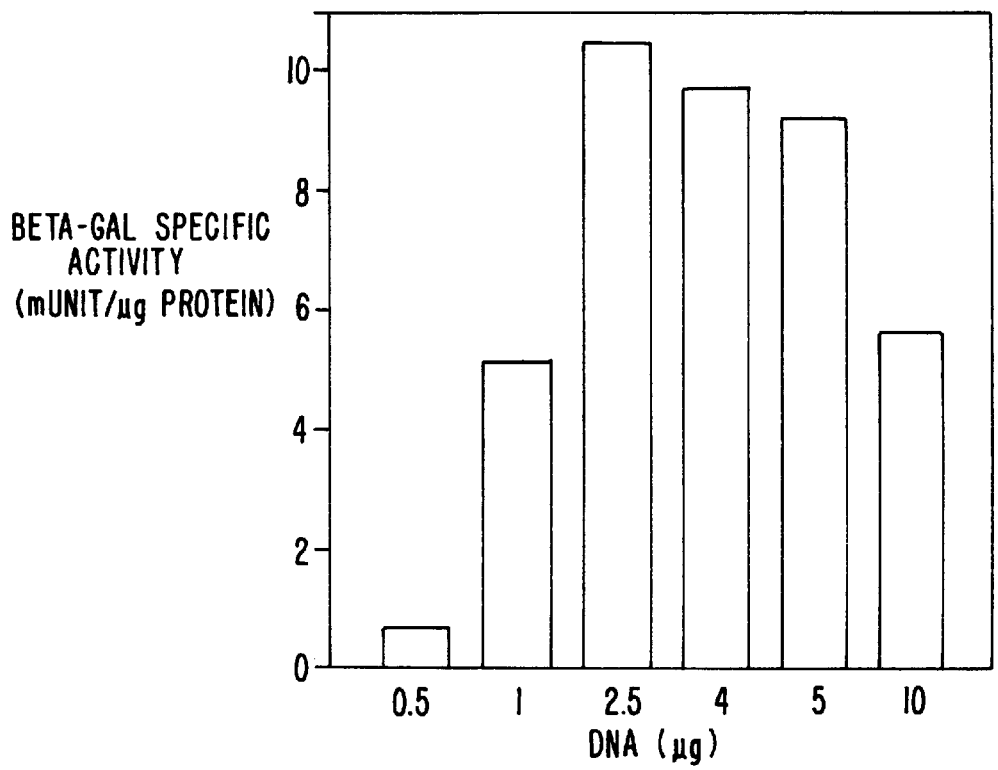
FIG. 38 shows the expression of β-Gal in transfected BHK cells as a function of DNA added per well complexed to virosomes.

FIG. 28 shows time-dependent clearances of DOPE/DODAC liposomes with or without PEG-Ceramide from the blood. Only a small fraction of injected DOPE/DODAC liposomes remained in the blood, while increasing the concentration of PEG-Ceramide (C20) in the lipid composition resulted in prolonged circulation times in the blood. Estimated half-lives in the α-phase for DOPE/DODAC/PEG-Ceramide (C20) (75:15:10, mol/mol) and DOPE/DODAC/PEG-Ceramide (C20) (55:15:30, mol/mol) were <1 hour and 5 hours, respectively.

iii. Conclusions

The above studies indicate that there are several levels at which biodistribution of fusogenic liposomes containing a cationic lipid can be controlled by inclusion of bilayer stabilizing components. Data in Table II shows that the hydrophobic anchor of the bilayer stabilizing components has an important role in determining biodistribution of DOPE/DODAC liposomes. Studies using various PEG-Ceramide derivatives with different acyl chain lengths showed that the longer the acyl chain length of PEG-Ceramide, the greater the activity in prolonging the circulation time of DOPE/DODAC liposomes. These results are consistent with the rate at which the bilayer stabilizing components dissociate from the liposome membrane being directly proportional to the size of the hydrophobic anchor. Accordingly, PEG-Ceramide derivatives with a longer acyl chain can have stronger interactions with other acyl chains in the liposome membrane and exhibit a reduced rate of dissociation from the liposome membrane, resulting in stabilization of DOPE/DODAC liposomes for a prolonged period of time and thus their prolonged circulation time in the blood.

In addition to the hydrophobic anchor of the bilayer stabilizing components, the concentration of the bilayer stabilizing components in the lipid membrane can also be used to control in vivo behavior of DOPE/DODAC liposomes. Data in FIG. 26 show that increasing the concentration of PEG-Ceramide (C20) in the lipid composition resulted in increased liposome levels in the blood.. The optimal concentration of PEG-Ceramide (C20) in the lipid composition was found to be 30 mol % of the lipid mixture. It appeared that the circulation time of DOPE/DODAC/PEG-Ceramide (C20) liposomes is determined by the relative concentrations of two lipid compositions, DODAC and PEG-Ceramide, exhibiting opposite effects on liposome biodistribution. While bilayer stabilizing components exhibit the ability to prolong the circulation time of liposomes in the blood, a cationic lipid, DODAC, exhibits the ability to facilitate liposome clearance from the blood. Thus, for the maximal circulation time in the blood, an appropriate concentration of a bilayer stabilizing component and a minimal concentration of DODAC should be used. It should be noted, however, that an optimal liposome formulation for the prolonged circulation time in the blood is not necessarily the one suitable for an intended application in delivery of certain therapeutic agents. Both pharmacokinetic and pharmacodynamic aspects of fusogenic liposomes should be examined for different applications using different therapeutic agents.

tography using 10% ethyl acetate in hexane as eluant. Two hundred milligrams of this material (0.28 mmol) and 32 mg of N-hydroxysuccinimide (0.29 mmol) were dissolved in 5 ml of $CH_2Cl_2$ and 57 mg of 1,3-dicyclohexylcarbodimide (0.28 mmol) was added with stirring. The reaction was allowed to proceed for one hour at room temperature after which the mixture was filtered to remove precipitate,. and the solvent was removed by rotary evaporation yielding the activated lipid (3). A mixture of 5.6 mg of the peptide

TABLE II

Effect of Amphipathic PEG Derivatives on Biodistribution of DOPE/DODAC Liposomes

| PEG-Derivative | Average Diameter (nm) | % injected dose | | | | | | | |
|---|---|---|---|---|---|---|---|---|---|
| | | Blood | Liver | Spleen | Lung | Heart | Kidney | Total | Blood/Liver |
| None | 103 (29) | 0.8 (0.4) | 64.4 (2.0) | 3.1 (1.8) | 1.2 (0.2) | 0.2 (0.0) | 0.3 (0.0) | 70.0 (1.4) | 0.012 |
| PEG-DSPE | 95 (26) | 59.1 (8.2) | 34.7 (2.1) | 2.9 (0.1) | 1.9 (0.8) | 1.7 (0.4) | 1.2 (0.5) | 101.4 (6.1) | 1.703 |
| PEG-Cer (C8) | 89 (24) | 6.5 (1.9) | 62.8 (3.4) | 4.2 (1.0) | 0.5 (0.3) | 0.3 (0.1) | 0.3 (0.1) | 74.6 (5.1) | 0.104 |
| PEG-Cer (C14) | 93 (25) | 5.9 (0.5) | 55.9 (1.0) | 3.3 (0.2) | 0.1 (0.0) | 0.1 (0.0) | 0.1 (0.0) | 65.4 (1.6) | 0.106 |
| PEG-Cer (C16) | 93 (24) | 13.9 (2.1) | 57.5 (2.0) | 2.6 (0.1) | 0.0 (0.0) | 0.2 (0.1) | 0.0 (0.0) | 74.3 (4.0) | 0.242 |
| PEG-Cer (C20) | 101 (24) | 29.8 (4.8) | 51.0 (2.2) | 1.9 (0.2) | 0.0 (0.0) | 0.3 (0.1) | 0.0 (0.0) | 82.8 (2.8) | 0.584 |
| PEG-Cer (C24) | 92 (28) | 26.7 (0.8) | 46.7 (7.6) | 5.7 (1.2) | 1.0 (0.2) | 0.9 (0.2) | 0.4 (0.1) | 81.5 (4.1) | 0.572 |

[3]H-labelled liposomes composed of DOPE/DODAC (75:15, mol/mol) additionally containing an indicated PEG derivative at 5.0 mol % of the lipid mixture were injected i.v. into mice. Biodistribution was examined at 1 h after injection and expressed as percentage of injected dose of liposomes with SD (n = 3).

B. Examples Relating to the Fusogenic Liposomes Containing Lipopeptides
1. Materials and General Methods
   a. Lipids and Chemicals Crude peptide was obtained from the laboratory of Dr. Ian Clark-Lewis, Biomedical Research Laboratory, University of British Columbia. Subsequently, purified peptide was purchased from Multiple Synthesis (CA). 1,2-Distearoyl-sn-glycerol (DSG), 1-Palmitoyl-2-oleoyl-sn-phosphatidylcholine (POPC, egg phosphatidylcholine (EPC), N-(7-nitro-2,1,3-benzoxadiazol-4-yl)-4-yl)-1,2-dioleoyl-sn-phosphatidylethanolamine(NBD-PE), and N-(lissamine rhodamine B sulphonyl)-1,2-dioleoyl-sn-phosphatidylethanolamine (Rh-PE) were supplied by Avanti Polar Lipids (Alabaster, Ala.). Aminonaphthalenetrisulphonic acid (ANTS) and p-xylylenebis-(pyridinium) bromide (DPX) were purchased from Molecular Probes (Eugene, Oreg.). Succinic anhydride, 4-dimethylaminopyridine, N-hydroxysuccinimide, dicyclohexylcarbodiimide, cholesterol and all buffers were purchased from Sigma Chemical Co. (St. Louis, Mo.). HPLC-grade organic solvents and miscellaneous chemicals were supplied by Fisher Scientific.

b. Preparation of AcE4K and Lipo-AcE4K

After lyophilization, the peptide was purified by reverse-phase HPLC on a Synchropak (Synchrom, Inc.) C8 semi-preparative HPLC column using a 40%–70% linear gradient of acetonitrile in water (0.1% TFA) with a flow rate of 6 ml/minute over 20 minutes. The peptide elutes at approximately 55% acetonitrile. Composition and purity of the peptide were verified by amino acid analysis, mass spectrometry and HPLC. Purity was estimated to be greater than 95% .

The synthesis of the lipopeptide is illustrated in FIG. 40. One gram of 1,2-distearoyl-sn-glycerol (1.6 mmol) (I), 0.2 g succinic anhydride (2 mmol), and 0.24 g 4-dimethylaminopyridine (2 mmol) were dissolved in 10 ml of $CH_2Cl_2$ and stirred at room temperature for one hour. The resulting acid (2) was isolated by removing solvent by rotary evaporation followed by purification by silica gel chroma- AcE4K (2.5 µmol), 4.1 mg of 3 (5.0 µmol) and 15 mg of triethylamine in 1 ml of dimethylsulfoxide (DMSO) was heated to 65° C. to achieve co-dissolution of the lipid and peptide and incubated for one hour. After cooling, the lipopeptide (4) was precipitated by the addition of 5 ml of diethyl ether and centrifuged at 2000 rpm for 5 minutes. The pellet was washed three times with 2 ml of diethyl ether repeating the centrifugation with each wash. The lipopeptide was dried under vacuum and its identity was confirmed by mass spectrometry. Purity as determined by peptide-to-lipid ratio using $^1$H-NMR was found to be greater than 95%.

c. Preparation of Liposomes

Chloroform solutions of lipids were dried by vortex mixing under nitrogen followed by the removal of residual solvent under high vacuum for 1 hour. When lipopeptide was incorporated into the liposome preparations, it was added to the dried lipids as a 1 mM solution in DMSO along with an equal volume of benzene-methanol (95:5) prior to freeze-drying for 5 hours. Lipids were hydrated with appropriate buffers to concentrations ranging from 5 to 20 mM lipid. Five freeze-thaw cycles were used to ensure homogeneous mixture of the multilamellar vesicle (MLV) suspensions. The MLVs were extruded 10 times through two 100 nm pore-size polycarbonate filters (Costar, Cambridge, Mass.) to produce large unilamellar vesicles (LUVs). Lipid concentrations were determined by phosphate assay as described previously (see, e.g., Bartlett, G. R., *J. Biol. Chem.*, 234:466–68 (1959)). Depending on the lipid formulation, the mean diameter of the LUVs ranged from 100 to 135 nm as measured by quasi-elastic light scattering.

d. Circular Dichroism

Differences in the secondary structure of AcE4K and Lipo-AcE4K as a function of pH were investigated by CD spectropolarimetry. A solution of AcE4K was initially dissolved in 10 mM phosphate buffer, pH 7.5, at a concentration of 0.5 mM. Subsequently, 200 µl samples were prepared by diluting this stock to a peptide concentration of 25 µM in 10 mM phosphate buffer at either pH 5.0 or pH 7.5. CD spectra over wavelengths of 200 to 250 nm were recorded on a Jasco J720 Spectropolarimeter using a 1 mm quartz cuvette and accumulations of five scans. To obtain spectra in the presence of lipid bilayers, POPC LUVs were used at a concentration of 2.5 mM lipid (lipid/peptide ratio=100) prepared in 10 mM phosphate buffer adjusted to either pH 7.5 or pH 5.0. Under these conditions, the CD spectra of the peptide could be measured in the presence of lipid bilayers with minimal difficulties arising from absorbance and scattering due to the lipid. The spectra obtained were corrected by subtracting lipid or buffer signal, as appropriate.

For the lipopeptide, LUVs were prepared with 1% Lipo-AcE4K in POPC at a phospholipid concentration of 2.5 mM in 10 mM phosphate buffer adjusted to either pH 5.0 or pH 7.5. CD spectra were obtained as above. The very low solubility of the lipopeptide prevents measurements ia the absence of lipid.

e. Tryptophan Fluorescence

Tryptophan fluorescence spectra were recorded with an excitation wavelength of 280 nm over an emission range of 300 to 400 nm on a Perkin Elmer LS50 fluorometer using a 1 cm quartz cuvette thermostatted at 25° C. For the free peptide, the aqueous stock solution was diluted to 100 µM and 30 µl of this was added to 10 mM phosphate buffer at pH 7.5 or pH 5.0, either with or without POPC LUVs (0.1 mM phospholipid, lipid/peptide ratio=100), for a total sample volume of 3 ml. Spectra of the lipopeptide incorporated into liposomes were obtained using the Lipo-AcE4K/POPC LUVs described above diluted to 0.1 mM POPC, 1.0 µM Lipo-AcE4K. The spectra were corrected by subtracting scans of phosphate buffer or LUVs, as appropriate.

f. Preparation of Erythrocyte Membranes

Sealed erythrocyte ghosts were prepared by the method of Steck and Kane, supra (1974). Briefly, 4 ml of packed cells was washed 3 times with HEPES buffered saline (HBS: 5 mM HEPES, 150 mM NaCl, pH 7.5), centrifuging each for 5 minutes at 2000 rpm in a swinging-bucket rotor. Washed cells were diluted 2-fold with HBS, lysed in 300 ml of mM HEPES, 1 mM MgCl$_2$, pH 7.5, and pelleted at 20,000 g for 20 minutes. Ghosts were removed from above the hard, protease-rich pellet and resuspended in 200 ml of HBS containing 1 mM MgCl$_2$. The suspension was repelleted and washed twice more and finally resuspended in 10 ml of HBS. Phospholipid concentration was determined by phosphate assay. The absence of glyceraldehyde-3-phosphate dehydrogenase activity (Steck & Kant, supra, 1974) was used to confirm the formation of sealed right-side-out ghosts.

g. Lipid-Mixing Fusion Assays

The extent of membrane fusion as measured by lipid mixing in the presence of AcE4K and Lipo-AcE4K was monitored by the decrease in resonance energy transfer (RET) resulting from dual fluorescent probe dilution (Struck, et al., Biochemistry, 20:4093–4099 (1981)). LUVs of a desired lipid composition containing of 0.5 mol % of both NBD-PE and NBD-PE were prepared in HMA buffer (10 mM HEPES, 10 mM MES, 10 mM sodium acetate, 100 mM NaCl), pH 7.5. AcE4K was added to labeled vesicles from a 1 mM aqueous solution at pH 7.5. Lipo-AcE4K was either included in the lipid preparation as described above or added to labeled vesicles from a 1 mM solution in DMSO. Labeled vesicles were mixed with either unlabelled LUVs or erythrocyte ghosts in a lipid ratio of 1:3 at a total lipid concentration of 0.2 mM. Typically, 15 µl 10 mM labeled LUVs and 45 µl of 10 mM unlabelled LUVs or 300 µl of erythrocyte ghosts were made up to 3 ml in a 1 cm quartz cuvette with a HMA buffer, pH 7.5. Fluorescence was monitored at 25° C. over 5 minutes with excitation at 465 nm, emission at 535 nm, and an emission cut-off filter at 530 nm. During the assays, 1 M HCl was added to decrease the pH to a desired value. (HMA buffer has a linear pH response to acid volume over the pH range 4.0 to 7.5.)

Each point in the lipid-mixing timecourse was normalized by subtracting the fluorescence of a comparable assay lacking unlabelled vesicles ($F_0$ and dividing by the fluorescence achieved by infinite probe dilution determined by the addition of 25 µl of 100 mM Triton X-100 ($F_{max}$). The percent change in fluorescence was calculated as $$\% \frac{\Delta F}{\Delta F_{max}} = 100 \times \left( \frac{F - F_0}{F_{max} - F_0} \right)$$

for each point in the timecourse. Complete lipid mixing, as determined by a liposome preparation corresponding to a 1:3 ratio of labeled to unlabelled vesicles, gives a value of $\Delta F/\Delta F_{max}$ of approximately 80% under these conditions. Reported results were not corrected by this factor.

h. Exchange of Lipo-AcE4K Between Membranes

POPC MLVs were prepared in HMA buffer at pH 7.5 as described above and pelleted at 12,000 rpm on a benchtop centrifuge at 5° C. The pellet was resuspended in HMA buffer and repelleted, and this procedure was repeated for three washings to ensure removal of any small lipid vesicles prior to determination of lipid concentration by phosphate assay. Thirty microlitres of POPC LUVs (10 mM lipid) was diluted in 1.09 ml of HMA buffer, pH 7.5, and 7.5 µl of 2 mM Lipo-AcE4K was added from DMSO stock. This preparation results in the incorporation of 10 mol % of the lipopeptide into the outer monolayer of the LUVs. After a 5 minute pre-incubation at 25° C., 375 µl of 12.5 mM POPC MLVs were added as a sink for lipopeptide exchange. This 60-fold lipid excess represents a 3-fold excess of available sink, assuming 5% of the MLV lipid is exposed on the outermost monolayer. Following a five minute incubation at 25° C., the MLVs were pelleted as above and the peptide and lipid content (phosphate assay) of the supernatant was determined. A micro-BCA assay kit as provided by Pierce Chemical Co. was used with the provided procedure to analyze for peptide. The results were compared to controls without MLVs or without Lipo-ACE4K.

i. Contents Mixing and Leakage

Liposomes of a desired composition were prepared containing either 25 mM ANTS in HMA buffer, 100 mM DPX in HMA buffer, or 6 mM ANTS plus 75 mM DPX (ANTS-DPX), at pH 7.5 as described above. External buffer was exchanged with HMA buffer on Sephadex G-25 columns prior to diluting to 10 mM lipid. To assay for contents mixing, 15 µl of the ANTS preparation on 45 µl of DPX liposomes were combined in 3 ml of HMA buffer. ANTS fluorescence was monitored over 5 minutes with the addition of 15 µl of 1 M HCl at 30 seconds to decrease the pH to 5.0. Excitation and emission wavelengths were 360 nm and 530 nm, respectively, and a 490 nm cut-off filter was used. Maximum quenching and zero leakage was determined by the fluorescence of the preparation containing both ANTS and DPX, and zero quenching was measured using only ANTS liposomes, both prior to the addition of acid. Leakage was quantified by comparing the maximum quenching result (0% leakage) with a similar assay to which 25 µl of 100 mM Triton X-100 was added (100% leakage).

j. Freeze-Fracture Electron Microscopy

LUVs consisting of 10 mol % Lipo-AcE4K in EPC/Chol (55:45) were prepared in HMA buffer, pH 7.5, at a total lipid concentration of 5 mM. A sample at pH 5.0 was prepared by adding 1.5 µl of 1 M HCl to 100 µl of liposomes. After 5 minute incubations at 25° C., samples at each pH were mixed 1:1 with glycerol and quickly frozen. Platinum/carbon replicas were prepared as described previously (Fisher & Branton, 1974). EPC/Chol (55:45) liposomes at pH 7.5 and 5.0 were used as controls.

k. Fluorescence Microscopy

To confirm lipid mixing of Lipo-AcE4K LUVs with erythrocyte membranes, the appearance of Rh-PE fluorescence in the erythrocyte membranes upon acidification was demonstrated. The dual-labeled liposome preparation as described above for the lipid mixing assay was used. One hundred microlitres of 2.5 mM LUVs and 10 μl of 0.25 mM Lipo-AcE4K in DMSO were added to 615 μl of HMA buffer, pH 7.5. After a 5 minute preincubation, a 3-fold lipid excess of erythrocyte ghosts (250 μl of 3 mM lipid) was added. This mixture contained 1 mM total lipid with 10 mol % Lipo-AcE4K incorporated into the outer monolayers of the LUVs, or five times the concentrations used in the lipid mixing assays. A 5 μl aliquot was removed prior to acidification with 15 μl of 1 M HCl, reducing the pH to 5.0. Samples at each pH were inspected by confocal microscopy using both phase-contrast and fluorescence techniques.

2. Experimental Results a. Solubilities of AcE4K and Lipo-AcE4K

The highly hydrophobic nature and low solubility of natural viral fusion peptides is problematic in studying their interactions with lipid vesicles. The peptide AcE4K was soluble in aqueous solutions at pH 7.5 at concentrations up to 10 mM and highly soluble in DMSO. The use of the C-terminal lysine residue to couple the peptide to the lipid anchor, rather than the more commonly used cyteine-thioether chemistry, overcame earlier difficulties which existed with purifying the corresponding C-terminal cysteine peptide. The lipopeptide Lipo-AcE4K was soluble only in DMSO and was added to assays from a 2 mM stock solution such that the amount of organic solvent was less than one percent by volume.

b. Circular Dichroism and Tryptophan Fluorescence

Figure 39:
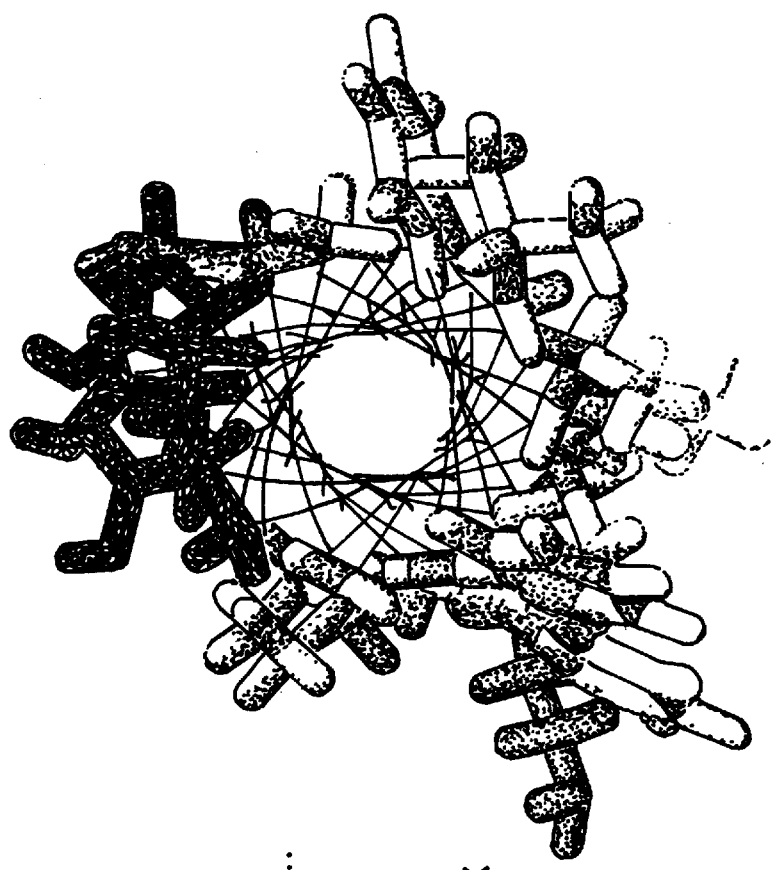
FIG. 39 illustrates the amino acid sequence of the hemagglutinin HA2 subunit N-terminal "fusion peptide" of influenza virus X31 strain (wt) (SEQ ID NO:1), sequence of the E4 peptide (SEQ ID NO:2) prepared by Rafalski, et al. (*Biochemistry*, 30:10211–10220 (1991)) containing a glutamic acid substitution at position 4, and sequence of the peptide AcE4K (SEQ ID NO:3), used in this study, including N-terminal acetylation and the addition of lysine-21 at the C-terminus. A representation of AcE4K as an α-helix with acidic sidechains shown in black and hydrophobic residues in white demonstrates the potential amphipathic nature of the peptide in this conformation.
Figure 41A:
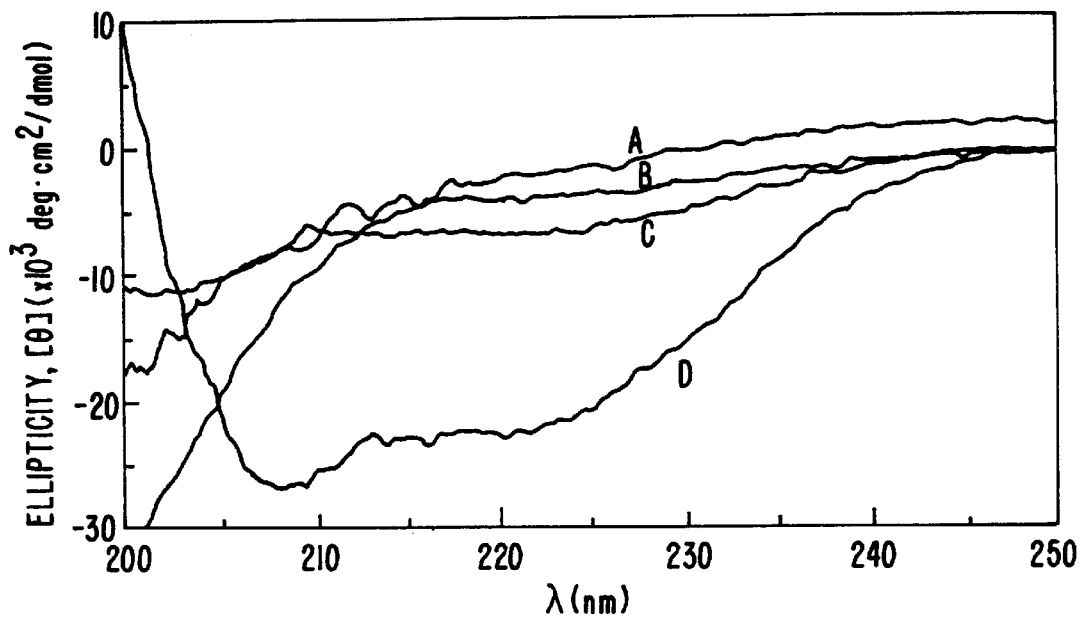
FIG. 41A: CD spectra of 25 μM AcE4K in 10 mM phosphate buffer at pH 7.5 (A, C) and pH 5.0 (B, D) in the absence (A, B) or presence (C, D) of POPC LUVs, 2.5 mM lipid.
Figure 41B:
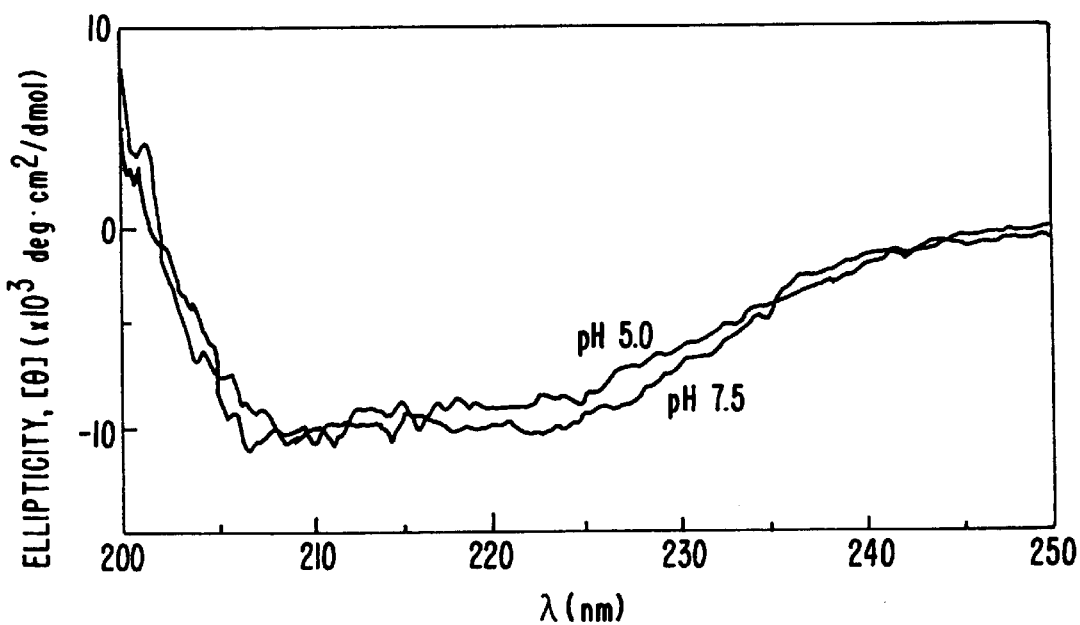
FIG. 41B: CD spectra of POPC LUVs (2.5 mM lipid) prepared with 1 mol % Lipo-AcE4K in phosphate buffer at pH 7.5 or pH 5.0. All spectra represent the average of 5 scans from which buffer and lipid signal has been subtracted, as appropriate.

Differences in the secondary structure of AcE4K and Lipo-AcE4K as a function of pH were investigated by CD spectropolarimetry. CD spectra of AcE4K and Lipo-AcE4K are given in FIG. 41. The behavior of the lipopeptide as a function of pH is markedly different from the free peptide. AcE4K has a random coil structure at neutral pH either in the presence or absence of POPC LUVs (FIG. 41(A)). At pH 5.0, the random coil signal persists in the absence of lipid membranes. However, in the presence of POPC LUVs at pH 5.0, AcE4K adopts a highly α-helical structure, characterized by the signal minima at 208 nm and 222 nm. This result suggests that AcE4K can exist as a amphipathic helix, much like the structure given in FIG. 39, and that it does so only upon neutralization of its acidic residues and in the presence of lipid bilayers. In contrast, the structure of the peptide in Lipo-AcE4K does not appear to be affected by pH (FIG. 41(B)). At pH 7.5, the lipopeptide already exists in a partly α-helical conformation and the CD spectrum is not changed at pH 5.0. This difference in behavior for the peptide in its free and lipid-coupled form are surprising, but these results do not provide any information on the degree of interactions of the peptides with the lipid bilayer or their effects on membrane stability.

Figure 42A:
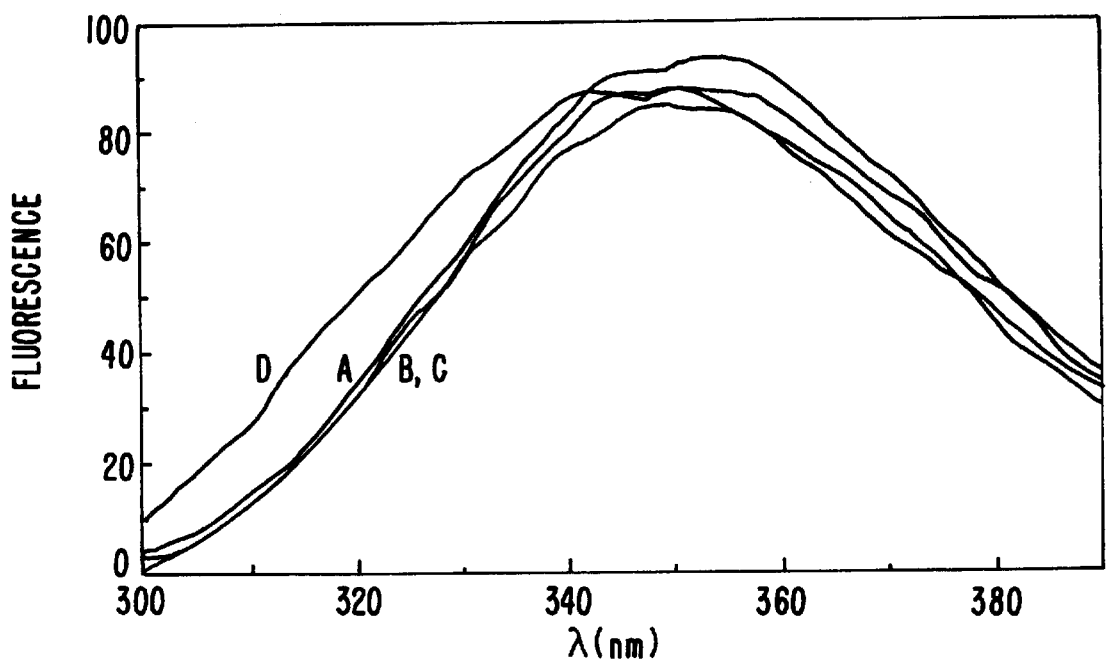
FIG. 42A: 1 μM AcE4K in 10 mM phosphate buffer at pH 7.5 (A, C) and pH 5.0 (B, D) in the absence (A, B) or presence (C, D) of POPC LUVs, 0.1 mM lipid.
Figure 42B:
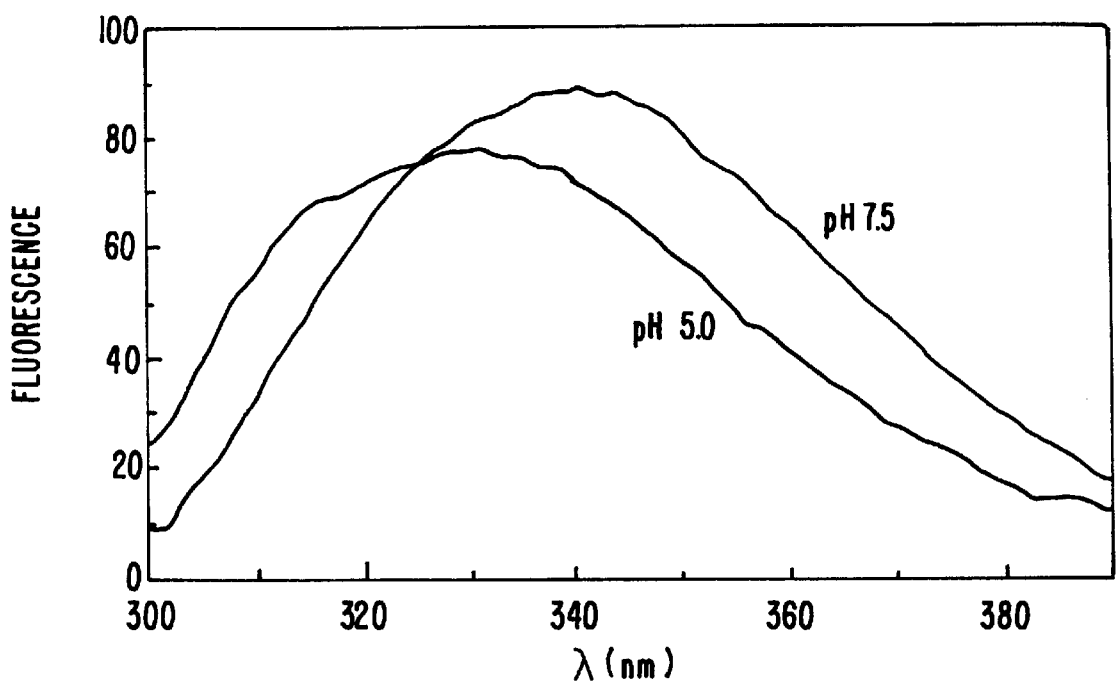
FIG. 42B: POPC LUVs (0.1 mM lipid) prepared with 1 mol % Lipo-AcE4K in phosphate buffer at pH 7.5 or pH 5.0. Spectra were corrected by subtracting scans of phosphate buffer or LUVs, as appropriate.
Figure 43:
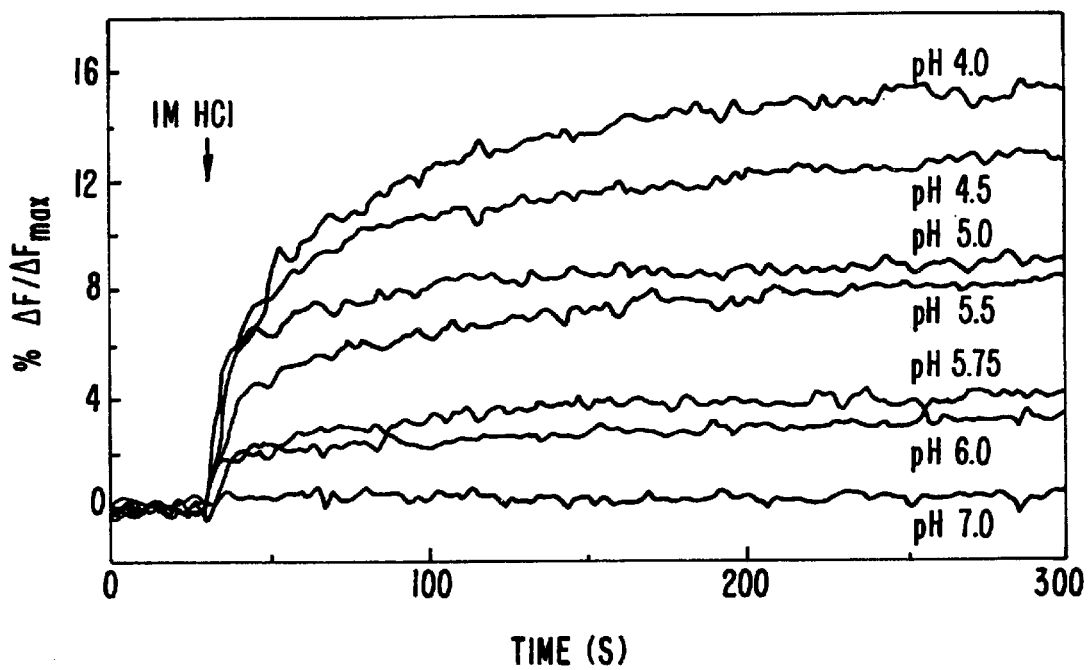
FIG. 43 illustrates the effect of pH on lipid mixing for 5 mol % Lipo-AcE4K in POPC LUVs. Lipopeptide was added from a 2 mM DMSO stock solution to a 1:3 mixture of labelled and unlabelled vesicles prior to the addition of 1 M HCl to achieve the indicated pH.

The penetration of peptides bearing tryptophan or tyrosine residues into lipid bilayers can be monitored by the fluorescence emission spectra of these amino acid residues. Collisional quenching of fluorescence caused by water when the residues are exposed to aqueous medium is reduced upon membrane penetration. This is accompanied by a blue shift in the maximum of fluorescence emission resulting from the reduced polarity of the medium. AcE4K contains a single tryptophan residue at position 14 and has no tyrosine residues. The fluorescence spectrum of tryptophan-14 can, therefore, be used as a measure of membrane penetration. The spectral of AcE4K at pH 7.5 and 5.0 in the presence and absence of POPC LUVs are given in FIG. 42(A). No differences are observed, except for the sample at pH 5.0 in the presence of vesicles which exhibits a slight blue shift of $\lambda_{max}$ and a significant increase in intensity at shorter wavelengths. In contrast to this, the spectra for Lipo-AcE4K in POPC vesicles shown in FIG. 42(B) indicate that, even at pH 7.5, the tryptophan residue is somewhat protected from the aqueous medium having a $\lambda_{max}$ of 340 nm compared to 355 nm for the free peptide. At pH 5.0, the $\lambda_{max}$ is further reduced to 332 nm. This result suggests that, while no structural changes in the peptide were observed in the CD spectrum, Lipo-AcE4K penetrates further into the lipid bilayer upon neutralization of the acidic residues. However, the observed changes could also arise from the protection of the tryptophan residue from the aqueous medium through the formation of oligomeric complexes of the lipopeptide within the membrane.

c. Fusion of Liposomes Induced by AcE4K and Lipo-AcE4K

The destabilization of membranes accompanying the observed changes in peptide structure and membrane penetration was studied by monitoring the fusion of lipid vesicles as measured by lipid mixing, contents mixing and leakage. Membrane fusion was expected to depend on the extent of neutralization of the acidic residues of Lipo-AcE4K and to increase with decreasing pH.

The effects of peptide structure and membrane penetration as a function of pH on the stability of liposomal membranes and fusion of liposomes were monitored by the loss of RET between the fluorescently labeled lipids, NBD-PE and Rh-PE. Vesicles containing both probes are mixed with unlabeled vesicles, and membrane fusion results in probe dilution and increased NBD-PE fluorescence. Exchange of the labeled lipids does not occur over the duration of these experiments, even in highly aggregated systems (Hoekstra, et al., *Biochemistry*, 21:6097–6103 (1982)), and fluorescence increases only upon mixing of membrane lipids.

Figure 45A:
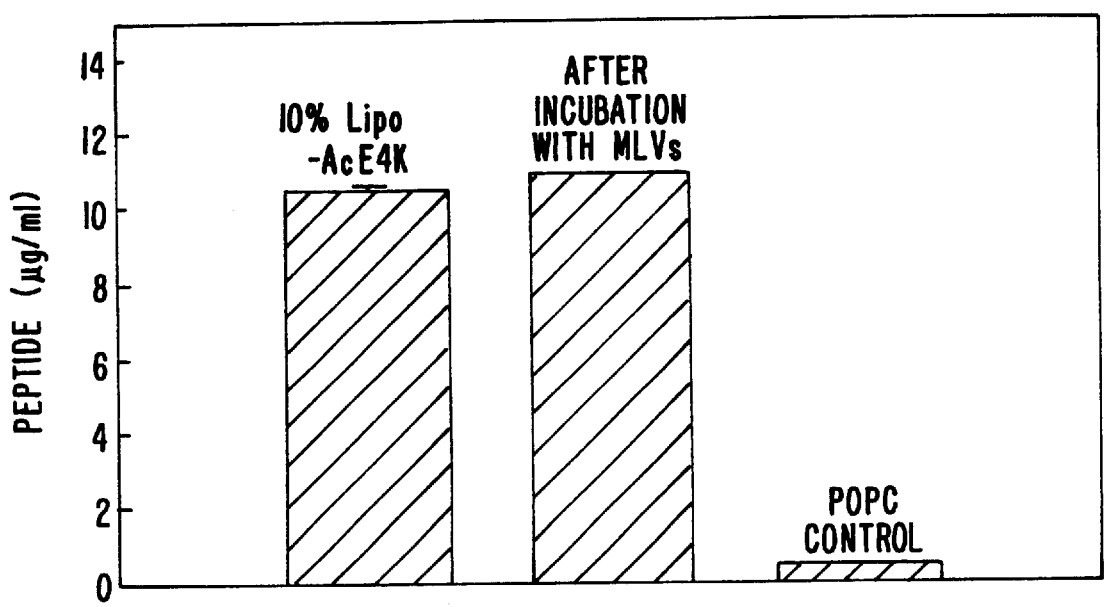
FIG. 45A: 10 mol % Lipo-AcE4K was added to prepared POPC LUVs, and the amount of peptide associated with POPC vesicles was determined by micro-BCA assay before and after incubation with POPC MLVs. A control experiment using LUVs without lipopeptide is also known. Assays were carried out in duplicate, and deviations from means were negligible except where error bars are shown.
Figure 45B:
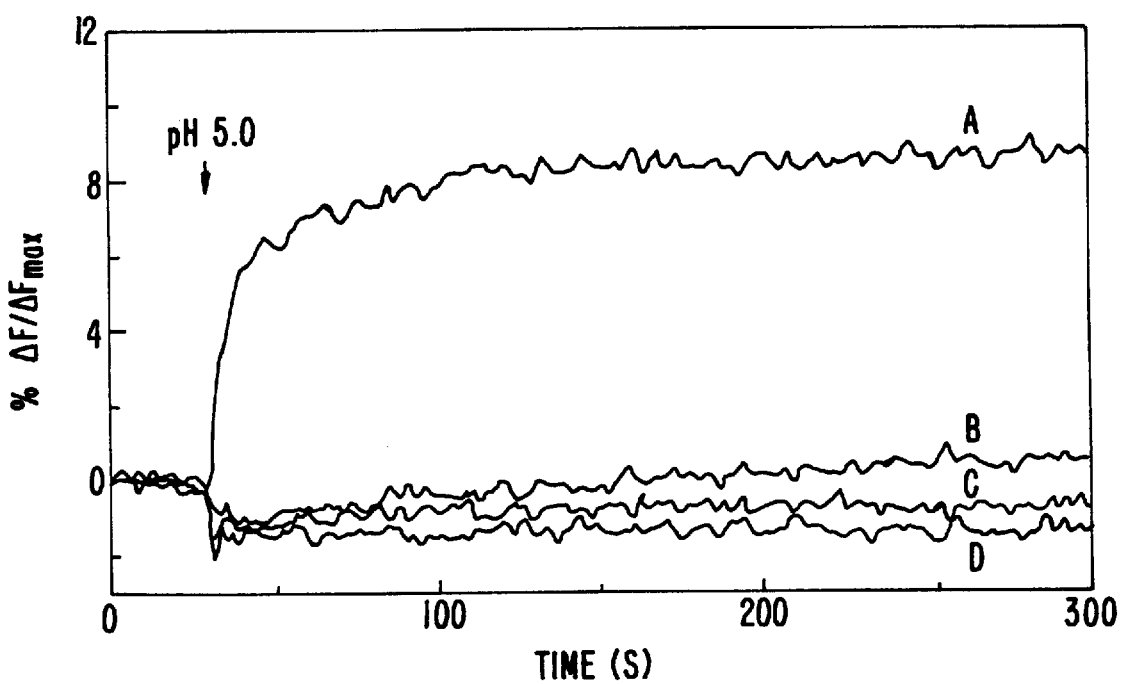
FIG. 45B: Lipid mixing assay were performed after preincubation of selected liposome populations with sufficient Lipo-AcE4K to achieve a 5 mol % concentration in liposomal outer monolayers. The lipopeptide was included in both fluorescently labeled and unlabeled populations (A), in labeled vesicles only (B), in unlabeled vesicles only (C), or in neither labeled nor labeled liposomes (D).

Initially, we looked at fusion of POPC LUVs with 5 mol % Lipo-AcE4K added to the preformed vesicles from a DMSO stock solution. Lipid mixing fluorescence time-courses upon acidification to PH's between 7.0 and 4.0 are shown in FIGS. 45A and 45B. No lipid mixing was observed above pH 6.0. However, there was a substantial increase in mixing between pH 5.75 and 5.5. These changes may have physiological importance, in that the pH of the endosomal interior falls in the range of 5 to 6. At pH 5.0 an initial rapid increase in NBD-PE fluorescence levels off over one to two minutes, indicating a transient destabilization of the membrane. Further decreases in pH give even greater lipid mixing, and at pH 4.0 the initial rapid increase in fluorescence is followed by a slower rise over several minutes. Similar experiments in which the free peptide, AcE4K, was added to POPC vesicles also gave lipid mixing, but at levels about half of those observed for the lipopeptide (data not shown).

Figure 44A:
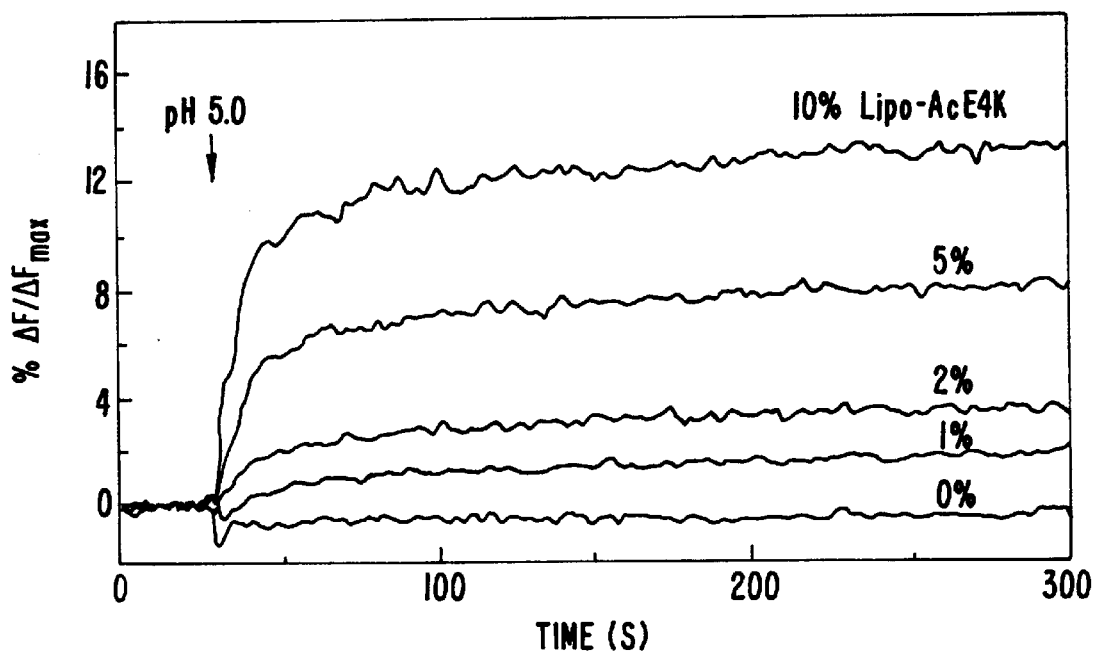
FIG. 44A: Varying amounts of lipopeptide were added to a 1:3 mixture of labeled and unlabeled vesicles (0.2 mM total lipid) from a 2 mM stock solution in DMSO, such that the final DMSO concentration was less than 1% by volume. Lipid mixing assays were as described above, adding 1 M HCl at 30 seconds to achieve a final pH of 5.0.

The effect of Lipo-AcE4K concentration in the outer monolayer of POPC vesicles on the degree of lipid mixing at pH 5.0 is shown in FIG. 44A. Small but significant increases in NBD-PE fluorescence is observed with as little as 1 mol % Lipo-AcE4K, and the level of mixing achieved increases up to 10 mol %, the maximum level assayed. In all cases, the observed increase in fluorescence is complete within 1 or 2 minutes. The transient nature of the lipid mixing in all of these cases suggests the loss of destabilizing capability of the lipopeptide, perhaps through conformational changes not detectable by CD experiments or through the formation of oligomeric complexes.

d. Contents Mixing and Leakage

To determine whether the pH-induced destabilization of membranes containing Lipo-AcE4K corresponded to fusion events with contents mixing subsequent to the observed lipid mixing, the ANTS-DPX contents mixing assay was used. In this assay, fusion between a liposome population containing the fluorescent marker ANTS and a second population containing the quencher DRX results in a loss of ANTS fluorescence. The assay is not affected by moderately acidic conditions and can distinguish contents mixing from probe leakage, since the latter results in an insufficient concentration of DPX to provide quenching. Leakage was separately determined by monitoring ANTS dequenching for liposomes containing both ANTS and DPX.

Figure 44B:
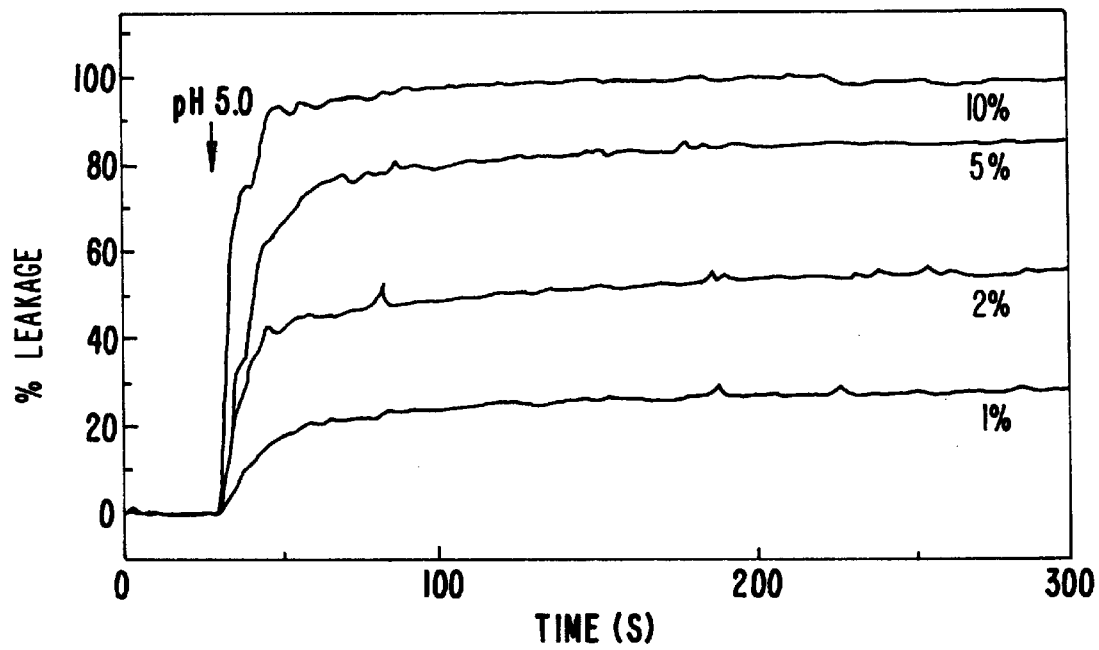
FIG. 44B: Vesicles containing 6 mM ANTS and 75 mM DPX dissolved in HMA buffer, pH 7.5, were diluted to 0.2 mM lipid prior to addition of varying amounts of lipopeptide from a 2 mM DMSO stock solution. At 30 seconds, 1 M HCl was added to achieve a pH of 5.0.

For the range of Lipo-AcE4K concentrations used above (I to 10 mol %) in POPC vesicles, no contents mixing was observed. The ANTS-DPX assay revealed only the leakage of vesicle contents upon decreasing the pH to 5.0, and the extent of leakage observed corresponded to the concentration of lipopeptide as shown in FIG. 44B. With 10 mol % Lipo-AcE4K in the outer monolayer, all of the probe leaked out within one minute. At lower lipopeptide concentrations, most of the leakage occurred within the first minute followed by much slower leakage. This behavior corresponds to the transient rapid lipid mixing which was previously observed, and again suggests a rapid loss of destabilizing capability for the lipopeptide.

The absence of contents mixing, the occurrence of rapid leakage and accompanying lipid mixing observed in these systems clearly do not describe the complete fusion process as achieved by the virus. The results are consistent with previous studies on the destabilization of lipid vesicles with viral fusion peptides. In no case has contents mixing arising from a non-leaky fusion event been convincingly demonstrated. However, the ability of the lipopeptide to transiently destabilize lipid bilayers suggests that fusion peptides have a functional role in destabilizing target membranes as well as an anchoring role in bringing fusing membranes into close apposition, and that the entire fusion protein is required to give a complete fusion event. This investigation was continued by looking at the ability of Lipo-AcE4K present in one membrane to destabilize synthetic and biological target membranes which are otherwise pH stable.

Prior to investigating the fusion of Lipo-AcE4K-containing liposomes to stable vesicles lacking lipopeptide or to biological membranes, it was necessary to demonstrate that the lipopeptide does not exchange out of lipid bilayers into potential "target" membranes, which would complicate interpretation of the lipid mixing results. The transfer of Lipo-AcE4K was investigated by incubating POPC LUVs containing 10 mol % Lipo-AcE4K added after vesicle formation with a large excess of POPC MLVs. The MLVs were separated from LUVs by centrifugation. A comparison of the peptide contents of the Lipo-AcE4K-bearing LUVs before and after incubation with MLVs is given in FIG. 44A. It is clear that there is no exchange of Lipo-AcE4K out of the LUV population when incubated with MLVs. A small increase in measured peptide content after the incubation can be attributed to interference in the assay caused by phospholipid as shown in the POPC control.

Given this result, the ability of POPC vesicles containing Lipo-AcE4K to fuse with POPC membranes lacking the lipopeptide was investigated. As seen in FIG. 44B, very little lipid mixing is observed when only one liposome population contains 5 mol % Lipo-AcE4K compared to the assay when the lipopeptide is present in both membranes. There was only a small difference in this result when the Lipo-AcE4K was incorporated into the fluorescently labeled population rather the unlabeled population, reflecting the probability differences resulting from the mixing ratio of 1:3 labeled to unlabeled.

e. Fusion and Leakage in EPC/Chol Vesicles

In order to achieve higher levels of membrane fusion, we have looked at the effect of Lipo-AcE4K on the stability of EPC/Chol (55:45) LUVs which more closely approximate the lipid composition of biological membranes. EPC is a naturally-occurring mixture of phosphatidylcholine species bearing a variety of fatty acyl chains, and it consists predominantly of POPC. While the addition of cholesterol to phospholipid bilayers decreases membrane permeability by effecting tighter packing lipids, cholesterol can also promote membrane fusion by inducing the formation of nonbilayer lipid phases.

Figure 46A:
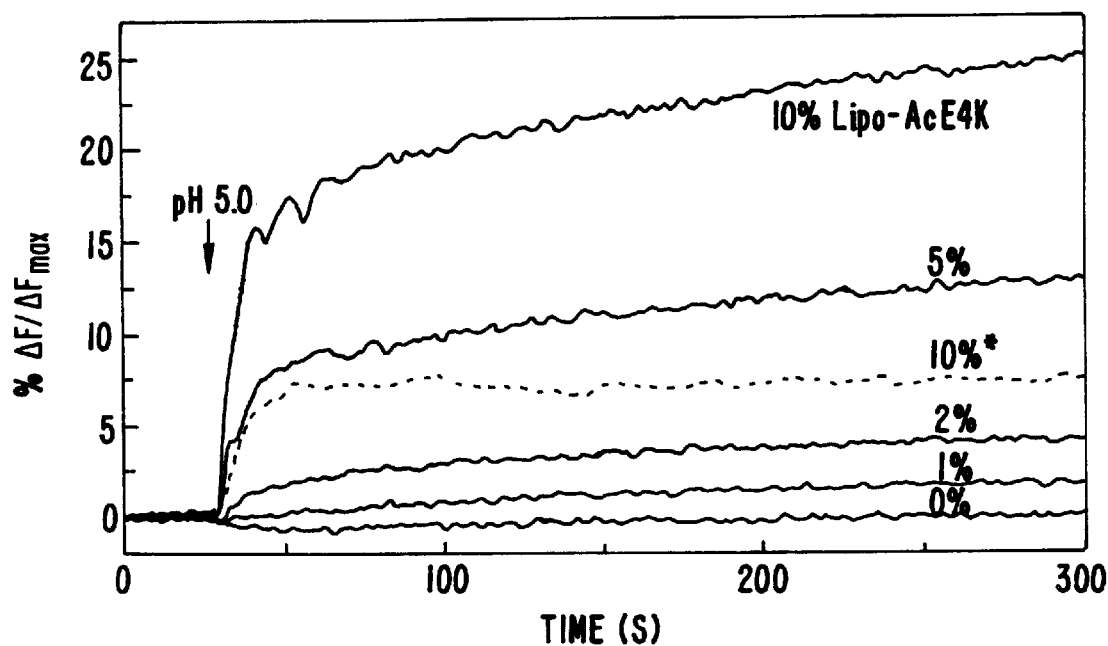
FIG. 46A: 0 to 10 mol % Lipo-AcE4K was added to a 1:3 mixture of labeled and unlabeled vesicles (0.2 mM total lipid) from a 2 mM stock solution in DMSO. Lipid mixing assays were as described above, adding 1 M HCl at 30 seconds to achieve a final pH of 5.0.
Figure 46B:
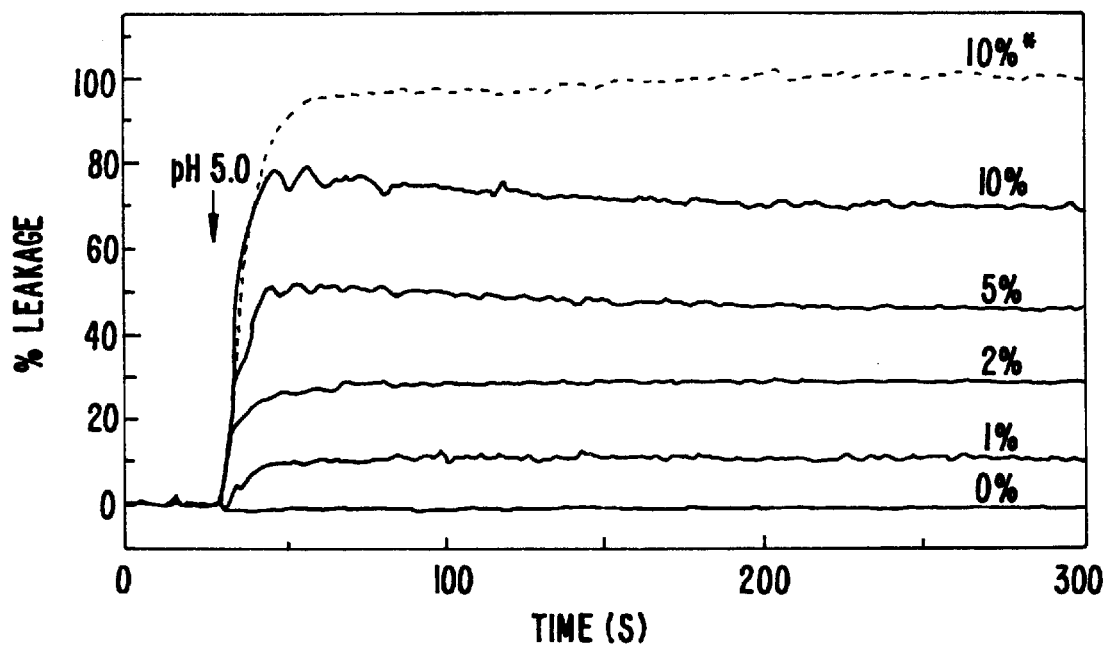
FIG. 46B: Leakage assays from 0 to 10 mol % Lipo-AcE4K added to EPC/Chol (55:45) liposomes containing 6 mM ANTS and 75 mM DPX. For comparison, corresponding assays for 10 mol % of the free peptide AcE4K is also shown (dotted lines).
Figure 47:
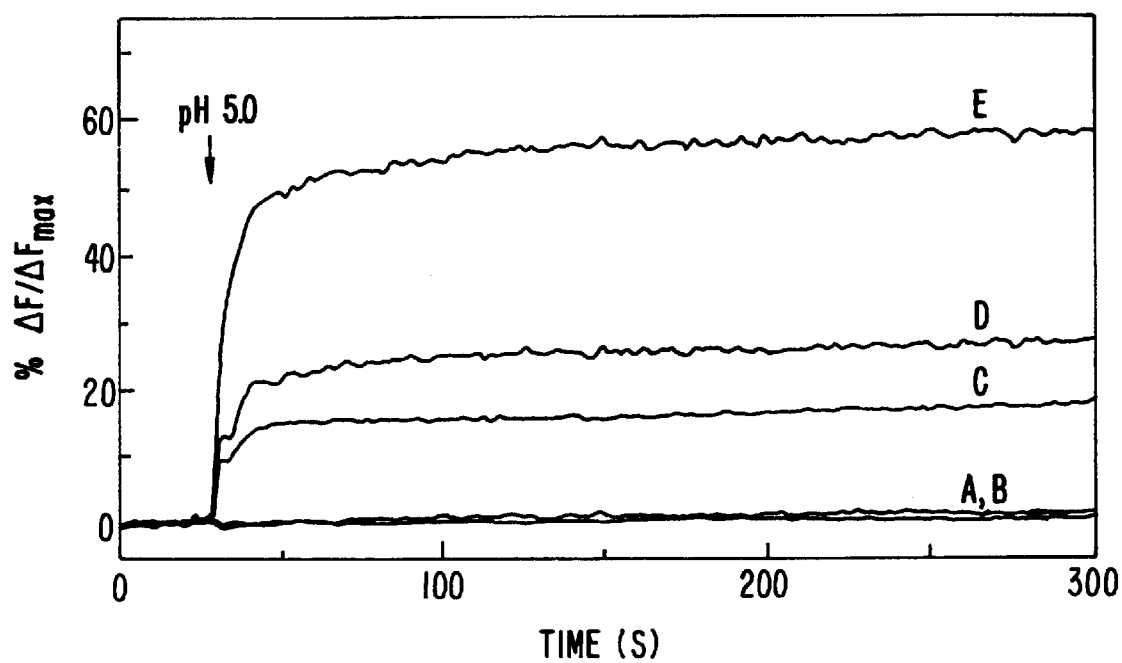
FIG. 47 illustrates the effect of transbilayer distribution of Lipo-AcE4K on lipid mixing in EPC/Chol (55:45) LUVs. 10 mol % Lipo-AcE4L was either present in the outer monolayer of liposomes (B, C) or in both monolayers (D, E) and was present in only the fluorescently labelled LUV population (B, D) or in both labelled and unlabelled LUVs (C, E). A control lipid mixing assay where neither vesicle population contained lipopeptide is also shown (A).

As shown in FIG. 46, Lipo-AcE4K at a concentration of 5 or 10 mol % is more effective at promoting lipid mixing in EPC/Chol (55:45) LUVs than in either EPC or POPC LUVs (see, FIG. 44A). Again, a transient rapid increase in fluorescence is observed; however, higher levels of fluorescence are achieved, and lipid mixing continues at a reduced rate for the duration of the assay. Interestingly, the corresponding ANTS-DPX leakage results for EPC/Chol liposomes, given in FIG. 46B, indicate lower levels of leakage at all concentrations of Lipo-AcE4K than were observed for POPC (FIG. 44B) or EPC (only 10 mol % Lipo-AcE4K data shown). It is remarkable that the inclusion of cholesterol appears to increase the destabilization caused by the lipopeptide, perhaps by the promotion of nonbilayer structures, while reducing the permeability of the destabilized membranes to the aqueous medium. However, leakage of vesicle contents remains substantial, and in no case was contents mixing of vesicles observed.

f. Effects of Transbilayer Distribution of Lipo-AcE4K

Increased levels of lipid mixing were observed in EPC/Chol (55:45) vesicles when Lipo-AcE4K was present on both the inner and outer monolayers of the liposomes. This was achieved by adding the lipopeptide to the lipid preparation prior to freeze-drying, hydration, and extrusion. As shown in FIG. 9, lipid mixing between LUVs containing mol % Lipo-AcE4K prepared by this method gave values of $\Delta F/\Delta T_{max}$ approaching 60% at 5 minutes. Furthermore, mixing these LUVs and an EPC/Chol (55:45) preparation lacking lipopeptide also resulted in substantial membrane fusion. In contrast, LUVs prepared as before with 10 mol % Lipo-AcE4K only on the outer monolayer could fuse with themselves, but not with EPC/Chol LUVs.

While the Lipo-AcE4K on the interior of vesicles is unable to penetrate the target membrane, it can apparently play a role in further destabilizing the membrane in which it is present. Presumably, this is as a result of reduction of the pH in the vesicle interior arising from the leakage induced by initial membrane destabilization.

g. Freeze-Fracture Electron Microscopy

Figure 48:
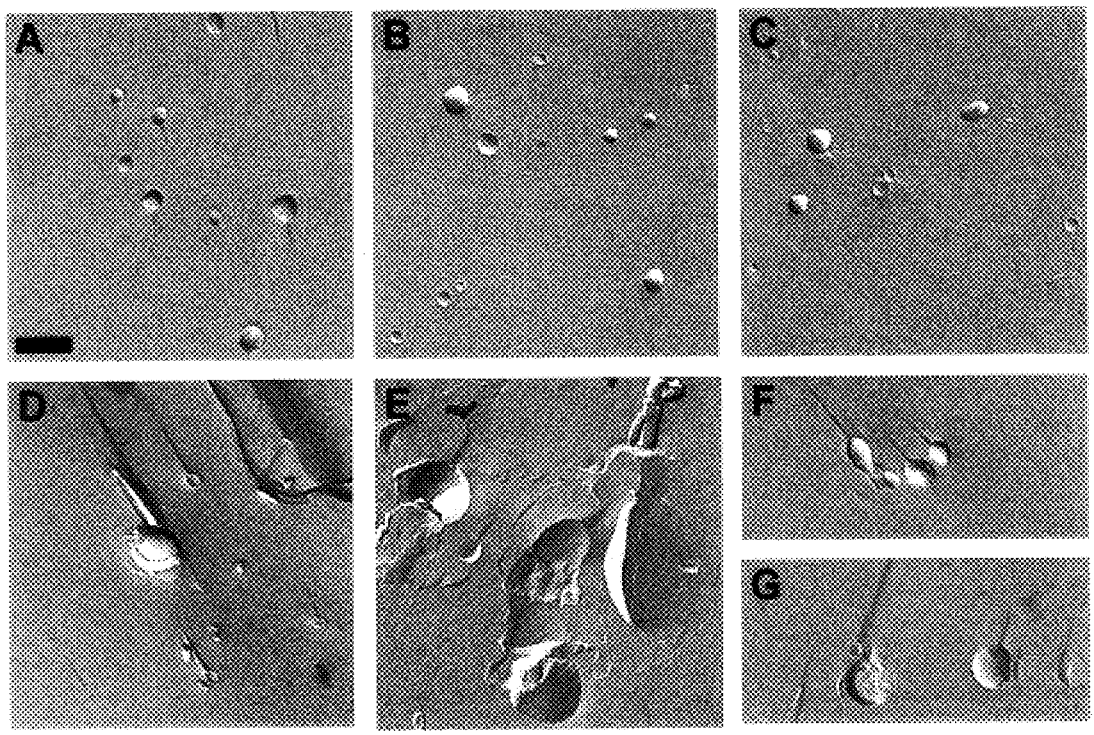
FIG. 48 sets forth the freeze-fracture electron micrographs of EPC/Chol liposomes: effect of Lipo-AcE4K and pH. EPC/Chol (55:45) LUVs were prepared with (C, D-F) and without (A, B) 10 mol % Lipo-AcE4K at a total lipid concentration of 5 mM in HMA buffer. Platinum-carbon replicas were prepared at pH 7.5 (A, C) or 5 minutes following acidification to pH 5.0 by the addition of 1 M HCl (B, D-F). Original magnification was 20,000×, and bars represent 200 nm.

The destabilization of lipid bilayers and lipid mixing induced by Lipo-AcEAK can also be seen in freeze-fracture micrographs shown in FIG. 48. EPC/Chol (55:45) samples without Lipo-AcE4K or those bearing Lipo-AcE4K at pH 7.5 give smooth fracture surfaces and have size distributions typical of those normally observed for LUVs extruded through 100 nm filters. Samples with 10 mol % Lipo-AcE4K at pH 5.0, however, have larger lipid structures, indicating fusion of liposomes. In addition, many of these larger structures exhibit rough surfaces which are believed to arise from penetration of the peptide portion of Lipo-AcE4K into the membrane. Furthermore, a large proportion of these vesicles are cross-fractured, indicating that the pH-induced insertion of the lipopeptide does indeed disrupt bilayer structure and stability. The limited size increase observed is consistent with the transient destabilization found in the lipid mixing and contents mixing assays.

h. Lipid Mixing with Erythrocyte Ghost Membranes

Ultimately, the destabilizing properties of Lipo-AcE4K directed toward biological membranes are of greatest interest. As a model for such systems, lipid mixing between EPC/Chol (55:45) liposomes containing Lipo-AcE4K with erythrocyte ghost membranes has been studied. The ghost preparation used here included 1 mM $MgSO_4$ in the lysis and washing buffers as described by Stock and Kant, supra (1974). While this results in the retention of a small amount of hemoglobin within the cells, it ensures rapid resealing and membrane integrity. Analysis for glycerol-3-phosphate dehydrogenase activity as described by Sigma confirmed the formation of sealed, right-side-out ghosts which was not the case for a preparation without 1 mM $MgSO_4$ (data not shown).

Figure 49:
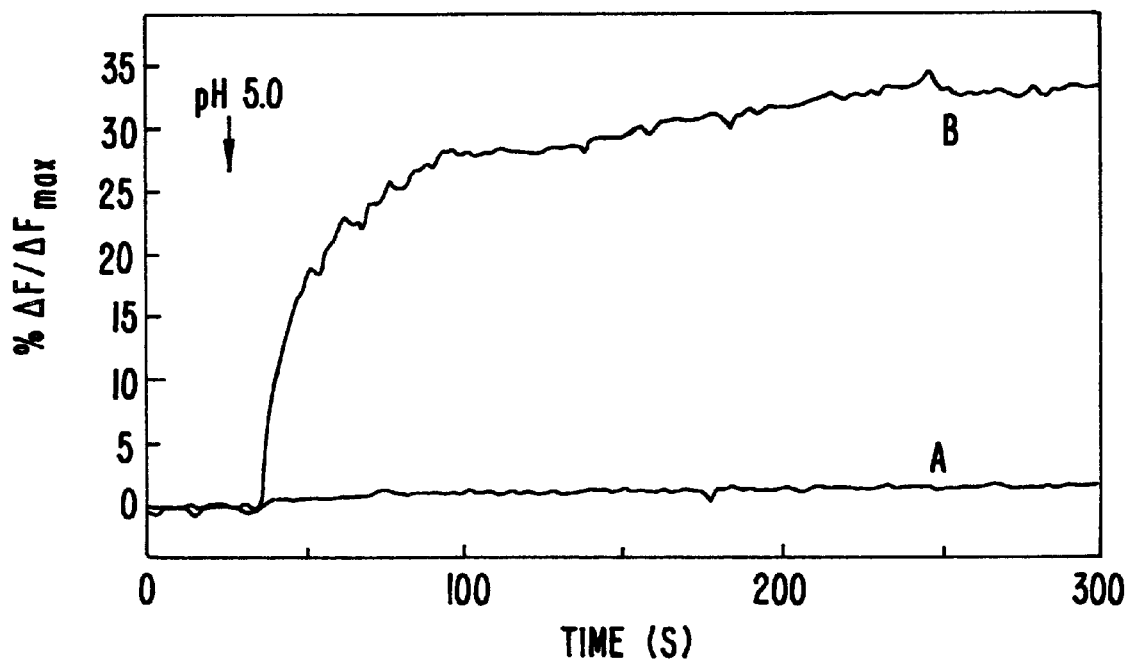
FIG. 49 illustrates the effect of method of lipopeptide incorporation into EPC/Chol (55:45) LUVs on lipid mixing with erythrocyte membranes.

Fluorescence lipid mixing assays with EPC/Chol erythrocyte ghosts were performed using two different liposome preparations. First, Lipo-AcE4K was added to EPC/Chol (55:45) LUVs from DMSO stock solution leading to incorporation of the lipopeptide into the outer monolayers of the LUVs at a concentration of approximately 10 mol % relative to surface-exposed lipid. Addition of erythrocyte ghosts to this preparation gave limited lipid mixing ($\Delta F/\Delta F_{max}$~2%) when the pH was decreased to 5.0 (FIG. 49). This result is in agreement with that shown above (FIG. 46(B)) in which incorporation of Lipo-AcE4K into the outer monolayer of one population of vesicles was insufficient to give substantial lipid mixing with a second population of membranes. A second liposome preparation with 10 mol % Lipo-AcE4K in EPC/Chol (55:45), incorporating lipopeptide into both inner and outer monolayers, gave much higher levels of lipid mixing with erythrocyte ghosts at pH 5.0, $\Delta F/\Delta F_{max}$ values approaching 40% at 5 minutes.

Figure 50:
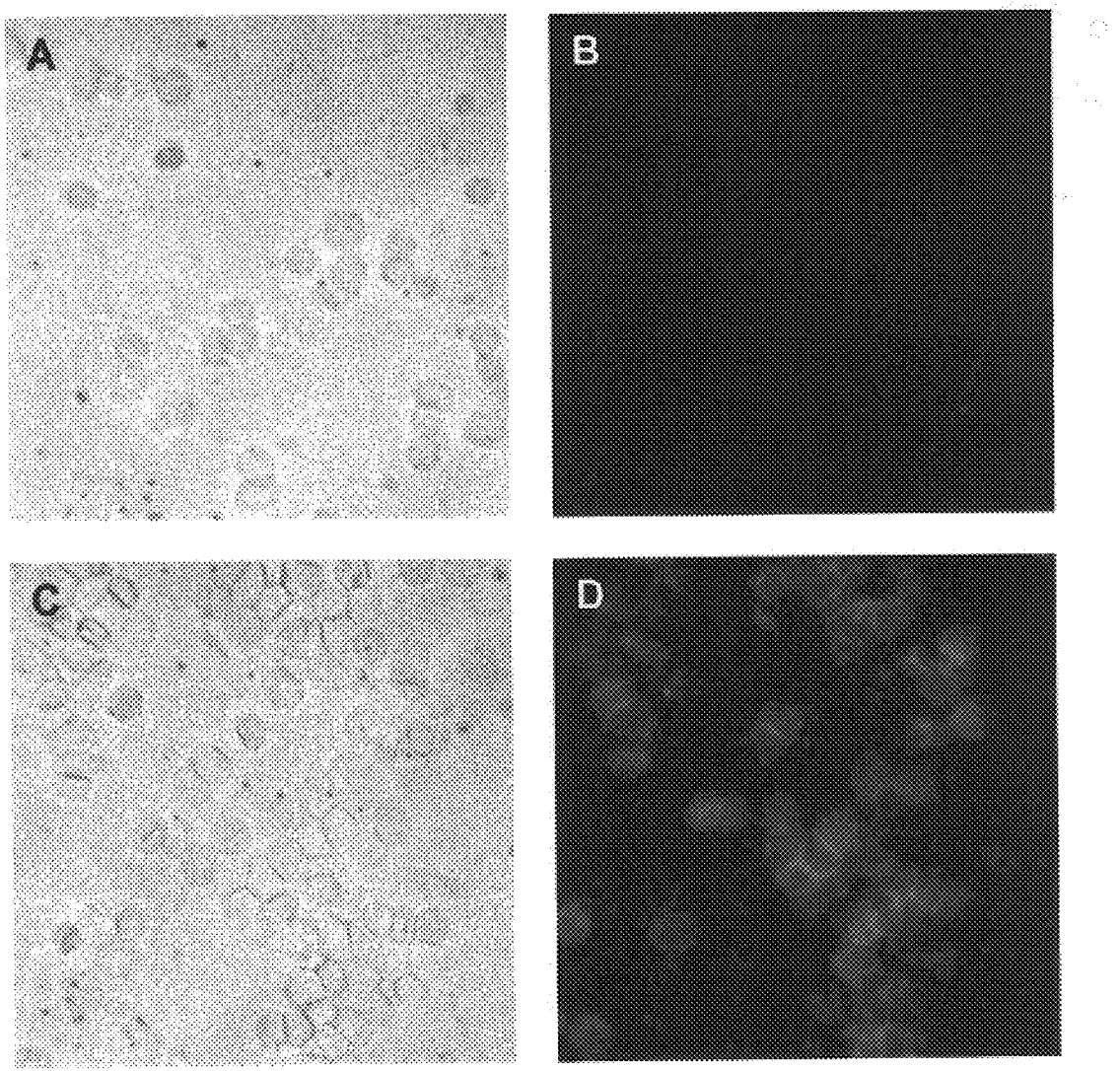
FIG. 50 sets forth the fluorescence micrographs showing the appearance of Rh-PE in erythrocyte membranes upon lipid mixing with 10 mol % Lipo-AcE4K in EPC/Chol (55:45). Liposomes were prepared from a co-lyophilized preparation of 10 mol % Lipo-AcE4K in EPC/Chol containing 0.5 mol % each of NBD-PE and Rh-PE. Liposome and erythrocyte membranes were mixed in a 1:3 lipid ratio (1 mM total lipid): (A) phase contrast and (B) Rh-PE fluorescence at pH 7.5; (C) phase contrast and (D) Rh-PE fluorescence after reducing pH to 5.0.

Finally, lipid mixing with erythrocyte ghosts was also demonstrated by fluorescence microscopy. The fluorescently labeled liposome preparations from the lipid-mixing assays were also used for this procedure, since they contain Rh-PE at a concentration which is greater than 80% self-quenching. The NBD-PE fluorescence is masked by a red transmission filter and is also readily photo-bleached under the conditions used here. This permits the detection of lipid mixing between labeled liposomes and erythrocyte ghosts as an increase in Rh-PE fluorescence upon dilution into the target and reduced self-quenching. FIG. 50 illustrates the effect of decreasing the pH for a mixture of LUVs prepared from EPC/Chol (55:45) co-lyophilized with 10 mol % Lipo-AcE4K and erythrocyte ghosts. Phase contrast micrographs are shown with corresponding fluorescence images at pH 7.5 and 5.0. While the appearance of Rh-PE fluorescence in the erythrocyte membranes is the most striking effect of lowering the pH, aggregation of the erythrocyte ghosts is also apparent. Interestingly, substantial levels of Rh-PE fluorescence and aggregation were also observed for EPC/Chol (55:45) LUVs pre-incubated with 10 mol % Lipo-AcE4K (i.e., outer monolayer only), although a much smaller increase in NBD-PE fluorescence was observed in the quantitative assay. Labeled EPC/Chol (55:45) LUVs without lipopeptide gave no lipid mixing or aggregation with erythrocyte ghosts at pH 5.0 (not shown). These micrographs were obtained using very small sample volumes (~5 μl) spread very thinly using large cover slips in order to arrest the erythrocyte ghosts without using high lipid concentrations or mounting solutions that can quench fluorescence. As a result, the majority of the membranes appear flattened, and lysis of the membranes begins to occur after several minutes.

3. EXPERIMENTAL FINDINGS

The free peptide only adopts an α-helical structure at low pH and only in the presence of lipid vesicles. This behavior is very similar to the wild-type (X31) and E4 peptides as studied by Rafalski, et al., supra (1991), except that they observed a low level of helical structure even at neutral pH. However, in that study, SUVs were used in the CD experiments, where LUVs have been used here. The higher curvature of small vesicles probably promotes hydrophobic interactions at pH 7.5 that are not observed in essentially planar LUV membranes. It is clear from the CD and Tryptophan fluorescence results that AcE4K requires neutralization of at least some of its acidic residues before it will interact with a lipid bilayer.

Coupling the peptide AcE4K to a lipid anchor effects the structure adopted by the peptide in the presence of lipid vesicles as well as the extent of its interactions with the lipid bilayer as a function of pH. The CD spectra of Lipo-AcE4K indicate that the anchored peptide adopts an α-helical structure at both neutral and acidic pH in contrast to the free peptide which is only α-helical at low pH in the presence of liposomes. This suggests that constraints imposed by the lipid anchor induce some peptide structure at neutral pH but prevent any further structural changes upon neutrazation of acidic residues. However, the tryptophan fluorescence maxima indicate that the anchored peptide clearly experiences a more hydrophobic environment upon acidification of the medium compared to its uncoupled counterpart. Based on the lipid-mixing and electron microscopy results presented here, we believe that this hydrophobic environment results from increased penetration of Lipo-AcE4K into the lipid bilayer and not simply from a loss of charge on neighboring residues or the formation of lipopeptide complexes.

Lipo-ACE4K destabilizes POPC and EPC/Chol lipid vesicles at mildly acidic pH, but not at pH 7.5. The extent of destabilization depends not only on pH and peptide concentration, but also on membrane composition and, at least in some preparations, on the transbilayer distribution of peptide. Membrane destabilization was determined quantitatively by lipid mixing and leakage of vesicle contents. Such results are very different from those reported for similar peptides. Duzgunes & Shavnin (1992) used a 17 amino acid peptide from the N-terminus of HA2 X31 wild-type sequence (refer to wt sequence reported above) and found that it gave extensive leakage for EPC LUVs at both neutral and low pH and no lipid mixing under any conditions. Rafalski, et al., supra, (1991) reported pH-dependent leakage for the 20 amino acid wt and for E4, but no lipid mixing in either POPC or POPC/Chol vesicles. It is clear that features such as peptide length, acidity, and membrane-anchoring all influence the membrane-destabilizing ability of these peptides.

The lipid mixing and leakage results presented here indicate extensive but short-lived membrane destabilization by 1 to 10 mol. % Lipo-AcE4K in both POPC and EPC/Chol vesicles. The rapid loss in destabilizing capacity may be due to the formulation of a membrane-stable conformation, a re-orientation of the lipopeptide, or the formation of stabilizing oligomeric complexes upon interaction with the lipid bilayer. The event appears to be accompanied by membrane penetration of the anchored peptide.

In addition to lipopeptide concentration, the extent of lipid mixing and leakage depend upon the lipid composition of the membranes involved. Lipo-AcE4K gave higher levels of lipid mixing in EPC/Chol (55:45) LUVs than in EPC or POPC LUVs. We tentatively attribute this difference to the ability of cholesterol to promote non-bilayer intermediates leading to membrane fusion [26]. Curiously, the increases in lipid mixing were accompanied by decreases in the extent of leakage at all lipopeptide concentrations. While cholesterol is known to reduce the permeability of phospholipid membranes, it was not expected to exhibit this property while also promoting lipid mixing.

The transbilayer distribution of the lipopeptide also influences the degree of lipid mixing observed. When Lipo-AcE4K was added to preformed vesicles, lipid mixing was only substantial between vesicle populations that each contained the lipopeptide. Very little lipid mixing was observed when only one population contained as much as 10 mol % Lipo-AcE4K. This result suggests that when Lipo-AcE4K is incorporated into the outer membranes of lipid vesicles in this way, it can only penetrate and destabilize the membrane in which it is anchored. Alternatively, if it inserts into the membrane of target vesicles, it does not destabilize the target vesicles sufficiently to promote lipid mixing between the two populations. In caution it should be noted that fusion with the labeled population of lipopeptide-bearing vesicles which cannot be detected by the assay may simply be the predominant process and that lipid mixing with a second population would be promoted under more constrained circumstances, e.g., with an endosome.

Incorporation of Lipo-AcE4K into both inner and outer leaflets of EPC/Chol (55:45) LUVs not only gave higher levels of lipid mixing between populations of vesicles containing the lipopeptide , but also caused these vesicles to fuse with liposomes lacking Lipo-AcE4K and with erythrocyte ghosts at low pH. The increase in lipid mixing provided by the presence of lipopeptide on the inner surface of the vesicle membrane must arise from the capability of Lipo-AcE4K to destabilize the membrane in which it is anchored since in this case it is unable to insert into an external lipid bilayer.

Fusion of EPC/Chol (55:45) LUVs containing 10 mol % Lipo-AcE4K was also observed by freeze-fracture electron microscopy. At pH 5.0, large lipid vesicles with diameters of several hundred nanometers were formed. This limited size increase, compared to the extensive fused structures found in $Ca^{2+}$-induced fusion of negatively charged liposomes, is consistent with the transient destabilization indicated by the lipid mixing and contents mixing results. The freeze-fracture micrographs also show very rough lipid surfaces and extensive cross-fracturing, both of which can be attributed to destabilization of the membrane structure by the lipopeptide. Fluorescence microscopy of erythrocyte ghosts incubated with these liposomes indicated not only pH-dependent lipid mixing with but also aggregation of the ghosts at low pH. No Rh-PE fluorescence was observed in the ghosts at pH 7.5 for either preparation or for EPC/Chol LUVs without Lipo-AcE4K at either pH 7.5 or pH 5.0.

In summary, the lipopeptide Lipo-AcE4K forms stable bilayers in POPC and EPC/Chol LUVs at concentrations up to 10 mol % at pH 7.5. Destabilization of these lipid vesicles can be induced by decreasing the pH below 6.0 which corresponds to the conditions under which the viral protein, influenza HA, from which it is derived causes membrane fusion. This membrane destabilization not only results in extensive leakage of liposomal contents, as has been demonstrated with a variety of other viral fusion peptides and synthetic amphipathic helicies, but also in lipid mixing of LUVs as determined by fluorescent lipid probe dilution, and coalescence of lipid membranes shown by freeze-fracture electron microscopy. The extent of lipid mixing depends on pH, membrane composition, and the concentration of the lipopeptide as well as on its distribution between the membrane leaflets. Addition of 10 mol % Lipo-AcE4K to EPC/Chol (55:45) LUVs gave lipid mixing with erythrocyte ghosts, the first example of fusion induced by a membrane-anchored fusion peptide with a biological membrane.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A lipopeptide, said lipopeptide comprising:
a lipid covalently attached to a fusion peptide by means of an amide bond, wherein said amide bond is formed from a lipid having a carboxyl group and an amino group from said fusion peptide, wherein said lipid is a diacyglycerol, and wherein said fusion peptide is a member selected from the group consisting of Ac-GLFEAIAGFIENGWEGMIDGK (SEQ ID NO:3);
WEAALAEALAEALAEHLAEALAEALEALAA (SEQ ID NO:4);
GGYCLTRWMLIEAELKCFGNTAV (SEQ ID NO:5);
GGYCLTKWMILAAELKCFGNTAV (SEQ ID NO:6);
GGYCLEKWMIVASELKCFGNTA (SEQ ID NO:7);
GGYCLEQWAIIWAGIKCFDNTVM (SEQ ID NO:8);
GLFEALAEFIEGGWEGLIEG; (SEQ ID NO:9);
GLFEAIAEFIEAIAEFIEG (SEQ ID NO:10);
GWEGLIEGIEGGWEGLIEG (SEQ ID NO:11);
GLFEAIAEFIPGGWEGLIEG (SEQ ID NO:12);
GLLEELLELLEELWEELLEG (SEQ ID NO:13);
Ac-LARLLARLLARL-NHCH3 (SEQ ID NO:14);
Ac-LARLLPRLLARL-NHCH3 (SEQ ID NO:15);
Ac-LPRLLPRLLARL-NHCH3 (SEQ ID NO:16);
Ac-LPRLLPRLLPRL-NHCH3 (SEQ ID NO:17);
FEAALAEALAEALA (SEQ ID NO:18);
Myr-FEAALAEALAEALA (SEQ ID NO:19);
WEAALAEALAEALAC (SEQ ID NO:20);
poly(Glu-Aib-Leu-Aib) (SEQ ID NO:21);
wherein:
Myr represents myristic acid; and
Aib represents 2-aminoisobutyric acid; and
and conservative modifications thereof.

2. A lipopeptide, said lipopeptide comprising:
a lipid covalently attached to a fusion peptide by means of an amide bonds wherein said amide bond is formed from a lipid having a carboxyl group and an amino group from said fusion peptide, and wherein said fusion peptide comprises the following amino acid sequence Ac-GLFEAIAGFIENGWGMIDGK and conservative modifications thereof.

3. A lipopeptide in accordance with claim 2 wherein said lipid is a 1,2-distearoyl-sn-glycerol.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

```
Gly Leu Phe Gly Ala Ile Ala Gly Phe Ile Glu Asn Gly Trp Glu Gly
1               5                   10                  15

Met Ile Asp Gly
            20
```

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Gly Leu Phe Glu Ala Ile Ala Gly Phe Ile Glu Asn Gly Trp Glu Gly
1               5                   10                  15

Met Ile Asp Gly
            20
```

(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-glycine"

(xi) SEQUENCE DESCRIPTION: SEQ ID NO:3:

```
Xaa Leu Phe Glu Ala Ile Ala Gly Phe Ile Glu Asn Gly Trp Glu Gly
1               5                   10                  15

Met Ile Asp Gly Lys
            20
```

(2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Gly Gly Tyr Cys Leu Thr Arg Trp Met Leu Ile Glu Ala Glu Leu Lys
1               5                   10                  15

Cys Phe Gly Asn Thr Ala Val
            20

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Gly Gly Tyr Cys Leu Thr Lys Trp Met Ile Leu Ala Ala Glu Leu Lys
1               5                   10                  15

Cys Phe Gly Asn Thr Ala Val
            20

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Gly Gly Tyr Cys Leu Glu Lys Trp Met Ile Val Ala Ser Glu Leu Lys
1               5                   10                  15

Cys Phe Gly Asn Thr Ala Ile
            20

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Gly Gly Tyr Cys Leu Glu Gln Trp Ala Ile Ile Trp Ala Gly Ile Lys
1               5                   10                  15

Cys Phe Asp Asn Thr Val Met
            20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Gly Leu Phe Glu Ala Leu Ala Glu Phe Ile Glu Gly Gly Trp Glu Gly
1               5                   10                  15

Leu Ile Glu Gly
            20

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Gly Leu Phe Glu Ala Ile Ala Glu Phe Ile Glu Ala Ile Ala Glu Phe
1               5                   10                  15

Ile Glu Gly (2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Gly Trp Glu Gly Leu Ile Glu Gly Ile Glu Gly Gly Trp Glu Gly Leu
1               5                   10                  15

Ile Glu Gly (2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Gly Leu Phe Glu Ala Ile Ala Glu Phe Ile Pro Gly Gly Trp Glu Gly
1               5                   10                  15

Leu Ile Glu Gly
            20

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Gly Leu Leu Glu Glu Leu Leu Glu Leu Leu Glu Glu Leu Trp Glu Glu
1               5                   10                  15

Leu Leu Glu Gly
            20

(2) INFORMATION FOR SEQ ID NO:14:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-leucine"

(ix) FEATURE:
        (A) NAME/KEY: Modified-site
        (B) LOCATION: 12
        (D) OTHER INFORMATION: /product= "OTHER"
            /note= "Xaa = leucine methylamide"

(xi) SEQUENCE DESCRIPTION: SEQ ID NO:14:

Xaa Ala Arg Leu Leu Ala Arg Leu Leu Ala Arg Xaa
1               5                   10

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-leucine"

(ix) FEATURE:
        (A) NAME/KEY: Modified-site
        (B) LOCATION: 12
        (D) OTHER INFORMATION: /product= "OTHER"
            /note= "Xaa = leucine methylamide"

(xi) SEQUENCE DESCRIPTION: SEQ ID NO:15:

Xaa Ala Arg Leu Leu Pro Arg Leu Leu Ala Arg Xaa
1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-leucine"

(ix) FEATURE:
        (A) NAME/KEY: Modified-site
        (B) LOCATION: 12
        (D) OTHER INFORMATION: /product= "OTHER"
            /note= "Xaa = leucine methylamide"

```
    (xi) SEQUENCE DESCRIPTION: SEQ ID NO:16:

Xaa Pro Arg Leu Leu Pro Arg Leu Leu Ala Arg Xaa
1               5                   10

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-acetyl-leucine"

(ix) FEATURE:
        (A) NAME/KEY: Modified-site
        (B) LOCATION: 12
        (D) OTHER INFORMATION: /product= "OTHER"
            /note= "Xaa = leucine methylamide"

(xi) SEQUENCE DESCRIPTION: SEQ ID NO:17:

Xaa Pro Arg Leu Leu Pro Arg Leu Leu Pro Arg Xaa
1               5                   10

(2) INFORMATION FOR SEQ ID NO:18:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Phe Glu Ala Ala Leu Ala Glu Ala Leu Ala Glu Ala Leu Ala
1               5                   10

(2) INFORMATION FOR SEQ ID NO:19:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-myristoyl-phenylalanine"

(xi) SEQUENCE DESCRIPTION: SEQ ID NO:19:

Xaa Glu Ala Ala Leu Ala Glu Ala Leu Ala Glu Ala Leu Ala
1               5                   10

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS:
```

-continued

```
        (D) TOPOLOGY: linear (ii) MOLECULE TYPE: peptide (xi) SEQUENCE DESCRIPTION: SEQ ID NO:20:

Trp Glu Ala Ala Leu Ala Glu Ala Leu Ala Glu Ala Leu Ala Cys
1               5                  10                  15

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "Aib"

(ix) FEATURE:
        (A) NAME/KEY: Modified-site
        (B) LOCATION: 4
        (D) OTHER INFORMATION: /product= "Aib"

(xi) SEQUENCE DESCRIPTION: SEQ ID NO:21:

Glu Xaa Leu Xaa
1
```